(12) United States Patent
Ohgiya et al.

(10) Patent No.: US 10,006,056 B2
(45) Date of Patent: Jun. 26, 2018

(54) YEAST HAVING ENHANCED XYLOSE FERMENTATION ABILITY, AND USE THEREFOR

(71) Applicant: NATIONAL INSTITUTE OF ADVANCED INDUSTRIAL SCIENCE AND TECHNOLOGY, Tokyo (JP)

(72) Inventors: Satoru Ohgiya, Sapporo (JP); Yoichi Kamagata, Sapporo (JP); Kazuhiro Fujimori, Tsukuba (JP); Takehiko Sahara, Tsukuba (JP); Takashi Akamatsu, Kumamoto (JP); Hisataka Taguchi, Kumamoto (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days. days.

(21) Appl. No.: 14/910,810

(22) PCT Filed: Aug. 8, 2014

(86) PCT No.: PCT/JP2014/071109
§ 371 (c)(1),
(2) Date: Feb. 8, 2016

(87) PCT Pub. No.: WO2015/020216
PCT Pub. Date: Feb. 12, 2015

(65) Prior Publication Data
US 2016/0298140 A1 Oct. 13, 2016

(30) Foreign Application Priority Data
Aug. 8, 2013 (JP) ................. 2013-165366

(51) Int. Cl.
| | | |
|---|---|---|
| C12N 1/00 | (2006.01) |
| C12P 7/46 | (2006.01) |
| C07H 21/02 | (2006.01) |
| C07H 21/04 | (2006.01) |
| A23C 9/12 | (2006.01) |
| C12P 7/06 | (2006.01) |
| C12R 1/865 | (2006.01) |
| C07K 14/39 | (2006.01) |
| C12P 7/04 | (2006.01) |
| C12P 7/16 | (2006.01) |
| C12P 7/20 | (2006.01) |
| C12P 7/54 | (2006.01) |
| C12P 7/56 | (2006.01) |
| C07K 14/395 | (2006.01) |

(52) U.S. Cl.
CPC ............... *C12P 7/06* (2013.01); *C07K 14/39* (2013.01); *C07K 14/395* (2013.01); *C12P 7/04* (2013.01); *C12P 7/16* (2013.01); *C12P 7/20* (2013.01); *C12P 7/46* (2013.01); *C12P 7/54* (2013.01); *C12P 7/56* (2013.01); *C12R 1/865* (2013.01); *Y02E 50/10* (2013.01); *Y02E 50/17* (2013.01)

(58) Field of Classification Search
None
See application file for complete search history.

(56) References Cited

U.S. PATENT DOCUMENTS

2003/0039658 A1* 2/2003 Estable .................. C07K 14/47
424/185.1

FOREIGN PATENT DOCUMENTS

JP 201183255 A 4/2011

OTHER PUBLICATIONS

UniProt Accession No. Q02100, created on Sep. 30, 1993and updated the text on Jul. 9, 2004, Transcription factor SKO1, bZIP protein or CRE-binding protein.*
Boles et al. Characterization of a glucose-repressed pyruvate kinase (Pyk2p) in *Saccharomyces cerevisiae* that is catalytically insensitive to fructose-1,6-bisphosphate., J. Bacteriology, 179: 2987-2993, 1997.*
Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36)11643-50.*
Kisselev L., Polypeptide release factors in prokaryotes and eukaryotes: same function, different structure. Structure, 2002, vol. 10: 8-9.*
Jin et al. (*Saccharomyces cerevisiae* engineered for xylose metabolism exhibits a respiratory response. Applied and Environmental Microbiology, Nov. 2004, vol. 70(11):p. 6816-6825.*
Gordon, J.L. et al., "Evolutionary erosion of yeast sex chromosomes by mating-type switching accidents," PHAS, Dec. 13, 2011, 109(50), pp. 20024-2-20024-29, particularly, Summary, paragraph of Materials and Methods.

(Continued)

*Primary Examiner* — Iqbal H Chowdhury
(74) *Attorney, Agent, or Firm* — Hunton Andrews Kurth LLP

(57) ABSTRACT

The present invention pertains to: mutant genes having a mutation such as a base substitution in the MTH1, GRR1 and/or CDC19 coding regions thereof; mutant proteins coded by said mutant genes; an upstream region of the GRR1 coding region having a mutation such as a base substitution; a yeast such as *Saccharomyces* having said upstream region; and a method for producing a substance such as ethanol by using said yeast.

14 Claims, 24 Drawing Sheets

(56) References Cited

OTHER PUBLICATIONS

H2B1A6, UniProt, Mar. 21, 2012, [retrieved on Nov. 4, 2014]. Retrieved from the Internet: ,URL: http://www.uniprot.org/uniprot/H2B1A6., entire text, particularly, sequences (With respect to one of the polypeptides encoded by the yeasts set forth in the above-mentioned document by Gordon et al., the amino acid sequence thereof is set forth in this document.)

Tomitaka, M. et al., "Isolation and characterization of a mutant recombinant *Saccharomyces cervisiae* strain with high efficiency xylose utilization," Journal of Biosciencee and Bioengineering, Jun. 27, 2013, 116(6), pp. 706-715.

Wei, N. et al., "Deletion of FPS1, Encoding Aquaglyceroporin Fps1p, Improves Xylose Fermentation by Engineered *Saccharomyces cerevisiae*," Applied and Environnmental Microbiology, 79(10), 2013-05, pp. 3193-3201.

Mitsui, K. et al., "*Saccharomyces cerevisiae* glucose signalling regulator Mth1p regulates the organellar Na+/H+ exchanger Hnx1p," Biochem. J., 2010, 432, pp. 343-352.

Horak, J. et al., "The ubiquitin ligase SCFGrr1 is required for Gal2p degradation in the yeast *Saccharomyces cerevisiae*," Biochemical and Biophysical Research Communications, 2005, 335, pp. 1185-1190.

Forsburg, S.L. et al., "Mutational Analysis of Cdc19p, a Schizosaccharomyces pombe MCM Protein," Genetics, 1997, 147, pp. 1025-1041.

Fujimori, Kazuhiro et al., "Identification and characterization of the hex3 mutation leading to rapid assimilation of the xylose in a recombinant *Saccharomyces cerevisiae*," Dai 65 Kai Abstracts of the Annual Meeting of the Society for Biotechnology, Japan, Aug. 25, 2013, p. 62 (No. 1P-179).

Fujimori, Kazuhiro et al., "Xylose Shikasei Kojo ni Kakawaru *Saccharomyces cerevisiae* HEX1 Idenshi no Tokutei," Japan Society for Bioscience, Biotechnology, and Agrochemistry 2014 Nendo (Deisei 26 Nendo ) Takai Koen Yoshishu, Mar. 5, 2014, lecture No. 2A01a01.

Fujimori, Kazuhiro et al., "Konodo Xylose Shika o Michibiku *Saccharomyces cerevisiae* SXM1 Idenshi no Tokutei," Japan Society for Bioscience, Biotechnology, and Agrochemistry 2014 Nendo (Heisei 26 Nendo) Takikai Koen Yoshishu, Mar. 5, 2014, lecture No. 2A01a02.

Fujimori, Kazuhiro et al., "Konodo Xylose Shika ni Kakawaru *Saccharomyces cerevisiae* SXM2 Idenshi no Tokutei," Japan Society for Bioscience, Biotechnology, and Agrochemistry 2014 Nendo (Heisei 26 Nendo) Taikai Koen Yoshishu, Mar. 5, 2014, lecture No. 2A01a03.

International Search Report in PCT/JP2014/071109, dated Nov. 18, 2014.

T. Tomitaka et al, Isolation and Characterization of a Mutant of *Saccharomyces cerevisiae* Enabling Assimilation and Fermentation of High Concentrations of Xylose, Abstract for Oral Presentation for Japan Society for Bioscience, Biotechnology, and Agrochemistry, Mar. 5, 2012.

T. Tomitaka et al, Isolation and Characterization of a Mutant of *Saccharomyces cerevisiae* Enabling Assimilation and Fermentation of High Concentrations of Xylose, Oral Presentation for Japan Society for Bioscience, Biotechnology, and Agrochemistry, Kyoto Annual Meeting, Mar. 24, 2012.

S. Ogiya, Novel Technology for Breeding Yeast aimed at Efficient Production of Bioethanol—Use of Next-Generation Sequencer, Abstract for Oral Presentation on HiNT Seminar, Apr. 1, 2012.

Novel Technology for Breeding Yeast aimed at Efficient Production of Bioethanol—Use of Next-Generation Sequencer, Oral Presentation on HiNT Seminar, S. Ogiya, Apr. 24, 2012.

T. Akamatsu, Biotechnology for Biomass Refinery and Recycle-Oriented Society, Abstract for Oral Presentation on Program of China-Japan Symposium, Sep. 27, 2012.

T. Akamatsu, Biotechnology for Biomass Refinery and Recycle-Oriented Society, Presentation for Oral Presentation on Program of China-Japan Symposium, Sep. 28, 2012.

19th Annual Meeting of the Society for Biotechnology, Japan, Oita, Japan (2012) Proceedings, Abstracts for Oral Presentation on Kyushu Branch Meeting of The Society for Biotechnology, Oct. 1, 2012.

M. Tomitaka, Analysis of Mutants having Improved High Concentration Xylose Metabolism in Isogenic Industrial Yeast Strain, Oral Presentation on Kyushu Branch Meeting of The Society for Biotechnology, Dec. 1, 2012.

M. Tomitaka, Genetic Analysis of Mutants having Improved Xylose Metabolism in Isogenic Industrial Yeast Strain, Oral Presentation on Kyushu Branch Meeting of The Society for Biotechnology, Dec. 1, 2012.

S. Ogiya, Isolation and Characterization of C6/C5-Fermenting Yeast using Leading Edge Technology, Oral Presentation on Lab Tour by Study Group on Alcohol Fermentation and Biomass Utilization of Japan Bioindustry Association, Dec. 19, 2012.

M. Tomitaka, Isolation and Analysis of *Saccharomyces cerevisiae* Mutants Leading to Highly Efficient Glucose Assimilation, Abstract for Ph D. Defence at Graduate School of Engineering, Sojo University, Feb. 15, 2013.

M. Tomitaka, Isolation and Analysis of *Saccharomyces cerevisiae* Mutants Leading to Highly Efficient Glucose Assimilation, Presentation for Ph D. Defence at Graduate School of Engineering, Sojo University, Feb. 15, 2013.

M. Tomitaka et al, Isolation and characterization of a mutant recombinant *Saccharomyces cerevisiae* strain with high efficiency xylose utilization, Journal of Bioscience and Bioengineering, vol. xx, No. xx, 1-10, 2013.

* cited by examiner

FIG. 1
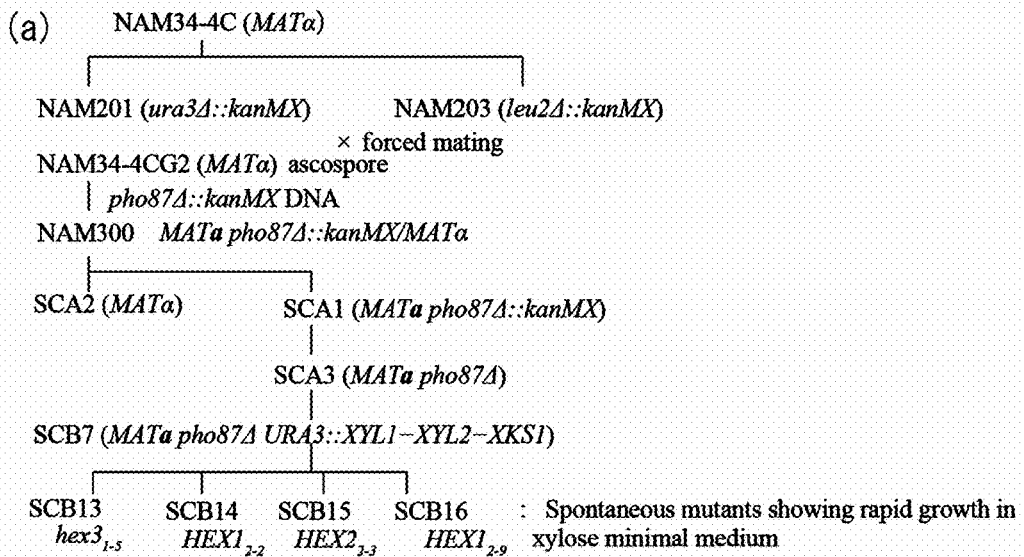
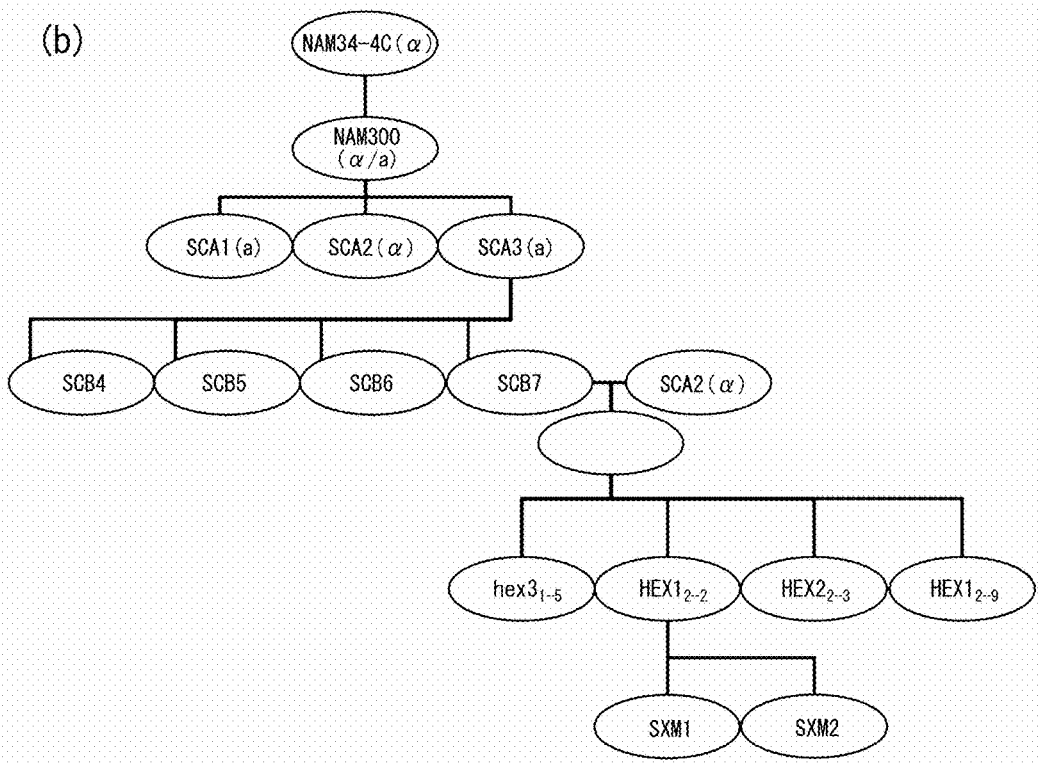

FIG. 6
(a)
S. cerevisiae SCC2-11B
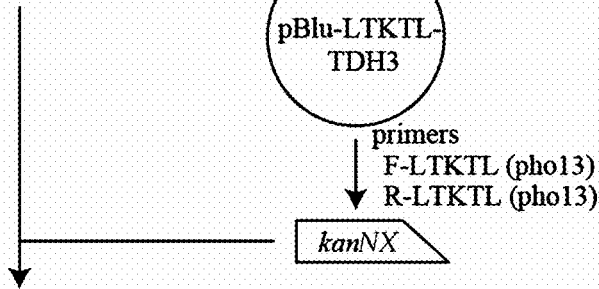
Strain pho13Δ::kanMX
(b) Dominant/recessive test
Hex3$_{1-5}$: phenotype Hex$^+$    pho13Δ: phenotype Hex$^+$    wild type: phenotype Hex$^-$
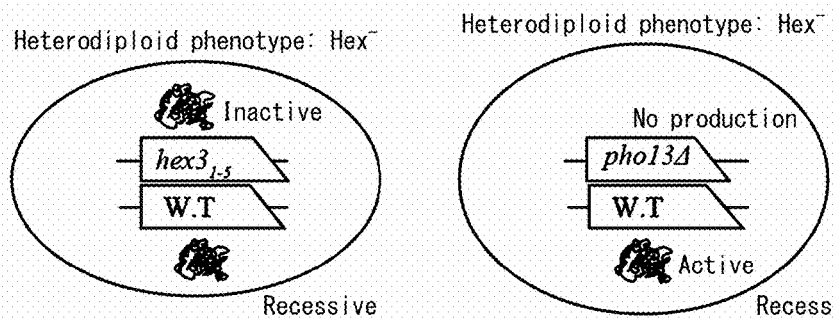
(c) Complementarity test.
If hex3$_{1-5}$ is pho13
Phenotype of diploid is Hex$^+$.
Non-complementary
If hex3$_{1-5}$ is different from pho13
Phenotype of diploid is Hex$^-$.
Complementary
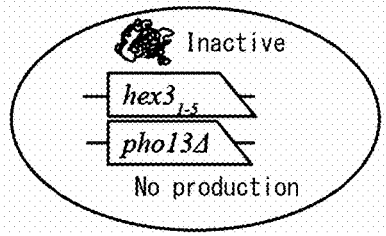
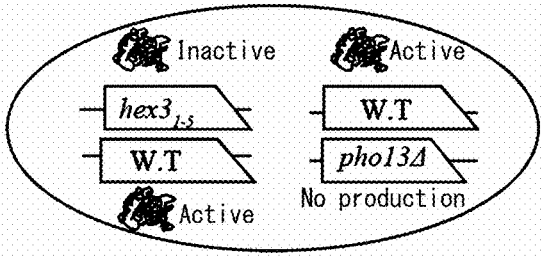

FIG. 8

(a) Gene structure near $HEX1_{2-2}$ candidate gene is analyzed against *Saccharomyces* database.

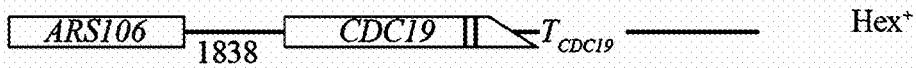

(b) kanMX gene is inserted into flanking region of $HEX1_{2-2}$ gene candidate. Confirmed whether Hex⁺ phenotype is retained, by inserted recombination.

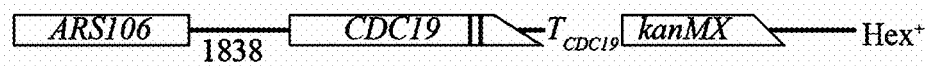

(c) If Hex⁺ phenotype is exhibited, transformation is accomplished by DNA including kanMX and mutation.

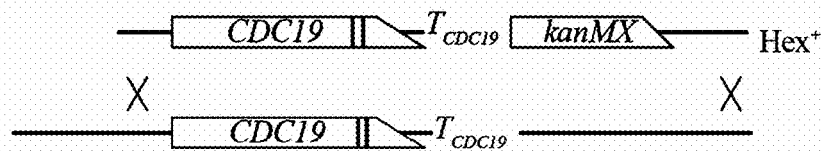

If G418-resistant transformant exhibits Hex⁺, then $HEX1_{2-2}$ is *CDC19*.
If necessary,
it is confirmed whether or not transformant definitely includes mutation.

FIG. 18
(a) Mutant mth1 gene structure of strain SXM1
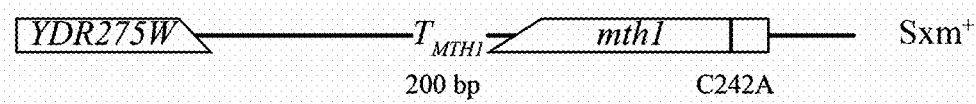
(b) Insertion of kanMX near mutant mth1
(c) Confirmation whether Sxm⁺ results from recombination of mutant mth1 in wild type
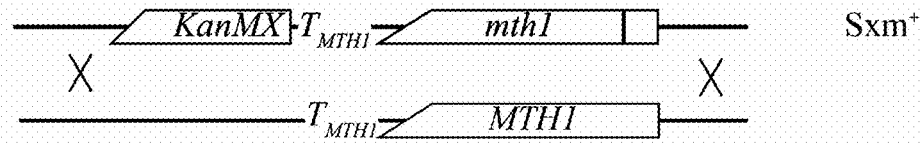

F-MTH1-UP1K (NotI) :TTTGCGGCCGCAGGAAGATTAAAATGAACTCTTCAAC

R-MTH1-dwn300 (NotI) : TTTGCGGCCGCTACGTTGGATGTCTGCGAT

YEAST HAVING ENHANCED XYLOSE FERMENTATION ABILITY, AND USE THEREFOR

CROSS-REFERENCE TO RELATED APPLICATIONS

The present application is a U.S. National Phase of International Patent Application No. PCT/JP2014/071109, filed on Aug. 8, 2014, and claims priority to Japanese Patent Application No. JP 2013-165366, filed on Aug. 8, 2013, each, including all disclosures and specifications, are hereby expressly incorporated herein in their entirety by reference thereto.

TECHNICAL FIELD

The present invention relates to a technique for producing useful substances by fermentation using microorganisms, and more specifically, it relates to yeast with enhanced xylose fermentative ability and to a method for producing useful substances using the yeast.

BACKGROUND ART

According to the New State Strategy of May, 2006, gasoline consumption in Japan is projected to be 60,000,000 kL by year 2030, of which 10% will be supplied by ethanol. Ethanol qualifies as a renewable energy, and it is produced by conversion of plant-derived components to ethanol by fermentation methods. For example, the budding yeast *Saccharomyces cerevisiae*, generally having high fermentation ability and high ethanol resistance, is a microorganism that has long been used to generate ethanol for production of alcoholic beverages, and it is also utilized in fuel ethanol production. What is known as "first generation" bioethanol is fuel ethanol produced using budding yeast or other microbes, using as the starting materials glucose from sugarcane and the like, or starch from corn and the like (which is easily convertable to glucose using enzymolysis, for example). Both domestically and abroad, fuel ethanol production has initially used glucose that can be assimilated by budding yeast, and starch that can be easily converted to glucose. On the other hand, since these materials are plants that are also used as foods and livestock feeds, there have been concerns that new problems will arise due to competition with use for foods. Therefore, expectations are increasing for "second-generation" bioethanols, with ethanol production from cellulosic biomass that are not usable for foods. Since cellulose can be decomposed into glucose by enzymes, it can likewise serve as a starting material for production of ethanol by fermentation. However, various problems are known to be associated with ethanol production from cellulosic biomass, depending on the combination of type of starting material, pretreatment method, saccharification process and fermentation process, and solutions to those problems are desired. While various resources have been considered for cellulosic starting materials, ligneous materials are the most promising, in terms of ensuring consistent ethanol production, because they are most abundant as cellulose resources. However, for efficient production of ethanol from ligneous materials, it is important for other components in addition to the cellulose that is the starting material for glucose. Ligneous materials are generally composed mainly of cellulose, hemicellulose and lignin, with a cellulose proportion of about 40% and a hemicellulose proportion of about 20% to 30%. Consequently, when a ligneous material, which contains a large amount of hemicellulose, is used as the starting material, it is desirable to accomplish ethanol conversion of the sugars such as xylose which are obtained from decomposition of hemicellulose by enzymes and the like. However, since budding yeast with high fermentation ability do not have functioning genes for assimilation of xylose, there is a problem in that they cannot produce ethanol from xylose. Therefore, the approach has been adopted of introducing xylose metabolizing enzymes of xylose-assimilating organisms into budding yeast, or enhancing endogenous metabolic functions to impart xylose-assimilating properties to budding yeast. Such exogenous xylose metabolizing enzymes include xylose reductase, xylitol dehydrogenase, xylulokinase, and xylose isomerase. In "Technological Research and Development for New Energies/New energy venture technological innovative projects (biomass)/Development of technique for bioethanol conversion from bamboo, for Kyushu Village Technology Architecture (2007-2008)" and "Development and research on processes for production of fuel ethanol from soft biomass" (2008-2009)", the present inventors have reported on our creative development of yeast suitable for production of ethanol from xylose. With yeast breeding techniques, there have been created yeast with enhanced xylose metabolism and yeast that are resistant to growth inhibition even in high-concentration xylose environments (PTL 1). However, the causative gene has not yet been identified.

In order to allow production of ethanol from xylose using budding yeast, it is essential to combine xylose reductase (XR), as the initial gene of xylose metabolism, and xylitol dehydrogenase (XDH), or to use xylose isomerase (XI). Still, while introduction of these genes allows production of ethanol from xylose, the production efficiency is very low. This is because production of ethanol from xylose requires endogenous enzymes of budding yeast in addition to the enzyme from the introduced genes, and they are functionally inadequate. Widely employed attempts to compensate for this inadequacy include forced expression of endogenous enzymes of budding yeast by gene recombination, and introduction of genes for analogous enzymes with greater affinity for xylose, from other organisms that are xylose-assimilating. The compensating enzyme can be easily selected by referring to a metabolic map, and examples include transporters (such as Hxt5) for incorporating xylose from outside the cell, a xylulokinase (such as Xks1) and enzyme groups of oxidative or nonoxidative pentose phosphorylation pathways (such as Zwf1, Sol3, Gnd1, Rpe1, Rki1, Tkl1 or Tal1), and examples of enhanced xylose metabolic capacity by forced expression of these enzymes, or deletion of genes, have been reported (NPL 1).

In addition, while not considered to be involved in the metabolic pathway based on metabolic maps, genes that have been reported to influence the metabolic pathway include PET18, TEC1, ARR1 (NPL 2), MNI1, RPA49 (NPL 3), YLR042C (NPL 3, NPL 4), ALP1, ISC1, RPL20B, BUD21 (NPL 5), PHO13 (NPLs 6 and 7) and FPS1 (NPL 8). In addition, PTL 2 reports a yeast with enhanced expression of acetaldehyde dehydrogenase, PTL 3 reports some xylose-assimilating yeasts with enhanced expression of one or more genes including HXT10, HXT11, HXT14, GIT1, RGT2, ARO1, ARO7, PHA2, TRP5, PYC1, PYC2 and PDA1, PTL 4 reports yeast transformed so as to overexpress formate dehydrogenase, and PTL 5 reports a yeast with loss of glycine-synthesizing protein and/or methionine-synthesizing protein gene expression, each with improved production efficiency of ethanol from xylose. These reports suggest that enzymes that are not directly found in the conversion pathway from xylose to ethanol in metabolic maps also indirectly influence conversion efficiency.

As mentioned above, in order to achieve efficient conversion from xylose to ethanol, merely the information relating to enzymes involved in the metabolic pathway from xylose to ethanol in a metabolic map is insufficient, it being also necessary to study genes and proteins that indirectly contribute to enhancing their conversion efficiency. For this purpose, the most comprehensive and effective approach may be said to be to obtain variants imparted with enhanced metabolic capacity by introduction of mutations and the use of appropriate screening methods. In a preceding project, the present inventors have made use of natural mutations and breeding techniques to successfully create yeast variants with improved xylose-assimilating properties. At the current time, however, it has not been possible to analyze which genes and which mutations of those genes are contributing to those properties.

Even when it is possible to obtain distinctive variants by natural mutations and breeding techniques, it has been necessary to sequence the entire genome of the microorganism in order to directly identify the causative genes, but the conventional Sanger method has been time-consuming and impractical. Consequently, experimental methods have been carried out for acquiring certain regions of the entire genome in which such genes are found, taking advantage of molecular biological methods and genetic methods. For example, there is a method of fragmenting variant genomic DNA, obtaining transformants exhibiting similar properties from among the transformants obtained by transfer thereof into the parent strain, and analyzing the transferred DNA. Other methods include combining different strains to discover genes in the neighborhood of the causative gene. The trouble with such methods is the extremely long times required, and difficulties often arise when recessive mutations or multiple gene mutations are involved. On the other hand, several devices have been developed in recent years, known as "next-generation sequencers", that are considerably more rapid than the conventional Sanger method. With next-generation sequencers it is possible to obtain sequence information matching entire microbial genomes, and by analyzing the entire genomes of obtained variants, it has become possible to identify causative genes. In actuality, however, with next-generation sequencing data, especially with types in which sequencing is performed in parallel on a large scale, the huge number of read nucleotide bases that are obtained as a final result are less precise on the individual nucleotide level compared to conventional Sanger sequencing, and numerous errors are included. Furthermore, since mutations are assumed to occur randomly, variant genomes presumably include very large numbers of "neutral" mutations that do not contribute to the phenotype. Consequently, in approaches where causative genes are identified by genomic analysis by a next-generation sequencer for variants, there is an essential need for 1) analysis methods that compensate for the low precision on the nucleotide base level that is characteristic of next-generation sequencers, and 2) removal of neutral mutations that are unrelated to the mutations of interest, but such methods have not yet been established.

CITATION LIST

Patent Literature

[PTL 1] Japanese Unexamined Patent Publication No. 2011-83255
[PTL 2] Japanese Unexamined Patent Publication No. 2010-239925
[PTL 3] Japanese Unexamined Patent Publication No. 2011-193788
[PTL 4] Japanese Unexamined Patent Publication No. 2011-167096
[PTL 5] Japanese Unexamined Patent Publication No. 2012-183013

Non-Patent Literature

[NPL 1] Matsushika A, Inoue H, Kodaki T, Sawayama S, "Applied Microbiology and Biotechnology", 2009, Vol. 84, p. 37-53
[NPL 2] Wahlbom C F, Cordero Otero R R, Van Zyl W H, Hahn-Hagerdal B, Jonsson L J, "Applied and Environmental Microbiology", 2003, Vol. 69, p. 740-746
[NPL 3] Bengtsson O, Jeppsson M, Sonderegger M, Parachin N S, Sauer U, Hahn-Hagerdal B, Gorwa-Grauslund M F. "Yeast", 2008, Vol. 25, p. 835-847
[NPL 4] Parachin N S, Bengtsson O, Hahn-Hagerdal B, Gorwa-Grauslund M F, "Yeast" 2010, Vol. 27, p. 741-751.
[NPL 5] Usher J, Balderas-Hernandez V, Quon P, Gold N D, Martin V J, Mahadevan R, Baetz K. "G3 (Bethesda, Md.)", 2011, Vol. 1, p. 247-258
[NPL 6] Ni H, Laplaza J M, Jeffries T W, "Applied and Environmental Microbiology", 2007, Vol. 73, p. 2061-2066
[NPL 7] Kim S R, Skerker J M, Kang W, Lesmana A, Wei N, Arkin A P, Jin Y S, "Plos One", 2013, Vol. 8, p. e57048
[NPL 8] Wei N, Xu H, Kim S R, Jin Y S, "Applied and Environmental Microbiology", 2013, Vol. 79, p. 3193

DISCLOSURE OF THE INVENTION

Problems to be Solved by the Invention

The invention of the present application provides a method for identifying causative genes for specific properties, by obtaining yeast cells that exhibit a rapid xylose consumption rate, or high proliferation potency even with high xylose concentrations of 18% and greater, using natural mutation and special culturing conditions, and then reading the genomic sequences of those variants and of isogenic line variants using a next-generation sequencer, as well as information for mutant genes and mutant proteins that impart properties related to growth or consumption in the presence of xylose, and variants having those mutant genes. In addition, it establishes a method for efficiently producing useful substances utilizing the yeast cells.

Means for Solving the Problems

As mentioned above under "Background Art", for increasing the efficiency of ethanol production from xylose it has been insufficient to merely control the genes and proteins theoretically assumed to be involved therein, based on metabolic maps and the like. Thus, obtaining mutant strains by screening of transferred mutations is a highly comprehensive and efficient approach for acquiring important genetic information.

In research and development on highly efficient transformation techniques between 2008 and 2012, as described in "Technological Research and Development for New Energies/Biomass and other energy sources" (Leading research and development/Basic research for enzyme saccharification/efficient fermentation), the present inventors created yeast variants with rapid growth in xylose-containing medium, by appropriate screening methods for natural mutations. The parent strain used for the present experiment was the heat resistant and acid resistant ethanol fermentation yeast strain NAM34-4C having excellent transformation capability, described in Japanese Unexamined Patent Publication No. 2011-83255 and deposited as FERM AP-21838 (deposited as FERM AP-21838 on Aug. 26, 2009 at the International Patent Organism Depositary (IPOD) of the National Institute of Advanced Industrial Science and Technology) (FIG. 1a shows a pedigree chart for the yeast strain created by the experiment described below). First, there was constructed strain SCA3 as an isogenic line, differing from the parent strain only in its mating type. Next, strain SCB7 was constructed, with the three genes necessary for xylose metabolism (xylose reductase gene XYL1, xylitol dehydrogenase gene XYL2 and xylulokinase XKS1) recombined in SCA3. The natural mutants with rapid growth in xylose minimal medium and enhanced xylose metabolism were then selected, the genotype being designated as HEX and the phenotype as Hex$^+$. Four variants were Hex$^+$, each by one HEX mutation, and the 4 HEX mutations could be classified as three genes $HEX1_{2-2}$, $HEX1_{2-9}$, $HEX2_{2-3}$, and $hex3_{1-5}$, the HEX1 and HEX2 mutations being dominant with respect to the wild-type allele, while the rest were recessive. The maximum specific growth rate μmax in xylose minimal medium was approximately 0.1 for the parent strain, but higher at 0.28 for the variants. The genome nucleotide sequences of the variants and their isogenic line pedigree strains were analyzed with a next-generation sequencer, the differences in nucleotide sequences were decoded, and the nucleotide sequence of the Sxm$^+$ variant described below analyzed in the same manner was used as reference, to infer the causative mutant gene. Furthermore, causative mutations among these were identified by experimentation using a double transformation method or adjacent site marker addition method. As a result, it was found that $HEX1_{2-2}$ and $HEX1_{2-9}$ were mutations in the CDC19 gene, $HEX2_{2-3}$ was a mutation in the region upstream from the GRR1 coding region (the region between the GRR1 gene start codon and the JSN1 gene stop codon adjacent to the 5' upstream end of the GRR1 gene), and $hex3_{1-5}$ was a mutation in the PHO13 gene. The Cdc19p wild type enzyme exhibits high activity by binding with fructose 1,6-bisphosphate, but mutant enzymes can retain activity even when levels of fructose 1,6-bisphosphate become low during xylose metabolism. It is therefore not the rate-determining component of metabolism from xylose to ethanol. The idea has been presented that it is possible to universally remove metabolic rate limiting in the glycolytic pathway or pentose phosphate cycle, wherein activity is regulated by post-translational modifications. Furthermore, actual examples exist which are novel means of enhancing metabolism, not depending on metabolism increase by gene expression increase or gene destruction using promoter substitution. There have as yet been no reports in regard to any CDC19 mutations or mutations in the region upstream from the GRR1 coding region, as they relate to xylose metabolism.

Furthermore, in the project referred to above, using SCB14 yeast cells with $HEX1_{2-2}$ as the parent strain, two Sxm$^+$ natural mutants were selected that were capable of growth in the presence of 180 g/L xylose, in which this strain cannot grow. The variants each had one causative gene conferring the capability of assimilating high concentration xylose ($SXM1_{32}$ and $sxm2_{33}$ genes). Also, they each had at least one SXMC gene that promotes growth. The genome nucleotide sequences of these variants and their isogenic line pedigree were analyzed with a next-generation sequencer, the differences in nucleotide sequences were decoded, and the nucleotide sequence of the Hex$^+$ variant mentioned above analyzed in the same manner was used as reference, to infer the causative mutant gene. Causative mutations among these were identified using a double transformation method or adjacent site marker addition method. As a result, $SXM1_{32}$ was found to be the MTH1 gene, and $sxm2_{33}$ was found to be the GRR1 gene. $SXM1_{32}$ is dominant with respect to the wild-type allele, while $sxm2_{33}$ is recessive. In low concentration glucose environments, the Mth1p wild type enzyme is ubiquitinated and undergoes degradation, such that it is unable to maintain Rgt1p repressor activity, but the mutant enzyme is not ubiquitinated and thus retains Mth1p enzyme activity, and Rgt1p repressor activity is preserved. Consequently, expression of Hxt1p or Hxt4p is suppressed (intracellular uptake of glucose is suppressed), and catabolite inhibition is removed. Inactivation of Grr1p obviates ubiquitination of Mth1p, and therefore Mth1p is not degraded. As a result, catabolite inhibition is naturally removed. This is thought to be the mechanism that leads to increased xylose metabolism. It was also considered that it might be linked to increased expression of enzymes involved in xylose metabolism. That is, removal of catabolite inhibition by Mth1p and Grr1p is an actual example of a novel metabolic regulating pathway linked to increased expression of xylose metabolizing enzymes. Mutations of MTH1 and GRR1 have not been reported to date.

Variants obtained utilizing the property of high proliferation potency in xylose-containing medium have been shown in experiments to also have high ethanol-producing capacity from xylose.

Other reasons for which it was possible to identify mutant genes involved in increased ethanol production from xylose according to the invention, in addition to allowing the use of genetic analysis of yeast, include that 1) mutation-inducing agents such as ethyl methanesulfonic acid were not used but rather natural mutations were utilized, so that there was no excessive introduction of mutations and identification was easier, 2) it was possible to increase the nucleotide sequence precision with next-generation sequencing, by in-house determination of the parent strain genome draft sequence, and 3) genetically similar variants and their isogenic line pedigree strains were determined by next-generation sequencing and the genomic information was handled in an integrated manner.

When it is attempted to simply obtain genomic information for a parent strain and variant by next-generation sequencing, and to utilize the differences to determine the gene mutations relating to given properties, a major obstacle is the high level of uncertainty regarding the nucleotides, due to the huge number of neutral mutations and the nature of next-generation sequencing, the target gene mutations being hidden among numerous neutral mutations and base errors, thus preventing identification of the mutations. Thus, the method of the invention, where gene mutations contributing to a phenotype are identified among numerous candidate gene mutations ("logic programming based on genetic background"), is a method in which genomic information is obtained for isogenic line pedigree strains that are genetically similar to the variants, using next-generation sequencing, and only the mutations that match the phenotype of the strain are extracted, using the phylogenetic relationship between the strains in light of that genomic information.

The four xylose metabolism-enhanced HEX variants and two high xylose metabolism-enhanced SXM variants, established by the invention, have a phylogenetic relationship (FIG. 1b). They all have the single parent strain, NAM34-4C. Furthermore, previous genetic analysis has revealed that $HEX1_{2-2}$ and $HEX1_{2-9}$ are mutations on the same or neighboring gene loci. However, HEX1 (dominant, 2 mutations), HEX2 (dominant, 1 mutation) and hex3 (recessive, 1 mutation) are completely different gene mutations. Also, SXM1 and sxm2 have $HEX1_{2-2}$ as the parent strain. Using $HEX1_{2-2}$ as an example, the responsible gene mutation that produces the $HEX1_{2-2}$ phenotype must satisfy the conditions of (1) not being present in HEX2 or hex3, and (2) being inherited by SXM1 and sxm2. Also, using $HEX2_{2-3}$ as an example, the responsible gene mutation that produces the $HEX2_{2-3}$ phenotype must satisfy the condition of not being present in the five variants other than $HEX2_{2-3}$. In conventional analysis methods, usually comparison of a pair of strains is made in a successive manner based on finite differences that can be represented by a Venn diagram, and in some cases the results are the same as logic programming if the object is a simple clade, but in cases with complex interdependencies, such a comparison is not possible and logically true results cannot be obtained.

The advantages of a logic programming method utilizing genetic background can be summarized into the following 3 points. Namely, (1) results are obtained by a single comparison, (2) there is the advantage of increased precision with a greater number of strains, regardless of dependency, and (3) in addition, identification is possible with higher precision, using strains having the same parent strain but established by different experimental systems.

All experimentation, including sequencing, involves errors. In this method, however, even when errors are present, it is possible to obtain results by the same procedure as when the experimental data are assumed to be correct. One example of analysis in consideration of such errors is a case in which the nucleotide data of the experimental groups obtained by sequencing are all correct, but the reference itself was actually in error. As a specific example, we may consider a case in which the reference data for a base at a given position is A, with 5 of 6 strains being called as T mutations and 1 strain being called as A, identically to the reference. The logical expression in this case is 111110. If the data for the 6 experimental strains are accurate, then the same mutation is thus found in 5 strains. However, in the case of 5 strains with no dependent relationship, there is a very low probability that this same mutation would occur simultaneously in 5 independent strains. If it is presumed that the particular nucleotide in the reference genome was not A, but rather T, then the logical expression becomes the exclusion set of (NOT) 111110, or 000001. In other words, this means that the mutation was actually only in the 6th strain (T→A). In most mutation analyses, such reference errors are normally not considered, and cannot even be detected in principle. That is, since if the reference is in doubt then all of the data is brought into doubt, the reference is assumed to be absolutely true. However, the reference is in fact no more than a set of data for one strain, similar to the other experimental groups. Even if the reference strain referred to by the same name as registered in the genome database was used in the experiment, such assumption is not valid unless it is verified that the genome of the strain actually used in the experiment completely matches the database. Naturally, construction of a reference genome with high precision is preferable. If the reference genome is considered to be perfectly accurate, then there no longer exist candidate mutations based on the assumption that the reference is in error.

As a separate example, one may explore the possibility that the reference is accurate but error exists in any of the data of the experimental groups. Two cases exists for data errors in the experimental groups. One is that mutations actually exist but cannot be detected as mutations, and the other is that there are really no mutations (same for the reference), but mutations have been erroneously detected. It will be readily imagined that the first is the much greater possibility. For example, if the obtained mutation result was 010000, the possibility is considered that the mutation of the first strain was not called as a mutation due to some error, and that the result was actually 110000. Similarly, it may be said that the same possibility exists for 011000, 010100, 010010 and 010001. It should be noted here that the probability is exceedingly low that the same mutation will occur at the same position in two or more independent strains. Consequently, there is basically no need to consider (combinations of) two or more errors. This case can occur when multiple instances of the same sequence exist in the genome, but may be considered to be essentially impossible in unique mapping of sequence reads obtained by next-generation sequencing (where mapping is only done for uniquely determined reads). Unique mapping is only excluded in cases where identical sequences are present at 2 locations and cannot be distinguished. However, overlapping of multiple errors and switching of the order of precedence of the mapping is one possibility that can occur. In the case of next-generation sequencers with short reads, it is difficult in principle to avoid such mismapping, and therefore they are usually ignored as unavoidable, but the possibility that this can occur must be kept in mind for obtaining accurate results.

A specific analysis method will now be described.

(1) The sequence reads obtained by next-generation sequencing are mapped with the genomic nucleotide sequence of the parent strain of the variant as the reference sequence.

(2) The mutation sites are extracted (including scaffolding, position, reference bases, mutation bases, coverage data, etc.) from the mapping data with diBayes.

(3) The P-value is calculated, indicating the reliability of each of the candidate mutations. If the number of reads called as mutations is denoted by m, the number of reads called as reference is denoted by r, the number of reads called as bases that are neither mutation nor reference bases is denoted by n, and the number of reads that were mapped but the base at that position was not called is denoted by x, then the total number of reads N mapped at that position becomes:

$$N=m+r+n+x,$$

and the net total number of reads Nnet excluding x, as actual useful data, becomes:

$$N\text{net}=m+r+n.$$

Here, the reliability of the mutation, i.e. the mutation probability Pm that the mutation actually exists, the probability Pr that the reference is accurate (the probability that it is not mutated) and the probability Pn that a mutation exists but that it is another mutation that is not of the expected form of mutation, are each given by the following respective formulas.

$$Pm=m/N\text{net}$$

$$Pr=r/N\text{net}$$

$$Pn=n/N\text{net}$$

The P-values are calculated for all of the data obtained in (2).

Here, since there are only 3 possibilities for a nucleotide other than the reference, Pm=0.25 and Pr=0.25 represent random mutations.

(4) A logical expression (matrix) is constructed, where 1 is the case in which the causative mutation for each strain from the genetic line for each strain should be present in the other strains, and 0 is the case where they should not.

(5) Among the candidate mutations obtained in (2) for each strain, individuals having the same form of mutation at the same position are probed for each strain in light of (4) above, and a list is made of the candidate mutations which are mutations whose combination of presence/absence are sufficient as candidate mutations for the strains, i.e. whose presence/absence of mutation in all of the strains are not logically contradictory (Level 1).

(6) Similar to (4) above, a logical expression is constructed on the assumption that the reference is in error, and a separate list is made of the possible candidate mutations for that case (Level 2).

(7) Also, a logical expression is constructed for the hypothesis that any one of the data for each strain compared is in error, and a separate list is made of the possible candidate mutations for that case (Level 3).

(8) With the candidate mutation lists obtained in (5) to (7) above, the genes (coding regions) in which the mutation (position and mutation form) is present, and its positional information, or when it is between genes, the upstream and downstream genes and their relative positional information, and the predicted amino acid mutations, etc. are obtained by referring to genome annotation information for the parent strain. Since multiple annotations may be given for the same position depending on the precision of the annotation, the candidate list obtained here will sometimes be larger than those of (5) to (7). Also, one of the gene names may not be given for the ends of the chromosome or scaffold, when it is between genes.

(9) The gene list created in (7) is classified as group A=high reliability (Pm≥0.8), group B=medium reliability (0.8>Pm≥0.6), group C=low reliability (0.6>Pm≥0.4), or essentially unreliable (Pm<0.4), based on the P-value obtained in (3) above. In the case of SOLiD, it is known that data of ≤0.6 is unreliable when is empirically sufficient coverage (sequence read length ×3), but when another sequencer is used, it is necessary to vary the threshold value of reliability according to the sequencer precision and anticipated level of mutations. The value may also vary depending on the cover number.

(10) Lists are made for each of groups A, B and C, at each Level 1, 2 and 3.

(11) Based on the results of identification of the candidates as described above, Level 1/Group A is used as the most likely candidate and the mutation is transferred into the yeast parent strain to verify the phenotype. Furthermore, when none is found in Level 1/Group A, it is verified whether or not the mutation that produces the phenotype is in Level 1/Group B, as well as Level 2/Group A, Level 2/Group B, Level 3/Group A, Level 3/Group B, in that order.

The present inventors developed a method for increasing the precision of causative gene candidates from the huge amounts of data produced by next-generation sequencers, and thus completed this invention.

Specifically, the present invention provides the following.

[1]

A recombinant or non-recombinant xylose-assimilating yeast having a gene coding for Mth1p and/or Grr1p, wherein:

the Mth1p is either
(a1) a protein consisting of the amino acid sequence represented by SEQ ID NO: 7 in which the alanine at position 81 has been substituted by another amino acid; or
(a2) a protein consisting of the amino acid sequence of (a1) in which one or more amino acids have been deleted, substituted or added at a position other than the amino acid at position 81, and the Grr1p is either
(b1) a protein consisting of the amino acid sequence represented by SEQ ID NO: 8 in which the cysteine at position 632 has been substituted by another amino acid; or
(b2) a protein consisting of the amino acid sequence of the protein of (b1) in which one or more amino acids have been deleted, substituted or added at a position other than the amino acid at position 632.

[2]

The yeast according to [1], wherein the alanine at position 81 of SEQ ID NO: 7 is substituted by aspartic acid.

[3]

The yeast according to [1] or [2], wherein the cysteine at position 632 of SEQ ID NO: 8 is substituted by tyrosine.

[4]

The recombinant or non-recombinant xylose-assimilating yeast according to any one of [1] to [3], further having a gene coding for Cdc19p and/or an upstream region of the GRR1 coding region, wherein:

the Cdc19p is either
(c1) a protein consisting of the amino acid sequence represented by SEQ ID NO: 5 in which the proline at position 272 and/or the alanine at position 344 are substituted by another amino acid; or
(c2) a protein consisting of the amino acid sequence of the protein of (c1) in which one or more amino acids are deleted, substituted or added at a position other than the amino acid at position 272 and/or 344, and the upstream region of the GRR1 coding region is either
(d1) an upstream region having the nucleotide sequence represented by SEQ ID NO: 6 in which the nucleotide at position −333 has been substituted by a nucleotide other than adenine; or
(d2) an upstream region comprising the nucleotide sequence of (d1) in which one or more nucleotides have been deleted, substituted or added at a position other than the nucleotide at position −333.

[5]

The yeast according to [4], wherein the proline at position 272 of SEQ ID NO: 5 is substituted by threonine.

[6]

The yeast according to [4] or [5], wherein the alanine at position 344 of SEQ ID NO: 5 is substituted by proline.

[7]

The yeast according to any one of [4] to [6], wherein the adenine at position −333 of SEQ ID NO: 6 is substituted by thymine.

[8]

The yeast according to any one of [1] to [7], wherein the gene coding for xylose isomerase, xylose reductase, xylitol dehydrogenase and/or xylulokinase is overexpressed.

[9]

The yeast according to any one of [1] to [8], wherein the yeast is selected from the group consisting of *Saccharomyces, Kluveromyces, Candida, Pichia, Schizosaccharomyces* and *Hansenula*.

[10]

The yeast according to [9], wherein the yeast is *Saccharomyces*.

[11]

The yeast according to any one of [1] to [10], which is capable of growth in the presence of xylose at a high concentration of 180 g/L or greater.

[12]

A recombinant or non-recombinant xylose-assimilating yeast having a gene coding for Cdc19p and/or an upstream region of the GRR1 coding region, wherein:
the Cdc19p is either
(c1) a protein consisting of the amino acid sequence represented by SEQ ID NO: 5 in which the proline at position 272 and/or the alanine at position 344 are substituted by another amino acid; or
(c2) a protein consisting of the amino acid sequence of the protein of (c1) in which one or more amino acids are deleted, substituted or added at a position other than the amino acid at position 272 and/or 344, and
the upstream region of the GRR1 coding region is either
(d1) an upstream region having the nucleotide sequence represented by SEQ ID NO: 6 in which the nucleotide at position −333 has been substituted by a nucleotide other than adenine; or
(d2) an upstream region comprising the nucleotide sequence of (d1) in which one or more nucleotides have been deleted, substituted or added at a position other than the nucleotide at position −333.

[13]

The yeast according to [12], wherein the proline at position 272 of SEQ ID NO: 5 is substituted by threonine.

[14]

The yeast according to [12] or [13], wherein the alanine at position 344 of SEQ ID NO: 5 is substituted by proline.

[15]

The yeast according to any one of [12] to [14], wherein the adenine at position −333 of SEQ ID NO: 6 is substituted by thymine.

[16]

The yeast with deposit number NITE BP-01675 (SCB39), deposited at the NITE Patent Microorganisms Depositary.

[17]

The yeast with deposit number NITE BP-01676 (SCB40), deposited at the NITE Patent Microorganisms Depositary.

[18]

The yeast with deposit number NITE BP-01672 (SCB14), deposited at the NITE Patent Microorganisms Depositary.

[19]

The yeast with deposit number NITE BP-01674 (SCB16), deposited at the NITE Patent Microorganisms Depositary.

[20]

The yeast with deposit number NITE BP-01673 (SCB15), deposited at the NITE Patent Microorganisms Depositary.

[21]

A method for producing a useful substance using the yeast according to any one of [1] to [20] in the presence of xylose, wherein the useful substance is one or more substances selected from the group consisting of ethanol, lactic acid, acetic acid, propanol, isobutanol, butanol, succinic acid and glycerol.

[22]

The method according to [21], wherein the useful substance is ethanol.

[23]

A method in which a microorganism having a specific metabolic property is obtained by natural or artificial mutation in one or multiple stages, the full genomic sequence of a variant of the isogenic line pedigree is determined, mutations acquired by the strain are extracted by mapping to a reference genome, the state of gene mutations (independent and inherited) inferred from the genetic background and phenotype between variants in the isogenic line pedigree is converted to a logical expression by Boolean logic, and by probing for and verifying mutation combinations that are logically true based on the logical expression, considering the case in which the obtained data is reliable, the case in which the reference sequence is in error and/or the case in which a portion of the obtained data is erroneous, the causative gene for the metabolic property and/or gene mutations are determined from among multiple candidate mutations obtained by full genomic analysis.

[24]

The method according to [23], wherein the microorganism is a yeast.

[25]

The method according to [23], wherein the yeast is *Saccharomyces*.

Effect of the Invention

By using a microorganism bred according to the invention, or a microorganism created in the same manner, it is possible to increase production of useful substances, such as ethanol from xylose.

According to the invention there are provided microorganisms with excellent xylose metabolic capacity. In addition, by utilizing a mutant gene or mutant protein discovered by the present invention, it is possible to create a microorganism having excellent xylose metabolic capacity, using gene recombinant technology or the like. In addition, by using a microorganism of the invention or a microorganism having a gene mutation discovered by the present invention, it is possible to efficiently produce a useful substance such as ethanol, utilizing xylose-containing medium.

In addition, by reading the genomic sequences of the variant and isogenic line pedigree variants using a next-generation sequencer, it is possible to identify the causative gene responsible for the property.

BRIEF DESCRIPTION OF THE DRAWINGS

FIG. 1 is a pedigree chart representing isolation and identification of xylose metabolism-enhanced natural mutants. (a) A tree diagram for HEX variants, and (b) a tree diagram for HEX variants and SXM variants used in analysis of logic programming based on genetic background.

FIG. 6 shows an experiment design for analysis of hex3$_{1\text{-}5}$ mutation gene as PHO13. (a) Construction of strain pho13Δ. The kanMX region was amplified by a pair of primers and recombined into the yeast chromosome. (b) Recessive mutation pho13Δ. Since a gene product is not produced, it is recessive with respect to the wild-type allele. (c) Complementarity test. A complementarity test using a diploid obtained by cross-breeding hex3$_{1\text{-}5}$ and pho13Δ.

FIG. 8 shows an experiment design for analysis of HEX1$_{2\text{-}2}$ as a CDC19 gene mutation. First, the structure surrounding the CDC19 gene is analyzed against the *Saccharomyces* genome database (http://www.yeastgenome.org/) (FIG. 8a). Next, kanMX is transferred into the flanking region of CDC19 by a transformation method. It is confirmed if the transformants retain the properties of Hex$^+$ (FIG. 8b). If Hex$^+$ is retained, then PCR amplification is carried out from the CDC19 to kanMX genes. The DNA is used for transformation, and it is examined whether kanMX and Hex$^+$ are simultaneously transformed. If they are simultaneously transformed, the HEX1 gene can be shown to be the CDC19 gene.

In FIG. 17b, the glucose concentrations are indicated with dashed lines, and the xylose concentrations are indicated by solid lines.

FIG. 18 shows a method of identifying an SXM1 mutation. The gene structure neighboring MTH1 was analyzed from public strains in the yeast genome database (http://www.yeastgenome.org/) and from draft genomic analysis of strain NAM34-4C. In addition, it was assumed that the location of insertion of the kanMX gene would hardly affect the gene structure of MTH1 and neighboring genes.

EMBODIMENTS OF THE INVENTION

Figure 2:
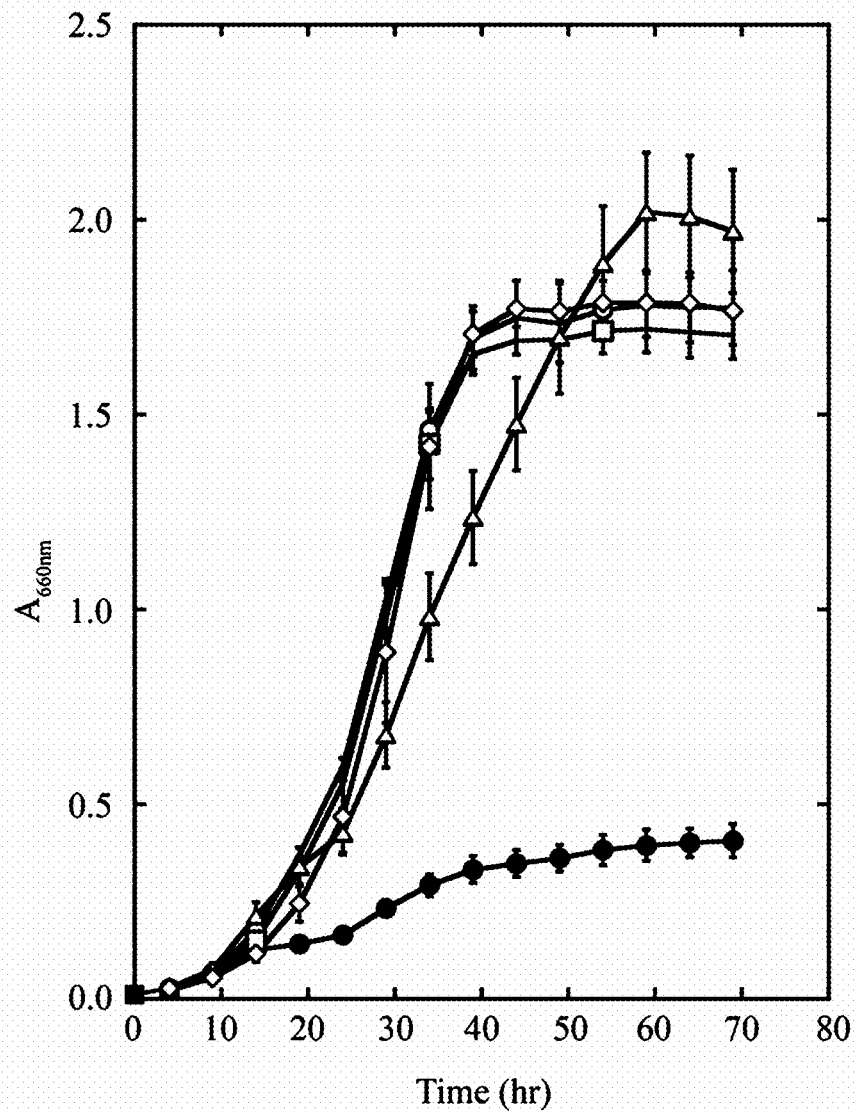
FIG. 2 shows growth of xylose-assimilating *S. cerevisiae* SCB4, SCB5, SCB6 and SCB7, and the parent strain SCA3, in xylose medium. The 5 strains were grown in 5 mL of uracil-containing xylose minimal medium (xylose concentration: 20 g/L). The test cells were inoculated into 5 mL of uracil-containing xylose minimal medium (MSXU, pH 5.5), and shake cultured at 35° C. The cell concentration was measured using a biophotorecorder. The data are mean values and standard deviations for three experiments. Symbols: ○=SCB4; △=SCB5; □=SCB6; ◇=SCB7; ●=SCA3.

The present invention relates to microorganisms with one or more genes selected from the group consisting of CDC19, GRR1 and MTH1, having a mutation, and/or the upstream region of the GRR1 coding region having a mutation, and to the use thereof. The invention further relates to a technique for determining the genomic sequence of a variant created by mutation and of its isogenic line pedigree, with a next-generation sequencer, and identifying gene mutations conferring the variant properties by comparative genomic analysis.

CDC19 codes for pyruvate kinase. Pyruvate kinase is a catalyst that reacts to produce pyruvic acid from phosphoenol-pyruvate in the glycolytic pathway, and it is one of the enzymes in the metabolic pathway of production of ethanol from xylose, but there has as yet been no report that mutations in CDC19 can increase production of ethanol from xylose. However, it has been reported that phosphoenol-pyruvate, which is the substrate of pyruvate kinase, accumulates upon glucose depletion, and this is believed to be due to inactivation of pyruvate kinase triggered by glucose depletion. Normally, when ligneous or other materials containing a mixture of glucose and xylose are used, glucose is consumed preferentially even if the yeast has incorporated the gene group necessary for xylose metabolism. Xylose metabolism mainly takes place after glucose has been consumed, and since pyruvate kinase is an enzyme present in the conversion pathway from xylose to ethanol, reduction in pyruvate kinase activity is assumed to act in an underproductive manner on conversion from xylose to ethanol. It is thought that mutations in CDC19 discovered by the present invention do not cause such reduction in pyruvate kinase activity by glucose depletion. By using a microorganism bred according to the invention, with an increased xylose consumption rate and increased productivity from xylose to ethanol, using the mutated CDC19, or a microorganism created in the same manner, it is possible to increase production of useful substances, such as ethanol from xylose.

A mutation was discovered by the invention in the region upstream from the GRR1 coding region in one of the natural mutants with enhanced xylose metabolism. Grr1p is a protein present in the SCF ubiquitin ligase complex, and it is involved in functional control of Mth1p (described hereunder). As explained below, Mth1p is an important factor in catabolite suppression. Thus, mutations in the upstream region of the GRR1 coding region are thought to have effects on GRR1 expression level, thereby affecting catabolite suppression via Mth1p regulation, and thus resulting in enhanced xylose metabolism. The mutation in the upstream region of the GRR1 coding region discovered by the present invention is thought to elicit an effect of increasing the xylose consumption rate by countering catabolite suppression, and therefore using a microorganism bred according to the invention or a microorganism created in the same manner, it is possible to increase production of useful substances such as ethanol from xylose.

In addition, it was found that MTH1 and GRR1 mutations according to the invention promote growth of recombinant yeast in the presence of high-concentration xylose. For the purpose of the invention, "in the presence of high-concentration xylose" means, generally, a concentration such that conventional xylose-assimilating yeast cannot grow and survive. Specifically, this is a xylose concentration of 180 g/L or greater, preferably 190 g/L or greater and most preferably 200 g/L or greater. Mth1p is a protein that interacts with the glucose sensors Snf3p and Rgt2p, and transcription factor Rgt1, and it is involved in regulating catabolite suppression. Specifically, it is known to be involved in regulation of expression of the hexose transporter (HXT gene group) in response to glucose concentration in culture solution. Grr1p is a protein that regulates the function of Mth1p described above, by decomposition via ubiquitination. Thus, the GRR1 and MTH1 mutations discovered by the present invention alter catabolite suppression by quantitatively or functionally altering Mth1p, thereby presumably enhancing xylose metabolism. The MTH1 and GRR1 mutations discovered by the present invention are thought to elicit an effect of increasing the xylose consumption rate by countering catabolite suppression, and therefore using a microorganism bred according to the invention or a microorganism created in the same manner, it is possible to increase production of useful substances such as ethanol from xylose.

These CDC19, GRR1, MTH1, and GRR1 coding region upstream region mutations have not hitherto been reported to have effects on production of ethanol from xylose, and this is new knowledge that has first been demonstrated by the present invention, by screening of natural mutations and variants and genomic analysis with next-generation sequencers. In addition, phenotypes that grow in xylose-containing medium and exhibit high growth in high-concentration xylose-containing medium promote efficient ethanol production from xylose via rapid growth of the yeast in xylose-containing medium. Furthermore, as mentioned above, these mutations are thought to restrict catabolite suppression, having a positive effect on uptake and metabolism of xylose in the co-presence of glucose, and therefore promoting efficient ethanol production from xylose.

The mutant proteins and genes coding for them may be of the microorganisms themselves, or so long as they are functional they may be derived from other organisms. In addition, information relating to these budding yeast genes and genes having similar functions in other organisms can be found by sequence analysis in databases such as that of the NCBI, based on BLAST, with the gene names or budding yeast gene amino acid sequences or nucleotide sequences as keys. The genes may be genome-derived or cDNA.

Mutated Cdc19p, Mth1p or Grr1p proteins and genes coding for them may have one or more amino acid or nucleotide deletions, substitutions or additions in addition to the disclosed mutations, so long as the functionality is similar. In addition, as mutant proteins and genes coding for them, genes coding for amino acid sequences having, with respect to the disclosed amino acid sequences, at least 70% identity, at least 80% identity, at least 85% identity, at least 90% identity, at least 95% identity, at least 96% identity, at least 97% identity, at least 98% identity or at least 99% identity, and still exhibiting growth in the disclosed xylose-containing medium, are also encompassed within the scope of the invention. Furthermore, as genes coding for these mutant proteins, genes that hybridize with DNA comprising nucleotide sequences complementary to the disclosed nucleotide sequences under stringent conditions, are also encompassed within the scope of the invention. Stringent conditions are well-known in the relevant field, and being sequence-dependent they differ depending on various conditions, but for example, they include rinsing conditions where rinsing is carried out in 2×SSC and 0.5% SDS for 5 minutes, in 2×SSC and 0.1% SDS for 15 minutes, in 0.1×SSC and 0.5% SDS at 37° C. for 30 to 60 minutes, and then in 0.1×SSC and 0.5% SDS at 68° C. for 30 to 60 minutes, at a temperature Tm of below 12° C. to 20° C., calculated for the hybrids.

Similarly, for the upstream region of the GRR1 coding region, one or more nucleotide deletions, substitutions or additions in addition to the disclosed mutations may be present, so long as the functionality is similar. In addition, sequences exhibiting with respect to the disclosed nucleotide sequences, at least 70% identity, at least 80% identity, at least 85% identity, at least 90% identity, at least 95% identity, at least 96% identity, at least 97% identity, at least 98% identity or at least 99% identity, where the yeast still have the upstream region of the GRR1 coding region including the mutation and exhibiting growth in the disclosed xylose-containing medium, are also encompassed within the scope of the invention. Furthermore, sequences of the upstream region of the GRR1 coding region that hybridize with the disclosed nucleotide sequences under stringent conditions are also encompassed within the scope of the invention.

Such genes or upstream regions can be obtained using Polymerase Chain Reaction (PCR) with primers designed by reference to the disclosed sequence or a sequence obtained from a database such as that of the NCBI, with suitable DNA as template. The mutations can be transferred using Error-prone PCR, or various mutagenic methods.

The promoters regulating expression of the mutant genes are not limited to endogenous ones. That is, other promoters such as glyceraldehyde-3-phosphate dehydrogenase (TDH3) may be used. In addition, the promoters and mutant genes may be transferred into yeast in the form of plasmids, or they may be incorporated into the genomic DNA. They may also replace the original gene in the genomic DNA. Also, there is no limit to the number of copies, whether for insertion into plasmids or the genome. For a recessive gene, it is necessary to delete the original gene or to render it non-functional.

The yeast of the invention may be modified with genes other than those mentioned above, or unmodified, so long as the functionality is the same. Genes from other organisms may also be introduced.

Furthermore, the step of conversion from xylose to xylulose, as the initial process of xylose metabolism, may be with xylose reductase (XR) and xylitol dehydrogenase (XDH) or with xylose isomerase (XI), (XI) and genes from other organisms may also be used. In addition, these genes may be introduced as plasmids or they may be inserted into a chromosome. The number of copies is not restricted.

For creation of the yeast, there are no restrictions on the type of recombinant vector or the transformation method.

So long as it includes xylose, the culture solution may contain other carbon sources, and it is not limited in its constituent components so long as the yeast grow in it.

When a useful substance is to be produced, a culture solution containing at least xylose may be used for the production using yeast of the invention. In this case, the yeast may have, in addition to a mutant gene as disclosed by the invention, also another introduced gene that is suited for production of the useful substance, or a mutant gene. Useful substances are not particularly restricted and include ethanol, lactic acid, acetic acid, propanol, isobutanol, butanol, succinic acid and glycerol. Ethanol is particularly preferred to be obtained as the useful substance. Such substances may be substances produced in yeast by reaction of the metabolic enzymes originally in the yeast, or substances that can be produced by introducing genes of enzymes necessary for their production into the yeast by gene recombinant technology, and more efficient production is possible by appropriately adjusting the expression levels of the enzymes with reference to a metabolic map. In research for production of such substances, a medium containing glucose as the carbon source is usually used to produce the substances, and by applying the results of the invention to such conventional technology it is possible to using xylose-containing carbon sources for production of these useful substances. That is, the results of the invention can be utilized not only for production of bioethanol but also for production of starting materials for various chemical products.

Yeast include *Saccharomyces, Kluveromyces, Candida, Pichia, Schizosaccharomyces* and *Hansenula*. *Saccharomyces* yeast are particularly preferred, examples of which include *Saccharomyces cerevisiae, Saccharomyces bayanus* and *Saccharomyces boulardii*.

The manner of the culturing method is not restricted so long as the yeast grow in xylose-containing culture solution. The culture solution may be a pretreatment solution or saccharified solution containing xylose, obtained by treating a natural substance such as ligneous matter, or it may be an artificial preparation of xylose and other substances. It may also be a solution obtained by adding chemical substances to a solution obtained by treatment of a natural substance. The culturing conditions are not limited in terms of temperature, pH, aerated conditions, stirring speed, culturing time and the like, so long as the yeast grow and metabolize xylose to produce the useful substance. There are also no restrictions on the methods for controlling these conditions. In addition, there are no restrictions on whether or not pretreatment and saccharification treatment are used, or on whether fermentation is conducted simultaneously with saccharification treatment.

Purifying treatment of the useful substance after fermentation is also not restricted. A suitable method may be used, according to the type of useful substance.

The advantages of a "logic programming method utilizing genetic background" according to the invention can be summarized into the following 3 points. Namely, (1) results are obtained by a single comparison, (2) there is the advantage of increased precision with a greater number of strains, regardless of dependency, and (3) in addition, identification is possible with higher precision using strains having the same parent strain but established by different experimental systems (histories).

Identification by "logic programming in consideration of genetic background" can be utilized by preparing the following type of experimental environment. Firstly, all of the variants to be compared should be derived from the same parent strain. Secondly, the full genomic nucleotide sequence of the parent strain should be constructed with high precision. Thirdly, the genetic information (initiation and termination sites, orientation, gene names, etc.) of the genomic nucleotide sequence should be maintained. Also, if possible, the number of mutant gene loci producing a phenotype is preferably specified.

The "logic programming in consideration of genetic background" according to the invention does not depend on the type of microorganism. Furthermore, it can be used regardless of the method of mutation transfer or the dominant/recessive character of the mutation. If a sequence corresponding to the full genome can be determined, there is no restriction on the sequencing principle or whether or not the method requires a reference, or on the type of sequencing device, but it is preferred to use a next-generation sequencer. The term "next-generation sequencer" is used in contrast to "first-generation sequencer", which is a fluorescent capillary sequencer utilizing the Sanger method, and it refers to an apparatus for determining massively parallel nucleotide sequences by comprehensively analyzing several tens to several thousand by read length fragments against several tens of millions to several 100 million DNA fragments, using sequential DNA synthesis with DNA polymerase or DNA ligase. In a next-generation sequencer, a different sequencing principle is used than in a first-generation sequencer using the Sanger method that halts extension by DNA polymerase using dideoxynucleotides. The principles used include synthetic sequencing, pyrosequencing and ligase reaction sequencing. Various next-generation sequencers have been provided to date by many businesses and research institutions, examples including HiSeq2500 (Illumina, Inc.), MiSeq (Illumina, Inc.), 5500×1 SOLiD™ (Life Technologies), Ion Proton™ (Life Technologies), Ion PGM™ (Life Technologies) and GS FLX+ (Roche), and the next-generation sequencers that may be used for the invention are not limited to these. By using a next-generation sequencer it is possible to accomplish sequence analysis of larger genome regions in a very short period of time. However, in analysis using next-generation sequencers, the final result is a huge number of decoded bases and the precision is low on the individual base level compared to Sanger sequencing, with inclusion of numerous errors, and therefore the present invention compensates for this by obtaining genomic information for the isogenic line pedigree that is genetically similar to the variant using a next-generation sequencer or the like, and then looking at the phylogenetic relationship between them in light of the genomic information, to extract only mutations that match the phenotype of the strain, as described above.

When it is attempted to produce a useful substance such as ethanol utilizing various types of biomass, a microorganism bred according to the invention, or a microorganism created in the same manner, may be used to drastically increase production of useful substances, such as ethanol from xylose. This is particularly effective when using starting materials with high hemicellulose content, and when using a method of producing a high xylose concentration in pretreatment of the starting material. According to the invention there are provided microorganisms with excellent xylose metabolic capacity. In addition, by utilizing a gene mutation discovered by the present invention, it is possible to create a microorganism having excellent xylose metabolic capacity, using gene recombinant technology or the like. In addition, by using a microorganism of the invention or a microorganism having a gene mutation discovered by the present invention, it is possible to efficiently produce a useful substance such as ethanol utilizing xylose-containing medium. A method may then be used to read the genomic sequences of that variant and isogenic line pedigree variants using a next-generation sequencer according to the invention, and to identify the causative gene responsible for the property.

The present invention will now be explained in greater detail, with the understanding that these examples are in no way limitative on the invention.

Examples

Strains, Plasmids and Oligonucleotide Primers Used

The strains and plasmids used are listed in Table 1. Strains NAM201 and NAM203 are G418-resistant transformants of NAM34-4C (FERM AP-21838) by 1 and 2 amplicon DNA, listed in Table 1, and they are denoted by Ura$^-$ and Leu$^-$, respectively. NAM34-4CG2 is a haploid strain, being an ascospore clone produced from a forced zygote diploid of NAM201 and NAM203. NAM300 is a G418-resistant transformant by DNA of amplicon 3 shown in Table 1, as a diploid produced by mating the mating-transformed transformant with the original strain. Strains SCA1 and SCA2 are haploid strains obtained from NAM300, and are MATa and MATα, respectively. SCA3 is a strain obtained by removing the kanMX region from SCA1. The strain was constructed by a series of procedures involving (i) transformation of SCA1 using plasmid pZeo, (ii) excision of the kanMX region by Cre protein expression, and (iii) removal of plasmid pZeo. The primers (Genenet, Fukuoka, Japan) were designed based on Primer 3 (http://frodo.wi.mit.edu/primer3/). The nucleotide sequences for *S. cerevisiae* genes were based on information from the *Saccharomyces* Genome Database (http://www.yeastgenome.org/).

TABLE 1

Yeast and plasmids used in experiment (1)

| Bacterial Strain | Genotype or phenotype | Reference, source or derivation |
|---|---|---|
| *Saccharomyces cerevisiae* | | |
| NAM34-4C | MATa | |
| NAM201 | MATa ura3Δ::kanMX | Tfm (NAM34-4C: kanMX DNA, G418-r)[a] |
| NAM203 | MATa leu2Δ::kanMX | Tfm (NAM34-4C: kanMX DNA, G418-r) |
| NAM34-4C G2 | MATa | Haploid (NAM201 × NAM203)[b] |
| NAM300 | MATa/MATα pho87Δ::kanMX | Tfm (NAM34-4CG2: pho87::kanMX DNA, G418-r) |
| SCA1 | MATa pho87Δ::kanMX | a haploid strain obtained from the tetrads which was constructed from the NAM300 diploid |
| SCA2 | MATα | a haploid strain obtained from the tetrads which was constructed from the NAM300 diploid |
| SCA3 | MATa pho87Δ | SCA1 with the deletion of the kanMX region |
| SH6703 | MATα sed1::Sh ble eqf3::HIS3 | YGRS[c] |
| SCB4 | MATa pho87Δ ura3Δ::XM$_2$[d] | Tfm (SCA3: XM$^d$ DNA, G418-r) |
| SCB5 | MATa pho87Δ ura3Δ::XM$_3$[e] | Tfm (SCA3: XM DNA, G418-r) |
| SCB6 | MATa pho87Δ ura3Δ::XM$_7$[d] | Tfm (SCA3: XM DNA, G418-r) |
| SCB7 | MATa pho87Δ ura3Δ::XM$_8$[d] | Tfm (SCA3: XM DNA, G418-r) |
| SCB103-10D | MATα ura3Δ::XM$_8$ | Haploid (SCB11-8C × SCB102-3D) |
| SCB13 | MATa pho87Δ ura3Δ::XM$_8$ hex3$_{1-3}$ | Spontaneously isolated hex1-5 mutant obtained from SCB7 |
| SCB14 | MATa pho87Δ ura3Δ::XM$_8$ HEX1$_{2-2}$ | Spontaneously isolated HEX2-2 mutant obtained from SCB7 |
| SCB15 | MATa pho87Δ ura3Δ::XM$_8$ HEX2$_{2-3}$ | Spontaneously isolated HEX2-3 mutant obtained from SCB7 |
| SCB16 | MATa pho87Δ ura3Δ::XM$_8$ HEX1$_{2-9}$ | Spontaneously isolated HEX2-9 mutant obtained from SCB7 |
| SCB104 | MATa pho87Δ ura3Δ::XM$_8$ hex3$_{1-5}$/MATα ura3Δ::XM$_8$ | Diploid (SCB13 × SCB103-10D)[f] |
| SCB105 | MATa pho87Δ ura3Δ::XM$_8$ HEX1$_{2-2}$/MATα ura3Δ::XM$_8$ | Diploid (SCB14 × SCB103-10D) |
| SCB105-3A | MATa ura3Δ::XM$_8$ HEX1$_{2-2}$ | Haploid (SCB14 × SCB103-10D) |
| SCB106 | MATa pho87Δ ura3::XM$_8$ HEX2$_{2-3}$/MATα ura3Δ::XM$_8$ | Diploid (SCB15 × SCB103-10D) |

TABLE 1-continued

Yeast and plasmids used in experiment (1)

| Bacterial Strain | Genotype or phenotype | Reference, source or derivation |
|---|---|---|
| SCB106-8D | MATa pho87Δ ura3Δ::XM$_8$ HEX2$_{2-3}$ | Haploid (SCB15 × SCB103-10D) |
| SCB107 | MATa pho87Δ ura3Δ::XM$_8$ HEX1$_{2-9}$/ MATα ura3Δ::XM$_8$ | Diploid (SCB16 × SCB103-10D) |
| SCB107-8D | MATa ura3Δ::XM$_8$ HEX1$_{2-9}$ | Haploid (SCB16 × SCB103-10D) |
| SCB108 | MATa pho87Δ ura3Δ::XM$_8$ hex3$_{1-5}$/ MATα ura3::XM$_8$ hex3$_{1-5}$ | Diploid (SCB104-7B × SCB104-5D) |
| SCB109 | MATa pho87Δ ura3Δ::XM8 HEX1$_{2-2}$/ MATα ura3Δ::XM$_8$ HEX1$_{2-2}$ | Diploid (SCB105-3B × SCB105-3A) |
| SCB110 | MATa pho87Δ ura3Δ::XM$_8$ HEX1$_{2-3}$/ MATα ura3Δ::XM$_8$ HEX2$_{2-3}$ | Diploid (SCB106-8D × SCB106-1D) |
| SCB111 | MATa pho87Δ ura3Δ::XM$_8$ HEX1$_{2-9}$/ MATα ura3Δ::XM$_8$ HEX1$_{2-9}$ | Diploid (SCB107-5C × SCB107-8D) |
| SCB112 | MATa pho87Δ ura3Δ::XM$_8$/MATα ura3Δ::XM$_8$ | Diploid (SCB103-5B × SCB103-10D) |
| SCB113 | MATa pho87Δ ura3Δ::XM$_8$ HEX1$_{2-9}$/ MATα ura3Δ::XM$_8$ HEX1$_{2-2}$ | Diploid (SCB107-8D × SCB105-3A) |
| SCB114 | MATa pho87Δ ura3Δ::XM$_8$ HEX2$_{2-3}$/ MATα ura3Δ::XM$_8$ HEX1$_{2-2}$ | Diploid (SCB106-8D × SCB105-3A) |
| SCB115 | MATa pho87Δ ura3Δ::XM$_8$ hex3$_{1-5}$/ MATα ura3Δ::XM$_8$ HEX1$_{2-2}$ | Diploid (SCB104-7B × SCB105-3A) |
| SCB116 | MATa pho87Δ ura3::XM$_8$ hex3$_{1-5}$/ MATα ura3Δ::XM$_8$ HEX2$_{2-3}$ | Diploid (SCB104-7B × SCB106-1D) |
| SCB38 | MATa pho87Δ URA3::XM$_8$ HEX1$_{2-2}$ | Tfm (SCB14: URA+ DNA, URA+, G418-s) |
| SCC2-11B | MATa pho87Δ URA3Δ::XM$_8$ | Haploid (SCB38 × SCB103-10D) |
| SCB44 | MATa pho87Δ URA3::XM$_8$ TAL1::kanMX-P$_{TDH3}$-TAL1 | Tfm (SCC2-11B: kanMX DNA, G418-r) |
| SCB45 | MATa pho87Δ URA3:XM$_8$ pho13Δ::kanMX | Tfm (SCC2-11B: kanMX DNA, G418-r) |
| SCB47 | MATa pho87Δ URA3::XM$_8$ TAL1::kanMX-P$_{TDH3}$-TAL1/MATα pho87Δura3Δ::XM$_8$ HEX1$_{2-2}$ | Diploid (SCB44 × SCB105-7A) |
| SCB48 | MATa pho87Δ URA3::XM$_8$ TAL1::kanMX-P$_{TDH3}$-TAL1/MATα pho87Δura3Δ::XM$_8$ HEX1$_{2-3}$ | Diploid (SCB44 × SCB106-1D) |
| SCB49 | MATa pho87Δ URA3:.XM$_8$ pho13Δ::kanMX/MATα pho87Δura3Δ::XM8 hex3$_{1-5}$ | Diploid (SCB45 × SCB104-2B) |
| SCB52 | MATa ura3Δ1::kanMX ade2-101 his3Δ200 trpΔ1 lys2 met14 | Tfm (SCB2: kanMX DNA, G418-r) |
| SCB53 | MATa pho87Δ URA3::XM$_8$ pho13Δ::kanMX/MATα URA3::XM$_8$ pho13Δ::kanMX | Diploid (SCB45 × SCB52-1B) |
| SCC12 | MATa pho87Δ ade1Δ1-kanMX URA3::XM$_8$ | Tfm (SCC2-11B: Δ1-kanMXDNA, G418-r) |
| SCC24 | MATa pho87Δ URA3::XM$_8$ GRR1 | Tfm (SCC12: ADE$^+$ DNA, GRR1 DNA ADE$^+$, G418-s) |

*Escherichia coli*

| | | |
|---|---|---|
| DH10B | F-mcrA Δ(mrr-hsdRMS mcrBC) Φ80 lacZΔM15 ΔlacX74 recA1 endA1 araD139 Δ(ara leu)7697 galU galK λ- rpsL nupG) | Life technologies, |

Plasmid and amplicon DNA

| | | |
|---|---|---|
| pBlu-LTKTL-TDH3 | loxP-P$_{TEF}$-kanMX-T$_{TEF}$-loxP-P$_{TDH3}$ | |
| pS-LTKTL-MATa | pho87'-loxP-P$_{TEF}$-kanMX-T$_{TEF}$-loxP-MATa locus (SH6703) | pS-LIKTL-MATa |
| pKX1X2XKS | loxP-P$_{TEF}$-kanMX-T$_{TEF}$-loxP-P$_{TDH3}$-XYL1-T$_{TDH3}$-P$_{TDH3}$-XYL2-T$_{TDH3}$-P$_{TDH3}$-XKS1-T$_{TDH3}$ | pKX1X2XKS |
| pZeo | CEN6/ARSH4 URA3 P$_{GAL1}$ CRE TER$_{CTC1}$ bla ori$_{pUC}$ p$_{IEF}$, EM7 ZEOCIN TER$_{CTC1}$ | pZeo |
| amplicon 1 | ura3'-loxP-P$_{TEF}$-kanMX-T$_{TEF}$-loxP-'ura3 | amplicon 1 |
| amplicon 2 | leu2'-loxP-P$_{TEF}$-kanMX-T$_{TEF}$-loxP-'leu2 | |

TABLE 1-continued

Yeast and plasmids used in experiment (1)

| Bacterial Strain | Genotype or phenotype | Reference, source or derivation |
|---|---|---|
| amplicon 3 | pho87'-loxP-$P_{TEF}$-kanMX-$T_{TEF}$-loxP-BUD5-MATa-'taf2 | |
| $XM_8$ | loxP-$P_{TEF}$-kanMX-$T_{TEF}$-loxP-$P_{TDH3}$-XYL1-$T_{TDH3}$-$P_{TDH3}$-XYL2-$T_{TDH3}$-$P_{TDH3}$-XKS1-$T_{TDH3}$ | |
| $XM_3$ | loxP-$P_{TEF}$-kanMX-$T_{TEF}$-loxP-$P_{TDH3}$-XYL1-$T_{TDH3}$-$P_{TDH3}$-XYL2-$T_{TDH3}$ | | a. Tfm, transformation: Tfm (NAM34-4C: kanMX DNA, G418-r) indicates G418 transformant of NAM34-4C using kanMX DNA. Has a 40 bp sequence homologous with the DNA region to be substituted into the flanking region of kanMX DNA.
b. Haploid (NAM201×NAM203) indicates one of the 4 spores obtained by cross-breeding NAM201 and NAM203.
c. YGRS, Yeast Genetic Resource Center.
d. XM, $XM_2$, $XM_7$, $XM_8$ are DNA fragments having the gene structure loxP-$P_{TEF}$-kanMX-$T_{TEF}$-loxP-$P_{TDH3}$-XYL1-$T_{TDH3}$-$P_{TDH3}$-XYL2-$T_{TDH3}$-$P_{TDH3}$-XKS1-$T_{TDH3}$, which includes the loxP and TEF promoters, the kanMX gene, the TEF terminator, the loxP and TDH3 promoters and the TDH3 terminator.
e. $XM_3$ is DNA having the gene structure loxP-$P_{TEF}$-kanMX-$T_{TEF}$-loxP-$P_{TDH3}$-XYL1-$T_{TDH3}$-$P_{TDH3}$-XYL2-$T_{TDH3}$.
f. Diploid (SCB13×SCB103-10D) indicates a diploid obtained by cross-breeding SCB13 and SCB103-10D.

Culture Media

The YPD medium used as yeast growth medium was prepared containing 20 g glucose, 10 g Bacto Yeast Extract and 20 g Bacto Peptone per 1 L of distilled water, and adjusted to pH 5.5. MS medium was prepared containing 1.7 g Yeast nitrogen base and 5 g $(NH_4)_2SO_4$ per 1 L of distilled water, and adjusted to pH 5.5. MSD medium contained 20 g glucose in 1 L of MS medium. MSX medium contained 20 g xylose in 1 L of MS medium. To the media there were added as necessary, 50 mg/L adenine (Ade), 50 mg/L uracil (Ura) and 40 mg/L amino acids, as final concentrations. Antibiotics were also added as necessary. For G418 disulfate (G418) (Nacalai Tesque, Japan), addition was to a final concentration of 362 mg/L, and for Zeocin (Life Technologies, Japan), addition was to a final concentration of 100 mg/L. For solid medium, agar was added at 20 g per 1 L of medium. SpoKI spore-forming medium contained 10 g of potassium acetate per 1 L of distilled water, and was adjusted to pH 5.5 with addition of 20 g of agar. Luria-Bertani (LB) medium used as the *E. coli* growth medium contained 10 g of bactotryptone, 5 g of Bacto Yeast Extract and 10 g of NaCl per 1 L of distilled water, and was adjusted to pH 7.2. For solid medium, agar was added at 15 g per 1 L of medium. Thiamine was added as a vitamin, as necessary, to a final concentration of 5 mg/L. The antibiotics ampicillin (Amp) and kanamycin (Km) were added as necessary, to final concentrations of 50 μg/mL. M9 medium used for preparation of competent *E. coli* was prepared containing 6.0 g $Na_2HPO_4$, 3.0 g $KH_2PO_4$, 0.5 g sodium chloride, 2 mL 1 M $MgSO_4$, 10 mL 20% glucose and 0.1 mL 1 M $CaCl_2$ per 1 L of distilled water, and adjusted to pH 7.5.

YPX18 medium was medium with addition of 180 g/L xylose instead of the glucose of YPD medium.

Spore-Forming Method and Assay Method

Stationary culturing was conducted on YPD solid medium at 30° C. for 1 day. The grown test yeast cell colonies were transferred to spore-forming medium using a sterilized toothpick. Stationary culturing was conducted at 30° C. for 2-3 days, forming spores.

A sample was taken with a sterilized toothpick and suspended in 5 μL of sterilized water placed on a glass slide. Spore formation was observed using an optical microscope (300×, objective lens×20, eyepiece lens×10, intermediate variable magnification×1.5, BH2 Optical Microscope by Olympus Corp.), and the spore formation was assayed.

Mass Mating Method

The test yeast cells were inoculated into 2 mL of YPD liquid medium with a sterilized platinum wire. Yeast cells of known mating type were inoculated into the same medium with a sterilized platinum wire. The mixed 2 mL of YPD suspension was subjected to stationary culturing overnight at 30° C.

Zygote Assessment

The mass mated cells were taken and placed on a glass slide. Cover glass was placed over it and observation was conducted with an optical microscope. Mating was judged to have occurred if cells with a typical irregular form appeared.

Isolation of Individual Yeast Cells Using Micromanipulator.

The test cells were inoculated into YPD solid medium and stationary cultured at 30° C. for 1 day. The produced colonies were suspended in 2 mL of YPD liquid medium, and plated on 20 mL of YPD solid medium with a flame-sterilized platinum loop. Next, a micromanipulator (Singer MSM System 200 by Singer Instruments, Roadwater, Watchet, Somerset TA23 0RE, UK) was used to separate out the nearly oval-shaped single cells as typical diploid yeast, under a microscope. These were stationary cultured at 30° C. for 2 days, and grown colonies were obtained from the single cells.

Dissection of Ascospores

The cells on the spore-forming medium were suspended in 75 μL of 0.015 M potassium phosphate buffer at pH 7.5 containing Zymolyase 20, to a final concentration of 300 μg/mL, and incubated at 30° C. for 20 minutes. Next, the spore suspension was taken with a sterilization platinum loop and transferred onto YPD solid medium. Four spores were dissected, one spore at a time, using a micromanipulator, and then stationary culturing was carried out at 30° C. for 2 to 3 days.

DNA Extraction, PCR, Transformation and Nucleotide Sequencing

*E. coli* plasmid DNA extraction was carried out using a High Pure Plasmid Isolation Kit (product of Roche Diagnostics, Tokyo, Japan), according to the manufacturer's protocol. The yeast cell DNA extraction was carried out using a Gen Torukun™ (for yeast) High Recovery (by Takara Bio, Inc., Japan), according to the manufacturer's protocol. PCR reaction was carried out using KOD FX (Toyobo, Japan). To the reaction reagent there was added 2×PCR buffer for KOD FX, 2 mM dNTPs, Template DNA (4 ng), primer (2.5 pmol) and KOD FX DNA Polymerase (1.0 U/µL) (total: 50 µL). After light spin-down, it was set in a thermal cycler kept at 94° C. The PCR reaction time was varied according to the amplification fragment size. For amplification of 1 kb fragments, the amplification was with a cycle of 94° C. for 15 seconds, 54° C. for 30 seconds and 68° C. for 1 minute repeated 30 times, followed by incubation at 68° C. for 5 minutes.

Transformation of *E. coli* was accomplished by the following method, using electroporation. *E. coli* DH10B cultured cells ($Abs_{600nm}$=0.5 to 0.8) were rinsed with 1 mM HEPES buffer and then suspended in 10% glycerol to prepare competent cells. The DNA was transferred using a Gene Pulser Xcell Electroporation System (2, 500 V, Gap: 0.2 cm, 25 µF, 200Ω). The yeast transformation was accomplished using the lithium acetate method.

The nucleotide sequencing was carried out using an Applied Biosystems 3130 Genetic Analyzer and a BigDye® Terminator v3.1 Cycle Sequencing Kit.

Analysis of Cell Proliferation Using Biophotorecorder

The test strain cultured overnight at 30° C. on YPD solid medium was inoculated into 10 mL of YPD medium, and shake cultured at 30° C. for 24 hours (120 rpm, reciprocal shaking/min). The cells were centrifuged at 4° C., 2400×g for 1 minute, collected, and suspended in sterilized water. The cell suspension was inoculated into 5 mL of MSD medium (5-mL volume L-shaped test tube), to an initial concentration of $Abs_{660nm}$=0.014. The cell concentration was automatically recorded with a biophotorecorder (TVS062CA: Advantec Toyo Kaisha, Tokyo), and the generation time was analyzed.

Construction of *S. cerevisiae* with Xylose-Assimilating Genes XYL1, XYL2 and XKS1

The section of pKX1X2XKS from the kanMX region to the XKS1 region was amplified using the pair of primers R-GAPDHt (URA+SacII) (SEQ ID NO: 1) and F-LTKTL (URA+ApaI) (SEQ ID NO: 2). Next, the amplified DNA was used to select G418-resistant transformants of strain SCA3. Since the two primers have homologous regions of the ura3 gene, the G418-resistant transformants exhibit uracil requirement.

Removal of kanMX Marker by Cre Expression

A strain having the cre-expressing plasmid pZeo transferred by a transformation method was separated out as a Zeocin-resistant transformant. Next, the test cells were inoculated into 5 mL of YPDAU+Zeo medium with a platinum wire, and shake cultured at 30° C. for about 16 hours. The $Abs_{600nm}$ of the culture solution was measured, and if the turbidity was 1 or greater, 4 mL of the culture solution was centrifuged at 3500×g for 1 minute. The supernatant was discarded and mixing was performed with a vortex mixer. The mixture was then suspended in 4 mL of sterilized water. The procedure was repeated twice for rinsing. The rinsed cells were suspended in 1 mL of sterilized water, and 100 µL thereof was inoculated into 5 mL of YPGalAU medium and cultured at 30° C. for 1 hour. A 4 mL portion of the culture solution was centrifuged at 3500×g for 1 minute. The supernatant was discarded and mixing was performed with a vortex mixer. The mixture was then suspended in 4 mL of sterilized water. This was repeated twice for rinsing. The suspension was appropriately diluted and smeared onto YPDAU plate medium. If colonies could be confirmed, 50 each were transferred to YPDAU, YPDAU+G418 and YPDAU+Zeo plate medium, and G418-sensitive strains were selected. For removal of the plasmids, the selected strains were inoculated into 5 mL of YPDAU medium with a platinum wire, and shake cultured at 30° C. for about 16 hours. The culture solution was appropriately diluted and smeared onto YPDAU medium. If colonies could be confirmed, 50 each were transferred to YPDAU and YPDAU+Zeo plate medium, and Zeocin-sensitive strains were selected.

Isolation of Variants Exhibiting High-Efficiency Xylose Assimilation (1)

Strain SCB7 was subjected to reciprocal shake culturing (120 rpm) on 10 mL of YPD medium at 30° C. for 24 hours, and after centrifuging at 2400×g, 4° C. for 1 minute, it was suspended in sterilized water. The cell suspension was inoculated into 5 mL of uracil-containing MSX medium in a 5-mL L-shaped test tube to an initial concentration of $Abs_{660nm}$=0.014, and growth was analyzed with a biophotorecorder. Upon rapid increase in turbidity, the suspension was smeared onto MSX solid medium and cultured at 30° C. for 2-3 days. The large colonies were selected and transferred to YPD medium. If necessary, single cells were isolated with a micromanipulator (Singer MSM Systems Series 400, Minerva Tech., K.K., Tokyo, Japan). In order to confirm their nature as mutants, cell proliferation was analyzed with a biophotorecorder. For isolation of the independent mutants, one variant was isolated from an independent L-shaped test tube.

Batch Fermentation Test (1)

The test cells cultured overnight at 30° C. on YPD solid medium were inoculated into 50 mL of YPD medium (pH 4.0), and subjected to reciprocal shake culturing at 30° C. for 24 hours (120 rpm). Next, the cell suspension was inoculated into 50 mL of YPX3 medium to an initial concentration of $Abs_{660nm}$=1.0, and shake cultured at 35° C. for 48 hours. In order to determine the ethanol and glucose concentrations in the fermentation medium, centrifugal separation was performed at 4° C. and 20, 400×g for 5 minutes and the supernatant was obtained.

Analysis of Glucose, Xylose and Ethanol Concentrations

The glucose, xylose and ethanol concentrations in the supernatant were measured using a BF7M 4-channel biosensor (Oji Scientific Instruments, Hyogo, Japan) equipped with a BF30ASX automatic sampler, hydrogen peroxide electrode and two-dimensional detection system. The biosensor enzymes used were glucose oxidase (E. C. 1. 1. 3. 4) for glucose, pyranose oxidase (E. C. 1. 1. 3. 10) for xylose and alcohol oxidase (E. C. 1. 1. 3. 13) for ethanol. The hydrogen peroxide generated during the reaction was electrolyzed with a platinum electrode, and the change in voltage produced during that time was measured with a detection system. The ethanol yield (%) was defined as the ratio (%) of the produced ethanol concentration (g/L) and the theoretical maximum ethanol concentration (g/L) {0.51×initial glucose concentration (g/L)}.

TABLE 2

Yeast and plasmids used in experiment (2)

| Bacterial Strain | Genotype or phenotype | Reference, source or derivation |
|---|---|---|
| *Saccharomyces cerevisiae* | | |
| SCB38 | MATa pho87Δ URA3::XM$_8$HEX1$_{2-2}$ | Tfm (SCB14: URA+ DNA, URA+, G418-s) |
| SCB105-7A | MATα ura3::XM$_8$HEX1$_{2-2}$ | Haploid (SCB14 × SCB103-10D) |
| SCB32 | MATa SXM1 SXMC1 pho87Δ ura3::XM$_8$HEX1$_{2-2}$ | Spontaneously isolated SXM mutant obtained from SCB14 |
| SCB33 | MATa SXM2 pho87Δ ura3::XM$_8$HEX1$_{2-2}$ | Spontaneously isolated SXM mutant obtained from SCB14 |
| SCB39 | MATa SXM1 SXMC1 pho87Δ URA3::XM$_8$HEX1$_{2-2}$ | Tfm (SCB32: URA+ DNA, URA+, G418-s) |
| SCB40 | MATa SXM2 pho87Δ URA3::XM$_8$HEX1$_{2-2}$ | Tfm (SCB33: URA+ DNA, URA+, G418-s) |
| SCB42 | MATa SXM1 SXMC1 pho87Δ URA3::XM$_8$ HEX1$_{2-2}$/ MATα HEX$_{2-2}$ ura3::XM$_8$ | Diploid: (SCB39 × SCB105-3A) |
| SCB43 | MATa SXM2 pho87Δ URA3::XM$_8$HEX1$_{2-2}$/ MATα HEX$_{2-2}$ ura3::XM$_8$ | Diploid: (SCB40 × SCB105-7A) |
| SCC21 | MATa pho87Δ ade1Δ1::kanMX URA3::XM$_8$HEX1$_{2-2}$ | Tfm (SCB38: Δ1-kanMXDNA, G418-r) |
| SCC22 | MATa SXM1::kanMX SXMC1 pho87Δ URA3::XM$_8$HEX1$_{2-2}$ | Tfm (SCB39: kanMXDNA, G418-r) |
| SCC23 | MATa pho87Δ URA3::XM$_8$HEX1$_{2-2}$ SXM1::kanMX | Tfm (SCB38: kanMXDNA, G418-r) |
| SCC25 | MATa pho87Δ URA2::XM$_8$HEX1$_{2-2}$ SXM2 | Tfm (SCC21: ADE+ DNA, SXM2 DNA ADE+, G418-s) |
| SCC60 | MATa SXMC1 HEX1$_{2-2}$ura3::XM$_8$/MATa SXM1 SXMC1 pho87Δ URA3::XM$_8$ HEX1$_{2-2}$ | Diploid (SCB42-3B × SCB42-4D) |
| SCC61 | MATa SXM1 pho87Δ URA3::XM$_8$ HEX1$_{2-2}$/MATa SXM1 SXMC1 pho87Δ URA3::XM$_8$HEX1$_{2-2}$ | Diploid (SCB42-3C × SCB42-4D) |
| SCB38-MTH1$_{32}$ | MATa pho87Δ URA3::XM$_8$HEX1$_{2-2}$ MTH1$_{32}$ | Tfm (SCB38: プラスミド DNA, G418-r) |
| SCC2-11B-MTH1$_{32}$ | MATa pho87Δ URA3::XM$_8$MTH1$_{32}$ | Tfm (SCC2-11B: kanMXDNA, G418-r) |
| grrl$_{33}$/+ | MATa pho87Δ URA3::XM$_8$ HEX1$_{2-2}$ grrl/MATa pho87Δ URA3::XM$_8$HEX1$_{2-2}$ | Diploid (SCC25 × SCB41-2B) |
| Plasmid | | |
| p-Δ1-kan | ura3'-Δ1-loxP-P$_{TEF}$-kanMX-T$_{TEF}$-loxP-'ura3 | |
| pADE1 | ADE1 (NAM34-4C) | |
| pGRR1 | HEX2$_{2-3}$ | |

*Symbols the same as in Table 1.

Isolation of Variants Exhibiting High-Efficiency Xylose Assimilation (2)

Strain SCB14 was subjected to reciprocal shake culturing (120 rpm) on 10 mL of YPD medium at 30° C. for 24 hours, and after centrifuging at 2400×g, 4° C. for 1 minute, it was suspended in sterilized water. The cell suspension was inoculated into 5 mL of uracil-containing YPX18 medium in a 5-mL L-shaped test tube to an initial concentration of Abs$_{660nm}$=0.014, and growth was analyzed with a biophotorecorder. Upon rapid increase in turbidity, the suspension was smeared onto YPX18 solid medium and cultured at 30° C. for 2-3 days. The large colonies were selected and transferred to YPD medium. If necessary, single cells were isolated with a micromanipulator (Singer MSM Systems Series 400, Minerva Tech., K.K., Tokyo, Japan). In order to confirm their nature as mutants, cell proliferation was analyzed with a biophotorecorder. For isolation of the independent mutants, one variant was isolated from an independent L-shaped test tube.

Batch Fermentation Test (2)

The test cells cultured overnight at 30° C. on YPD solid medium were inoculated into 50 mL of YPD medium (pH 4.0), and subjected to reciprocal shake culturing at 30° C. for 24 hours (120 rpm). Next, the cell suspension was inoculated into 50 mL of YPX5 medium or YPD6X3 medium to an initial concentration of Abs$_{660nm}$=1.0 or 20, and shake cultured at 35° C. for 48 hours. In order to determine the ethanol and glucose concentrations in the fermentation medium, centrifugal separation was performed at 4° C. and 20, 400×g for 5 minutes and the supernatant was obtained.

Construction of Isogenic Line from *S. cerevisiae* NAM34-4C

An isogenic line of NAM34-4C was constructed. Strain NAM201 was created by transformation with ura3Δ:kanMX DNA and strain NAM203 was created by transformation with leu2Δ:kanMX DNA (Table 1), and a diploid was constructed by their forced mass mating. The ascospores were analyzed, and while the MATa-type strain could not be isolated, strain NAM34-4CG (MATα) having enhanced mating ability over NAM34-4C was isolated (Table 1). MATa strain SCA1 was constructed by transformation with the SH6703-derived MATa region DNA of strain NAM34-4CG. Strain SCA3 was then constructed, having kanMX removed, which had been used for the selection (Table 1). Strain SCA2 was selected as a MATα strain excellent for genetic analysis.

Construction of Xylose-Assimilating Isogenic Line Strains

A strain capable of metabolizing xylose to xylulose-5-phosphate was isolated as a G418-resistant transformant, by transformation of SCA3 with amplicon DNA created using plasmid pKX1X2XKS as template (ura3'-loxP-kanMX-loxP-$P_{TDH3}$-XYL1-$T_{TDH3}$-$P_{TDH3}$-XYL2-$T_{TDH3}$-$P_{TDH3}$-XKS1-$T_{TDH3}$-'ura3). A growth test for the transformants was conducted in uracil-added xylose minimal medium (MSXU, pH 5.5, xylose concentration: 20 g/L) at a temperature of 35° C., and 4 strains were grown (FIG. 2). These were designated as strains SCB4, SCB5, SCB6 and SCB7.

The shortest generation time (Gshort) for SCB7 was 5 hours. Upon analyzing the gene structure of xylose-assimilatable SCB7, the desired structure loxP-$P_{TEF}$-kanMX-$T_{TEF}$-$P_{TDH3}$-XYL1-$T_{TDH3}$-$P_{TDH3}$-XYL2-$T_{TDH3}$-$P_{TDH3}$-XKS1-$T_{TDH3}$ was confirmed by PCR analysis and nucleotide sequence analysis.

Isolation of Variants Exhibiting High-Efficiency Xylose Assimilation (Hex$^+$ Variants).

Figure 3:
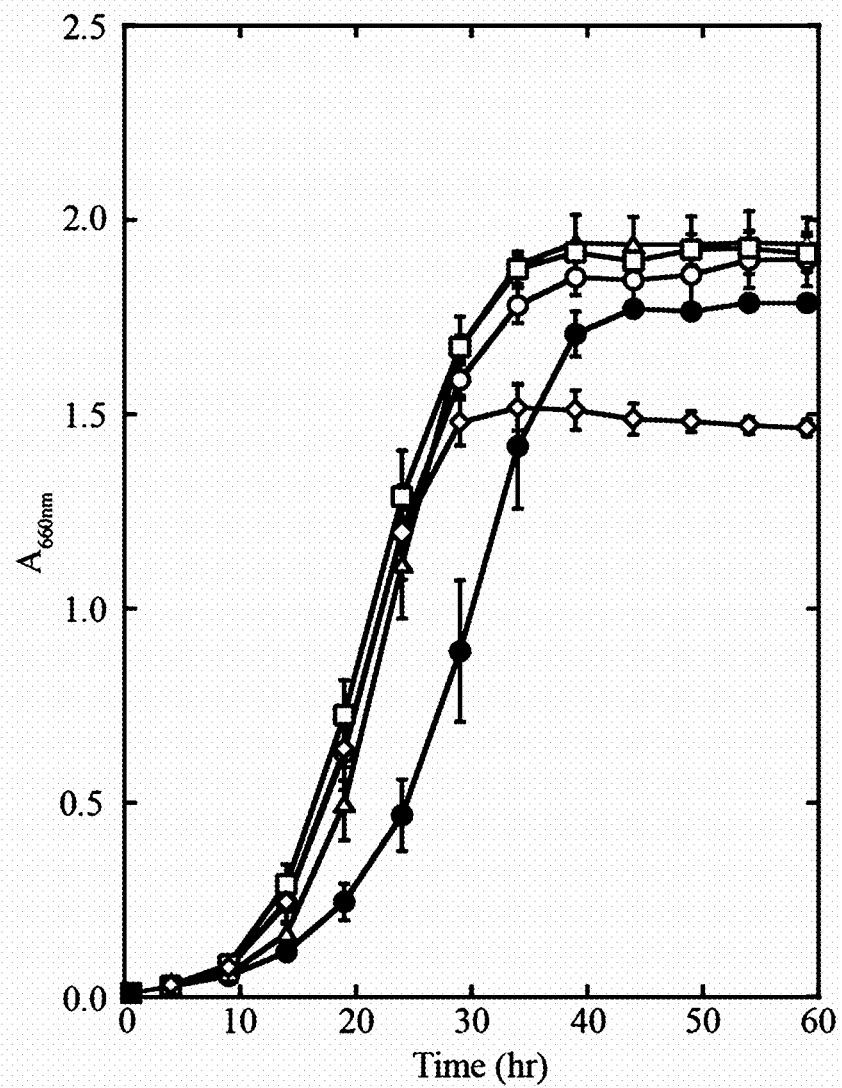
FIG. 3 shows growth of *S. cerevisiae* Hex$^+$ mutants (SCB13, SCB14, SCB15, SCB16) and the parent strain SCB7 in xylose medium. The test cells were inoculated into 5 mL of uracil-containing xylose minimal medium (MSXU, pH 5.5, xylose concentration: 20 g/L), and shake cultured at 35° C. The cell concentration was measured using a biophotorecorder. The data are mean values and standard deviations for three experiments. Symbols: ○=Hex$^+_{1\text{-}5}$ SCB13; △=Hex$^+_{2\text{-}2}$ SCB14; □=Hex$^+_{2\text{-}3}$ SCB15; ◇=Hex$^+_{2\text{-}9}$ SCB16; ●=Hex$^-$ SCB7.

Natural mutants were isolated exhibiting faster growth than the shortest generation time for SCB7. Specifically, shake culturing of strain SCB7 was carried out on MSUX medium (pH 5.5) at 35° C., and 4 independent mutants exhibiting rapid growth were isolated. After isolation of single cells, growth of the mutants was examined on xylose minimal medium (xylose concentration: 20 g/L) and compared with the parent strain SCB7 (FIG. 3). The 4 mutants exhibited essentially the same growth rate. The Gshort for SCB14 was 2.5 hours, which was half of the value of Gshort=5 hours for the parent strain SCB7. The gene conferring high-efficiency xylose assimilation was named {high efficiency of xylose assimilation (HEX) mutation}, and the mutant phenotype was named Hex$^+$.

Genetic Analysis of Hex$^+$-Conferring Mutations

Figure 4:
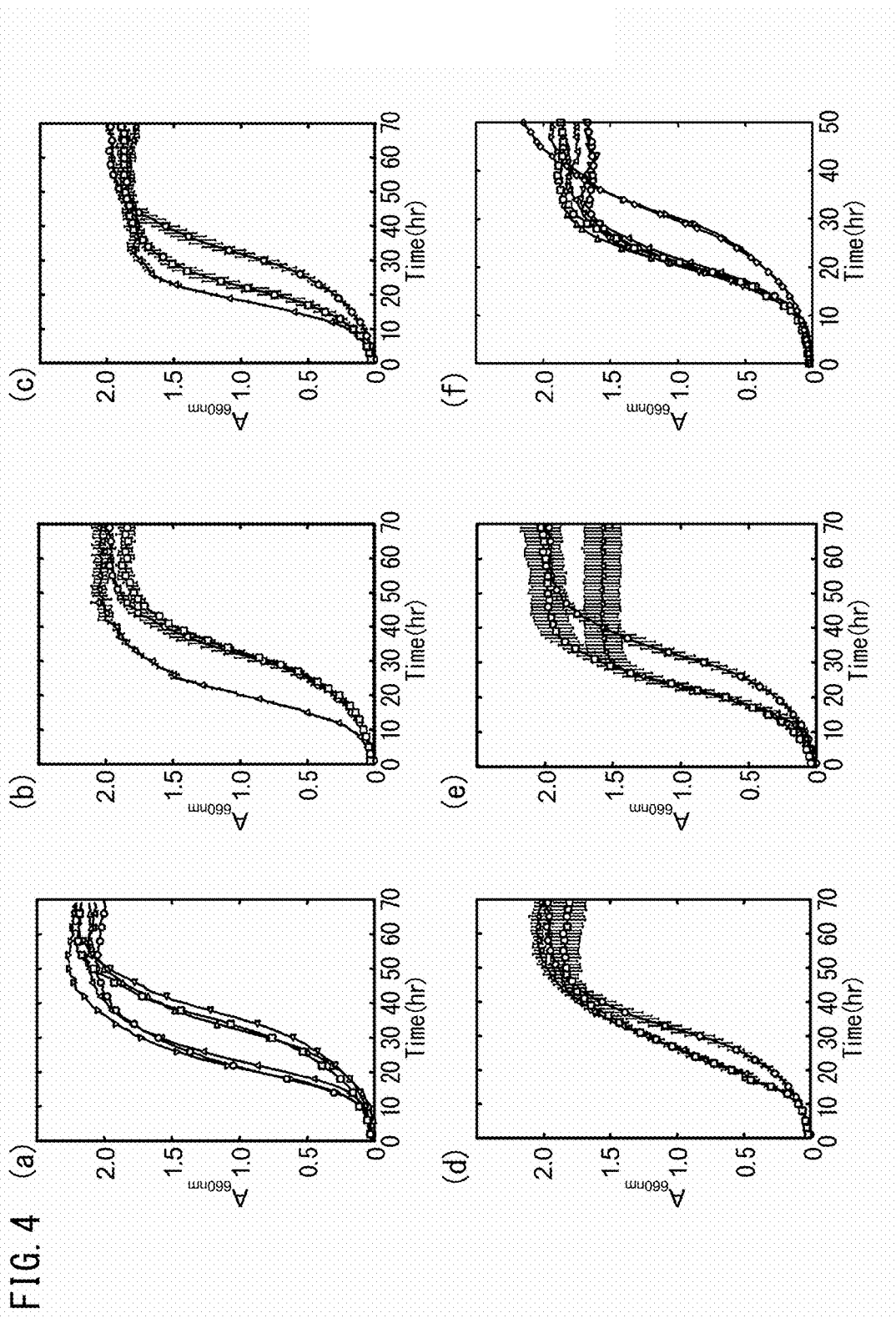
FIG. 4 shows experimental results using genetic analysis of *S. cerevisiae* Hex$^+$ mutants (SCB13, SCB14, SCB15, SCB16). The test cells were inoculated into 5 mL of xylose minimal medium (MSXU, pH 5.5, xylose concentration: 20 g/L), and shake cultured at 35° C. The cell concentration was measured using a biophotorecorder. (a) Analysis of four Hex$^+$ variants. Analysis was made of 4 spore clones obtained by cross-breeding a Hex$^+_{2\text{-}2}$ variant (SCB14) and the wild type Hex$^-$ (SCB103-10D), and of the parent strain. Symbols: ○=SCB14; □=SCB103-10D; and for the 4 spore clones: △=SCB105-5A; ▽=SCB105-5B, right-pointing △=SCB105-5C; left-pointing △=SCB105-5D. (b) to (e): Dominant/recessive test with respect to wild type, for HEX$_{1\text{-}5}$ (b), HEX$_{2\text{-}2}$ (c), HEX$_{2\text{-}3}$ (d) and HEX$_{2\text{-}9}$ (e). Symbols: ○=Hex$^-$/Hex$^-$ diploid (SCB112); △=Hex$^+$/Hex$^+$ diploid (SCB108, SCB109, SCB110 and SCB111); □=Hex$^+$/Hex$^-$ diploid (SCB104, SCB105, SCB106 and SCB107). (f) Linkage analysis. Analysis was made of the HEX$_{2\text{-}2}$ variant SCB105-3A, the HEX$_{2\text{-}3}$ variant SCB106-8D, the wild type SCB103-10D and 4 spore clones SCB114-5A, -5B, -5C and -5D obtained by cross-breeding HEX$_{2\text{-}2}$ and HEX$_{2\text{-}3}$. Symbols: ○=SCB105-3A; □=SCB106-8D; ◇=SCB103-10D; and for the 4 spore clones: △=SCB114-5A; ▽=SCB114-5B, right-pointing △=SCB114-5C; left-pointing △=SCB114-5D. The data are mean values and standard deviations for three measurements.

Genetic analysis of mutations conferring the Hex$^+$ phenotype was carried out in the following manner. (i) Determination of number of mutations in the 4 variants; (ii) dominant/recessive test of mutations with respect to wild-type allele; (iii) linkage analysis between mutant genes. First, the number of mutations in SCB14 were analyzed. The Hex$^+$ strain SCB14 (MATa pho87Δ ura3Δ:XM$_8$ HEX$_{2-2}$) and the wild-type strain Hex$^-$ SCB103-10D (MATα ura3Δ:XM$_8$) were cross-bred to create a hetero diploid, and spores were formed. In 24 examined asci, all of the spores were isolated as Hex$^+$:Hex$^-$=2:2. The typical growth pattern in MSUX medium (pH 5.5, xylose concentration: 20 g/L) at 35° C. is shown in FIG. 4a. The results for cross-breeding of the remaining Hex$^+$ strains (SCB13, SCB15, SCB16) and the wild-type strain SCB103-10D also showed isolation with Hex$^+$:Hex$^-$=2:2. The number of asci examined were 30 asci, 24 asci and 30 asci for SCB13, SCB15 and SCB16, respectively. These results indicate that the mutants were the Hex$^+$ phenotype by a single genetic mutation each.

In order to analyze whether or not the 4 Hex$^+$-conferring mutations were dominant with respect to the wild-type allele, diploids obtained by cross-breeding the Hex$^+$ variants (SCB13, SCB14, SCB15, SCB16) and the Hex$^-$ wild-type strain SCB103-10D were analyzed on MSUX medium (pH 5.5, xylose concentration: 20 g/L) at 35° C. The Hex$_{1-5}^+$/Hex$^-$ diploid SCB104 obtained by cross-breeding the Hex$_{1-5}^+$ strain SCB13 and the Hex$^-$ strain SCB103-10D exhibited the same growth as the Hex$^-$/Hex$^-$ wild-type diploid SCB112 (FIG. 4b). That is, the HEX$_{1-5}$ mutation was recessive with respect to the wild-type allele. The remaining 3 diploids exhibited faster growth similar to the Hex$^+$ variants (FIG. 4c, d, e). Thus, the mutations in the 3 variants SCB14, SCB15 and SCB16 were dominant with respect to the wild-type allele. The 3 mutations were defined as HEX$_{2-2}$, HEX$_{2-3}$ and HEX$_{2-9}$, respectively.

In order to examine the linkage relationship between the HEX$_{1-5}$, HEX$_{2-2}$, HEX$_{2-3}$ and HEX$_{2-9}$ mutations, all possible cross-breedings were carried out between the variants (HEX$_{2-2}$×HEX$_{2-9}$, HEX$_{2-2}$×HEX$_{2-3}$, HEX$_{2-2}$×HEX$_{1-5}$, HEX$_{1-5}$×HEX$_{2-3}$). Spores were formed of the diploid SCB113 obtained by cross-breeding the HEX$_{2-2}$ variant SCB105-3A and the HEX$_{2-9}$ variant SCB107-8D. Four spores of the 16 asci examined were all isolated with Hex$^+$:Hex$^-$=4+:0−. As a result of spore formation of the other diploids obtained by cross-breeding (HEX$_{2-2}$×HEX$_{2-3}$, SCB114; HEX$_{2-2}$×HEX$_{1-5}$, SCB115; HEX$_{1-5}$×HEX$_{2-3}$, SCB116), they were isolated with Hex$^+$:Hex$^-$=4+:0−, 3+:1− and 2+:2−. The number of asci examined were 11 asci for SCB114, 8 asci for SCB115 and 8 asci for SCB116, the 4+:0−, 3+:1− and 2+:2− isolation ratios being 2:8:1, 3:4:1 and 2:4:2, respectively. FIG. 4f shows a typical growth pattern for 4 spores of SCB114 isolated with 3+:1− on MSUX medium (pH 5.5) at 35° C.

These results strongly suggest that the HEX$_{1-5}$, HEX$_{2-2}$ and HEX$_{2-3}$ mutations were different genes that were mutually unlinked, and the HEX$_{2-2}$ and that HEX$_{2-9}$ mutations were located in the same vicinity and were the same gene. The HEX$_{2-2}$ or HEX$_{2-9}$ mutant genes were named HEX1, the HEX$_{2-3}$ mutant gene was named HEX2, and the HEX$_{1-5}$ mutant gene was named hex3.

Batch Fermentation Test for Hex$^+$ Variants

Figure 5:
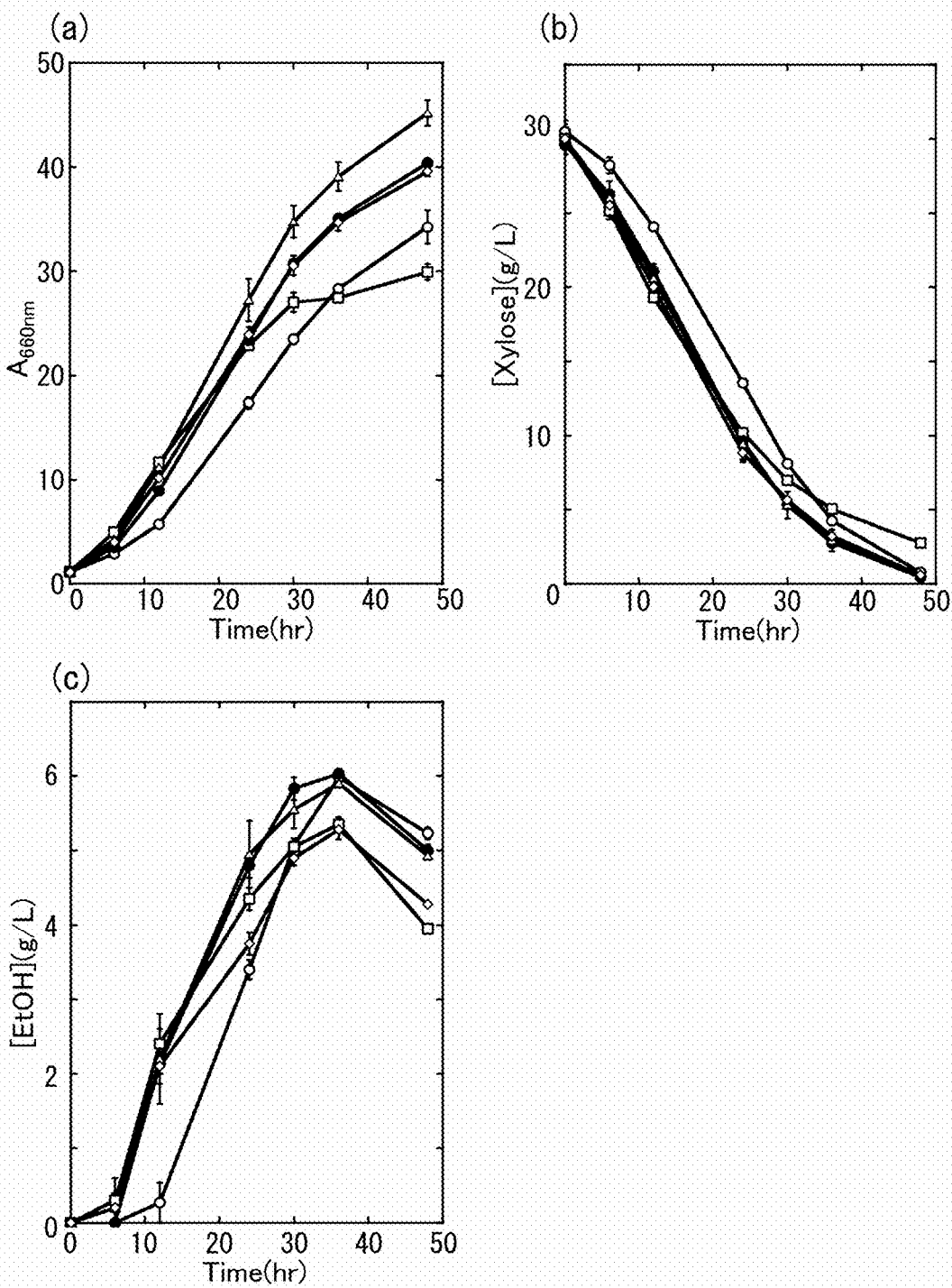
FIG. 5 shows a set of graphs obtained by a batch fermentation test with *S. cerevisiae* Hex$^+$ mutants (SCB13, SCB14, SCB15 and SCB16) and the parent strain SCB7. The fermentation test was conducted with 50 mL of YPX medium containing 30 g/L xylose, at pH 4.0, 35° C., with shaking. (a) cell concentration; (b) xylose concentration (g/L); (c) ethanol concentration. The experiment shows mean values and standard deviations for 3 measurements. Symbols: ○=SCB7; □=SCB13; ●=SCB14; △=SCB15; ◇=SCB16.

The 4 Hex$^+$ variants SCB13, SCB14, SCB15 and SCB16 and the parent strain SCB7 were used for batch fermentation, and production of ethanol from xylose was analyzed. They were inoculated into YPX medium containing 30 g/L xylose, pH 4.0 at 35° C., at an initial cell concentration Abs$_{660nm}$=1.0, and shake cultured (60 rpm). All of the Hex$^+$ variants grew rapidly as the culturing time progressed, but with SCB7 a delay in growth was seen at the initial stage of culturing (FIG. 5a). Xylose consumption and ethanol production showed decreases and increases in proportion with growth (FIGS. 5b and c). The HEX1$_{2-2}$ variant produced ethanol at 4.8 g/L within 24 hours from the start of fermentation, which was 1.4 times higher than the amount of ethanol produced within 24 hours by SCB7 (3.4 g/L). The ethanol yield with HEX1$_{2-2}$ variant was 47%. The ethanol production amount and yield for the HEX1$_{2-3}$ variant was similar to the HEX1$_{2-2}$ variant. The xylose concentrations in the medium were similar for the 4 Hex$^+$ variants, and this decreased linearly at a rate of 1 g/L/hr up to 24 hours. These results suggest that the HEX1, HEX2 and hex3 mutations begin efficient xylose consumption and ethanol production at the start of fermentation.

Characteristics of HEX Mutation Gene (1)

At least 2 genes have hitherto been reported as mutations with enhanced xylose assimilation. One of them is a pho13-deleted mutation, while the other is an example with high TAL1 gene product expression by the PGK promoter. It was then analyzed whether or not the PHO13 or TAL1 gene is present in the 3 HEX mutation genes. Since the pho13-deleted mutation does not produce Pho13 protein, it is recessive with respect to the wild-type allele. Therefore, using the experiment design shown in FIG. 6, it was analyzed whether or not the recessive mutation hex3$_{1-5}$ gene is the PHO13 gene. First, strain SCB45 was created as a pho13-deleted mutation (pho13Δ:kanMX) (FIG. 6a).

Figure 7:
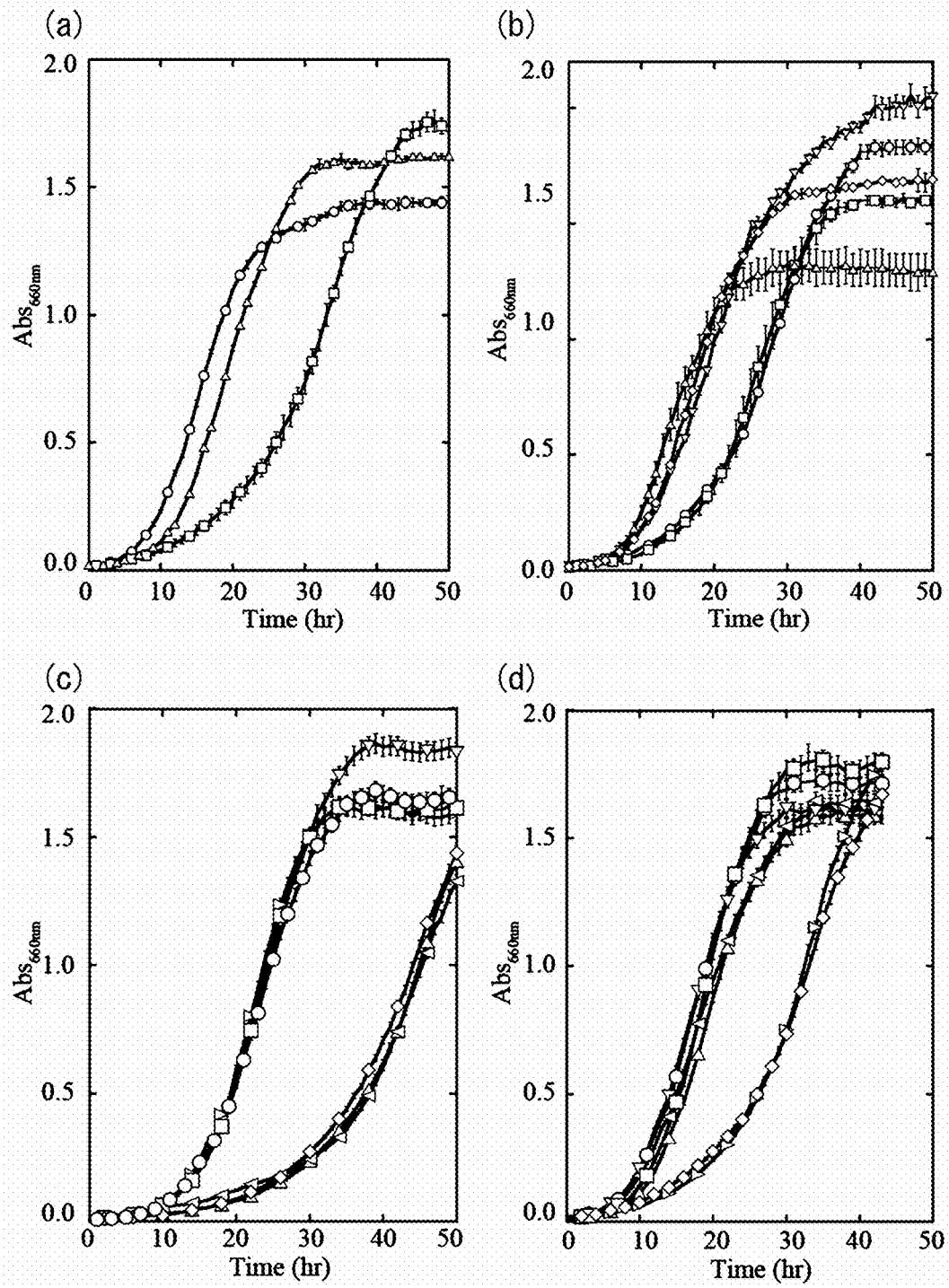
FIG. 7 shows experimental results for Hex$^+$ phenotype analysis of *S. cerevisiae* strains pho13Δ and P$_{TDH3}$-TAL1, and linkage analysis of TAL1 with respect to HEX1$_{2\text{-}2}$ and HEX2$_{2\text{-}3}$. The test cells were inoculated into 5 mL of xylose minimal medium (MSXU, pH 5.5, xylose concentration: 20 g/L), and shake cultured at 35° C. The cell concentration was measured using a biophotorecorder. (a) Growth of strains pho13Δ, P$_{TDH3}$-TAL1 and wild-type in xylose medium. Symbols: □=wild type SCC2-11B; ○=pho13Δ SCB45; △=P$_{TDH3}$-TAL1 SCB44. (b) Dominant/recessive test for pho13Δ and complementarity test for pho13Δ/hex3$_{1\text{-}5}$ diploid. Symbols: ○=WT/WT SCB112; △=pho13Δ/pho13Δ diploid SCB53; □=pho13A/WT heterodiploid SCB52; ▽=hex3$_{1\text{-}5}$/hex3$_{1\text{-}5}$ diploid SCB108; ◇=pho13 Δ/hex3$_{1\text{-}5}$ diploid SCB49. (c) and (d): Linkage analysis. (c) Linkage analysis of TAL1 and HEX1$_{2\text{-}2}$. ○=P$_{TDH3}$-TAL1 SCB44; □=HEX1$_{2\text{-}2}$ SCB105-7A; and for the 4 cross-bred molecules: △=SCB47-3A; ▽=SCB47-3B; right-pointing △=SCB47-3C; left-pointing △=SCB47-3D; ◇=wild-type SCC2-11B. (d) Linkage analysis of TAL1 and HEX2$_{2\text{-}3}$. ○=P$_{TDH3}$-TAL1 SCB44; □=HEX1$_{2\text{-}2}$ SCB106-1D; and for the 4 cross-bred molecules: △=SCB48-6A; ▽=SCB48-6B; right-pointing △=SCB48-6C; left-pointing △=SCB48-6D; ◇=wild-type SCC2-11B. The data are mean values and standard deviations for three measurements.

Next, it was confirmed in xylose medium whether or not SCB45 exhibits Hex$^+$. Growth in xylose medium (xylose concentration: 20 g/L) was clearly more rapid than growth of the wild-type strain, and Gshort was 2.5 hours, which was similar to the hex3$_{1-5}$ variant (FIG. 7a). Also, the pho13-deleted mutation was confirmed to be recessive with respect to the wild type (FIG. 7b). In other words, growth of the pho13Δ/wild type diploid was slower than the pho13Δ/pho13Δ diploid, and very similar to growth of the wild type/wild type diploid (FIG. 7b). Thus, a pho13Δ/hex3$_{1-5}$ heterodiploid was constructed, and growth of this diploid was confirmed to be similar to the pho13Δ/pho13Δ or hex3$_{1-5}$/hex3$_{1-5}$ diploid, and faster than the wild type/wild type diploid. As a result, growth of the pho13Δ/hex3$_{1-5}$ diploid was shown to be rapid growth on the same level as the mutant diploids, indicating that hex3 is a pho13 mutation (FIG. 7b).

It was analyzed whether or not HEX1$_{2-2}$ and HEX2$_{2-3}$ are TAL1 gene mutations. First, strain P$_{TDH3}$-TAL was constructed. The gene structure of the TAL1 region is loxP-kanMX-loxP-P$_{TDH3}$-TAL1. Next, it was confirmed in xylose medium whether or not strain P$_{TDH3}$-TAL1 exhibits Hex$^+$ even for SC lines. As a result, growth in xylose medium was clearly more rapid than growth of the wild-type strain, and Gshort was 2.5 hours, which was similar to the HEX1$_{2-2}$ or HEX2$_{2-3}$ variant (FIG. 7a). Next, HEX1$_{2-2}$ or HEX2$_{2-3}$ was cross-bred with P$_{TDH3}$-TAL1 and heterodiploids were isolated, and after spore formation, the linkage relationship between the mutant genes was analyzed by whether or not the wild-type strain produced the 4 molecules. When diploids obtained from HEX1$_{2-2}$×P$_{TDH3}$-TAL1 and HEX2$_{2-3}$×P$_{TDH3}$-TAL1 were caused to form spores, they were isolated with Hex$^+$:Hex$^-$=4+:0−, 3+:1− and 2+:2−. In other words, the wild-type strain appeared. Thus, the TAL1 gene was a gene different from HEX1$_{2-2}$ and HEX2$_{2-3}$. Also, no additive effect or synergistic effect was seen in the double strains. The numbers of asci examined were 20 asci for the P$_{TDH3}$-TAL1/HEX1$_{2-2}$ diploid SCB47 and 20 asci for the P$_{TDH3}$-TAL1/HEX2$_{2-3}$ diploid SCB48, and the isolation ratio for 4+:0−, 3+:1−, 2+:2− was 4:12:4 and 5:12:3, respectively.

HEX1 was shown to be linked to the ADE1 gene. Specifically, when analysis of the 4 molecules was conducted between strain ade1Δ1 URA3:XM$_8$ and strain HEX1$_{2-2}$, the ratio of novel type (ade1:ade1:HEX1:HEX1):T-type (ade1:ade1 HEX1:W.T:HEX1):non-novel type (ade1 HEX1:ade1 HEX1:W.T:W.T) among the examined 24 asci was 20:4:0. Thus, since appearance of recombinants was low between ade1 and HEX1, the HEX1 gene was linked to ADE1 on yeast chromosome I. Based on the results of next-generation sequencer analysis, the only candidate gene for HEX1$_{2-2}$ and HEX1$_{2-9}$ with mutation linked to ADE1 on chromosome I was CDC19. Thus, the gene mutation was believed to be a powerful candidate for HEX1$_{2-2}$.

Creation of Reference Strain Draft Genomic Sequence

The ethanol-producing practical yeast strain NAM34-4C was cultured overnight in YPD medium (2% peptone [BD], 1% yeast extract [BD], 2% glucose [Wako Pure Chemical Industries, Ltd.]), and Gen Torukun™ (for yeast) High Recovery (Takara Bio, Inc.) was used to prepare genomic DNA according to the manufacturer's protocol.

The obtained NAM34-4C genomic DNA was used for full genome sequencing by the pair end method using a GS FLX Titanium system (Roche Diagnostics), according to the protocol of the sequencer, and nucleotide sequence information was obtained for a total number of 379,166,058 bases, comprising 1,030,498 reads with a mean chain length of 368 bases. The read information was used for assembly with GS De Novo Assembler (Roche Diagnostics) software, and draft genomic sequence ver.0 was constructed comprising nucleotide sequence information for a total number of 11,594,757 bases comprising 3,861 contigs. As a result of using the pair end information for linkage as gaps (N) between the contigs, draft genomic sequence ver.1 was constructed comprising 11,614,635 nucleotide sequences, with a mean redundancy of 31.2 times and 56 scaffolds.

Next, the obtained NAM34-4C genomic DNA was used for full genome sequencing with a SOLiD 3 system (Life Technologies), according to the protocol of the sequencer, and nucleotide sequence information was obtained for a total number of 14,275,152,600 bases, comprising 285,503,052 reads with chain lengths of 50 bases. Using the obtained read data, with reference to NAM34-4C draft genomic sequence ver.0, the read data was mapped to the reference with BWA (http://bio-bwa.sourceforge.net) and SAMtools (http://samtools.sourceforge.net), and bases differing from draft genomic sequence ver.0 were detected. As a result, base differences were detected at 2,242 locations. A draft genomic sequence was created reflecting these differing bases in draft genome ver.0, and using this draft genomic sequence as reference, the read data obtained by a SOLiD 3 system was again used for mapping against Bowtie (http://bowtie-bio.sourceforge.net), under completely identical conditions at one location. Among the differing locations, the differing locations where redundancy was increased, compared to using the draft genomic sequence ver.0 as reference, were found to be 1,730 locations. Since these differing locations were thought to be sequencing errors with the GS FLX Titanium system, draft genomic sequence ver.2 was constructed comprising 11,614,855 nucleotide sequences with 56 scaffolds, reflecting the results of sequencing with the SOLiD 3 system, by linking between the contigs using the aforementioned pair end information.

Next, using NAM34-4C genomic DNA, sequencing was carried out on 483 gaps present in the scaffold sequences of draft genomic sequence ver.2, by the Sanger method using a 3730×1 DNA Analyzer (Life Technologies), and the nucleotide sequences of 389 locations were determined. Draft genomic sequence ver.3 was constructed to reflect these nucleotide sequences, comprising 11,563,143 nucleotide sequences, with 56 scaffolds, the gaps between the contigs that could not be determined being linked with N100.

Next, using full gene amino acid sequence information from genomic information for the laboratory yeast strain S288c (http://www.yeastgenome.org), the genes of draft genomic sequence ver.3 were detected by Exonerate (http://www.ebi.ac.uk/~guy/exonerate/), and the information for 5,669 genes were ascribed to this draft genomic sequence.

Preparation of Genomic DNA

The xylose metabolism-enhanced strains HEX1$_{2-2}$, HEX1$_{2-9}$, HEX2$_{2-3}$ and hex3$_{1-5}$ isolated by the method described above were each inoculated into 15 mL of YPD medium in a conical tube and cultured overnight under aerobic conditions, 150 rpm, 37° C. The obtained cells (approximate OD600=1.0) were divided into 8 aliquots, and genomic DNA was purified with a Gen Torukun (for yeast, Takara Bio, Inc.) according to the specified protocol. The purified genomic DNA was extracted with Tris-HCl (pH 8.0), measured for concentration and stored at 4° C. until creation of a SOLiD fragment library. The same experiment was conducted for the high-concentration xylose metabolism-enhanced strains SXM1 and SXM2 mentioned below.

Creation of SOLiD Fragment Library

In order to elucidate the full genomic DNA sequence of the xylose metabolism-enhanced variants by next-generation sequence analysis, the genomic DNA purified in 1. above was used to create SOLiD5500 fragment libraries for each, according to the specified protocol. First, 3-5 μg of genomic DNA was physically fragmented to approximately 150-200 bp using a COVALIS ultrasonic disruptor. Upon confirming by agarose gel electrophoresis that suitable sizes and amounts had been obtained, and purifying them, P1 and P2 adapters were linked to the genomic DNA fragments using T4DNA ligase. Next, for library amplification, PCR was carried out with a small number of cycles (5-10 cycles) using P1-P2 specific primers, for uniform amplification of each library while minimizing amplification bias, to construct SOLiD fragment libraries. Since the samples were sequenced simultaneously, independent barcode sequences were applied for each. The average size of the final fragment library was confirmed to be a single peak for approximately 220-250 bp, using a bioanalyzer. The concentration of each obtained library was greater than 10 pM.

Preparation and Deposition of Beads by Emulsion PCR

Using a next-generation sequencer SOLiD system, template DNA fragments derived from genomic DNA prepared on microbeads were used for large-scale sequencing. For this, 50 µL-70 µL (0.5 pM-0.7 pM) of each created library was used for emulsion PCR to obtain one template DNA on each bead, and as a result the obtained SOLiD5500 library size was approximately $3.0 \times 10^9$. The obtained beads were covalently bonded to a flow cell and rinsed, and then supplied for sequencing.

Next-Generation Sequencing Run

Prior to the sequencing run, a small amount of library beads was used for a WFA run, and upon confirming the quality of the created beads, fragment sequencing was carried out according to the specified protocol. Each sequencing run was conducted by SOLiD5500 sequencing (75 bp), and read data were obtained. The color balance was confirmed in each sequencing cycle by a Satay plot, and the sequencing run was confirmed to be satisfactory.

Primary Data Analysis and Calling of SNPs

Using GIR01_scaffoldv3r1 genome data for NAM34-4C (haploid strain) described above as the reference sequence, the sequence read data (sxq file) for each variant were mapped and SNPs extracted, using LifeScope software (Life Technologies). The mapping was conducted under the basic conditions for map reads, the diBayes analysis conditions were high stringency using only the uniquely mapped read data, and all of the possible mutation candidates were listed without setting a cut-off threshold value, in order to avoid missing candidates. As a result of mapping, it was possible to obtain data for each variant with a depth of coverage of ×100 or greater. Also, as a result of mutation analysis by diBayes, results were obtained as shown in the following table, for the SNPs of the variants. Incidentally, InDel analysis was also conducted simultaneously in consideration of the possibility of nucleotide deletions or insertions in addition to SNPs, but since no significant InDel mutations were found, the HEX/SXM variants were considered to be due to base substitution mutations.

Secondary Analysis (Mapping of Mutation Data onto Genetic Information)

The mutation data (gff file format) obtained by the pipeline described above contains only information relating to the position of the mutation in the reference sequence NAM34-4C genome, the mutated base (reference base→mutated base) and the coverage, while it lacks relative information, specifically about where the mutation is on which gene. Therefore, as already mentioned, ORF information extracted from the NAM34-4C reference genome was used, and in order to extract the mutation position and mutation type, a filtering program was written using the programming language Ruby, and the necessary genetic information was extracted. Simultaneously, for mutations within coding regions, the same data extraction was carried out even for amino acid-substitutions or nonsense mutations (stops).

All of the obtained mutation data have differences between the diBayes read data and reference data, and the individual mutation data are not at all uniform. This is because in terms of the individual nucleotides, there are differences in terms of the depth of coverage and number of reads containing mutations. Furthermore, three different possible mutation types (3 types other than the reference base) exist. The 3 different mutation types are only one type in some cases (for example, A→T), or in some cases the mutation is called based on the probabilities of all 3 mutations (for example, A→T (80%), C (10%), G (10%)). Thus, as an index of the certainty of these mutations, the total coverage for a given nucleotide position was not used, but rather a P-value was introduced, with the number called as any of ATCG as the denominator, and with the number of reads with the mutation type most called as a mutation (for example, reference A→mutation G), as the numerator. This differs from the commonly used P-value in that it excludes instances called as N. In next-generation sequencing, calling is not only as the 4 bases ATCG, but the position may also be called as "N", i.e. unidentifiable as one of ATCG. While this allows more highly accurate data to be obtained, there is a loss of data, and therefore sequencing must be carried out with the overall coverage set higher in anticipation of that amount. This makes it possible to compare the quality of candidate mutations.

Identification of Gene Mutations Responsible for Enhanced Xylose Metabolism by Logic Programming in Consideration of Genetic Background By full genomic analysis using next-generation sequencing, mutations were detected at about 1,000 locations in any one of the variants, and numerous errors due to next-generation sequencing were also assumed to be included. Even if an accurate full genome nucleotide sequence could be obtained by next-generation sequencing, and even it was determined how many causative mutations were present by genetic analysis, it is not an easy matter to find one to several causative mutations from among 1000 candidate mutations. By introducing a P-value it is possible to rank mutations with greater certainty, but since a considerable number of the candidate mutations detected by diBayes become ranked higher, the P-value is nothing more than an index of the certainty of whether the mutation is present in the variant genome, and it is practically impossible to experimentally verify that the mutation contributes to the phenotype. Thus, according to the invention there has been devised a method of "logic programming in consideration of genetic background" to allow identification of candidate mutations.

The phylogenetic relationship between the strains is as shown in FIG. 1b. When mutation transfer is carried out by prolonged culturing, mutations basically occur independently and randomly. Consequently, the possibility of mutations taking place at the same location is infinitely close to zero. Furthermore, it may be assumed that the possibility that a mutation once acquired would revert back to the nucleotide before the mutation is also nearly zero. Table 3 summarizes the chances that a mutation could logically be present in the other 5 strains, considering the phylogenetic relationship of the 6 variants obtained in this case and focusing on one mutation in a given strain. A "0" in Table 3 indicates that a mutation must not be present while a "1" indicates that a mutation must be present, and their combinations are indicated by $2^6$, or 64 different binary codes. Level 1 indicates to which of the strains the combination of mutations detected for each strain is unique, when the data is considered reliable (Nos. 2-6, 31).

TABLE 3

Boolean logic for HEX/SXM analyses

| No. | Level 1 | Level 2 | Level 3 | HEX1 (2-2) | HEX2 (2-3) | SXM1 | hex3 (1-5) | HEX1 (2-9) | SXM2 | Binary code | sum |
|---|---|---|---|---|---|---|---|---|---|---|---|
| 1 | No mutations | COMMON | HEX2 (2-3), SXM1, hex3 (1-5), HEX1 (2-9), or SXM2 | 0 | 0 | 0 | 0 | 0 | 0 | 000000 | 0 |
| 2 | SXM2 | nonsense | No mutations | 0 | 0 | 0 | 0 | 0 | 1 | 000001 | 1 |
| 3 | HEX1 (2-9) | nonsense | No mutations | 0 | 0 | 0 | 0 | 1 | 0 | 000010 | 1 |
| 4 | hex3 (1-5) | nonsense | No mutations | 0 | 0 | 0 | 1 | 0 | 0 | 000100 | 1 |
| 5 | SXM1 | nonsense | No mutations | 0 | 0 | 1 | 0 | 0 | 0 | 001000 | 1 |
| 6 | HEX2 (2-3) | nonsense | No mutations | 0 | 1 | 0 | 0 | 0 | 0 | 010000 | 1 |
| 7 | nonsense | nonsense | No mutations | 1 | 0 | 0 | 0 | 0 | 0 | 100000 | 1 |
| 8 | nonsense | nonsense | SXM2 or HEX1 (2-9) | 0 | 0 | 0 | 0 | 1 | 1 | 000011 | 2 |
| 9 | nonsense | nonsense | SXM2 or hex3 (1-5) | 0 | 0 | 0 | 1 | 0 | 1 | 000101 | 2 |
| 10 | nonsense | nonsense | HEX1 (2-2) or SXM2 or SXM1 | 0 | 0 | 1 | 0 | 0 | 1 | 001001 | 2 |
| 11 | nonsense | nonsense | SXM2 or HEX2 (2-3) | 0 | 1 | 0 | 0 | 0 | 1 | 010001 | 2 |
| 12 | nonsense | nonsense | SXM2 or HEX1 (2-2) | 1 | 0 | 0 | 0 | 0 | 1 | 100001 | 2 |
| 13 | nonsense | nonsense | HEX1 (2-9) or hex3 (1-5) | 0 | 0 | 0 | 1 | 1 | 0 | 000110 | 2 |
| 14 | nonsense | nonsense | HEX1 (2-9) or SXM1 | 0 | 0 | 1 | 0 | 1 | 0 | 001010 | 2 |
| 15 | nonsense | nonsense | HEX1 (2-9) or HEX2 (2-3) | 0 | 1 | 0 | 0 | 1 | 0 | 010010 | 2 |
| 16 | nonsense | nonsense | HEX2-9 | 1 | 0 | 0 | 0 | 1 | 0 | 100010 | 2 |
| 17 | nonsense | nonsense | hex3(1-5) or SXM1 | 0 | 0 | 1 | 1 | 0 | 0 | 001100 | 2 |
| 18 | nonsense | nonsense | hex3(1-5) or HEX2 (2-3) | 0 | 1 | 0 | 1 | 0 | 0 | 010100 | 2 |
| 19 | nonsense | nonsense | hex3(1-5) | 1 | 0 | 0 | 1 | 0 | 0 | 100100 | 2 |
| 20 | nonsense | nonsense | SXM1 or HEX2 (2-3) | 0 | 1 | 1 | 0 | 0 | 0 | 011000 | 2 |
| 21 | nonsense | nonsense | SXM1 or HEX1 (2-2) | 1 | 0 | 1 | 0 | 0 | 0 | 101000 | 2 |
| 22 | nonsense | nonsense | HEX2 (2-3) | 1 | 1 | 0 | 0 | 0 | 0 | 110000 | 2 |
| 23 | nonsense | nonsense | nonsense | 0 | 0 | 0 | 1 | 1 | 1 | 000111 | 3 |
| 24 | nonsense | nonsense | nonsense | 0 | 0 | 1 | 0 | 1 | 1 | 001011 | 3 |
| 25 | nonsense | nonsense | nonsense | 0 | 1 | 0 | 0 | 1 | 1 | 010011 | 3 |
| 26 | nonsense | nonsense | nonsense | 1 | 0 | 0 | 0 | 1 | 1 | 100011 | 3 |
| 27 | nonsense | nonsense | nonsense | 0 | 0 | 1 | 1 | 0 | 1 | 001101 | 3 |
| 28 | nonsense | nonsense | nonsense | 0 | 1 | 0 | 1 | 0 | 1 | 010101 | 3 |
| 29 | nonsense | nonsense | nonsense | 1 | 0 | 0 | 1 | 0 | 1 | 100101 | 3 |
| 30 | nonsense | nonsense | nonsense | 0 | 1 | 1 | 0 | 0 | 1 | 011001 | 3 |
| 31 | HEX1 (2-2) | nonsense | nonsense | 1 | 0 | 1 | 0 | 0 | 1 | 101001 | 3 |
| 32 | nonsense | nonsense | nonsense | 1 | 1 | 0 | 0 | 0 | 1 | 110001 | 3 |
| 33 | nonsense | nonsense | nonsense | 0 | 0 | 1 | 1 | 1 | 0 | 001110 | 3 |
| 34 | nonsense | HEX1 (2-2) | nonsense | 0 | 1 | 0 | 1 | 1 | 0 | 010110 | 3 |
| 35 | nonsense | nonsense | nonsense | 1 | 0 | 0 | 1 | 1 | 0 | 100110 | 3 |
| 36 | nonsense | nonsense | nonsense | 0 | 1 | 1 | 0 | 1 | 0 | 011010 | 3 |
| 37 | nonsense | nonsense | nonsense | 1 | 0 | 1 | 0 | 1 | 0 | 101010 | 3 |
| 38 | nonsense | nonsense | nonsense | 1 | 1 | 0 | 0 | 1 | 0 | 110010 | 3 |
| 39 | nonsense | nonsense | nonsense | 0 | 1 | 1 | 1 | 0 | 0 | 011100 | 3 |
| 40 | nonsense | nonsense | nonsense | 1 | 0 | 1 | 1 | 0 | 0 | 101100 | 3 |
| 41 | nonsense | nonsense | nonsense | 1 | 1 | 0 | 1 | 0 | 0 | 110100 | 3 |
| 42 | nonsense | nonsense | nonsense | 1 | 1 | 1 | 0 | 0 | 0 | 111000 | 3 |
| 43 | nonsense | nonsense | nonsense | 0 | 0 | 1 | 1 | 1 | 1 | 001111 | 4 |
| 44 | nonsense | nonsense | nonsense | 0 | 1 | 0 | 1 | 1 | 1 | 010111 | 4 |
| 45 | nonsense | nonsense | nonsense | 1 | 0 | 0 | 1 | 1 | 1 | 100111 | 4 |
| 46 | nonsense | nonsense | nonsense | 0 | 1 | 1 | 0 | 1 | 1 | 011011 | 4 |
| 47 | nonsense | nonsense | nonsense | 1 | 0 | 1 | 0 | 1 | 1 | 101011 | 4 |
| 48 | nonsense | nonsense | nonsense | 1 | 1 | 0 | 0 | 1 | 1 | 110011 | 4 |
| 49 | nonsense | nonsense | nonsense | 0 | 1 | 1 | 1 | 0 | 1 | 011101 | 4 |
| 50 | nonsense | nonsense | nonsense | 1 | 0 | 1 | 1 | 0 | 1 | 101101 | 4 |
| 51 | nonsense | nonsense | nonsense | 1 | 1 | 0 | 1 | 0 | 1 | 110101 | 4 |
| 52 | nonsense | nonsense | nonsense | 1 | 1 | 1 | 0 | 0 | 1 | 111001 | 4 |
| 53 | nonsense | nonsense | nonsense | 0 | 1 | 1 | 1 | 1 | 0 | 011110 | 4 |
| 54 | nonsense | nonsense | nonsense | 1 | 0 | 1 | 1 | 1 | 0 | 101110 | 4 |
| 55 | nonsense | nonsense | nonsense | 1 | 1 | 0 | 1 | 1 | 0 | 110110 | 4 |
| 56 | nonsense | nonsense | nonsense | 1 | 1 | 1 | 0 | 1 | 0 | 111010 | 4 |
| 57 | nonsense | nonsense | nonsense | 1 | 1 | 1 | 1 | 0 | 0 | 111100 | 4 |
| 58 | nonsense | nonsense | nonsense | 0 | 1 | 1 | 1 | 1 | 1 | 011111 | 5 |
| 59 | nonsense | HEX2 (2-3) | nonsense | 1 | 0 | 1 | 1 | 1 | 1 | 101111 | 5 |
| 60 | nonsense | SXM1 | nonsense | 1 | 1 | 0 | 1 | 1 | 1 | 110111 | 5 |
| 61 | nonsense | hex3 (1-5) | nonsense | 1 | 1 | 1 | 0 | 1 | 1 | 111011 | 5 |
| 62 | nonsense | HEX1 (2-9) | nonsense | 1 | 1 | 1 | 1 | 0 | 1 | 111101 | 5 |
| 63 | nonsense | SXM2 | nonsense | 1 | 1 | 1 | 1 | 1 | 0 | 111110 | 5 |
| 64 | COMMON | No mutations | nonsense | 1 | 1 | 1 | 1 | 1 | 1 | 111111 | 6 |

In this method, as shown in Table 3, it is possible to perform similar analysis not only when all of the experimental data is assumed to be correct, but even when errors are present. The mutation combinations that can be detected are shown in Level 2 for the case where the reference is in error and the mutation is present only in one strain (Nos. 1, 8-22), and in Level 3 for the case where one of the experimental data other than the reference is in error (Nos. 34, 59-63). Combinations other than these, for any of the levels, are: not logically true (nonsense), common mutations (COMMON) or no mutations present (No mutations), and therefore these are excluded from candidate mutations that can contribute to the phenotype of each strain.

Characteristics of HEX Mutation Gene (2)

An experiment was designed to verify whether or not CDC19 is a $HEX1_{2-2}$ mutation (FIG. 8).

Figure 9:
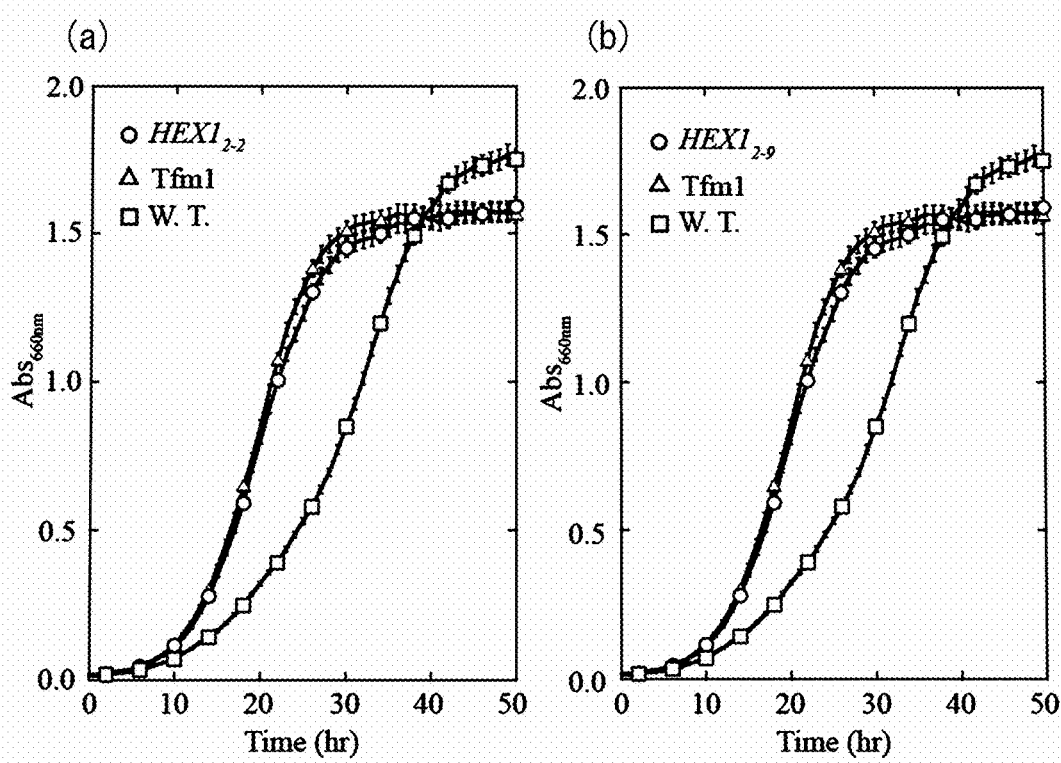
FIG. 9 shows the experimental results for identifying the HEX1$_{2\text{-}2}$ and HEX1$_{2\text{-}9}$ mutant genes. The test cells were inoculated into 5 mL of xylose minimal medium (MSXU, pH 5.5, xylose concentration: 20 g/L), and shake cultured at 35° C. The cell concentration was measured using a biophotorecorder. (a) Identification of HEX1$_{2\text{-}2}$. Symbols: □=wild type SCC2-11B; ○=HEX1$_{2\text{-}2}$ SCB38; △=transformant. (b) Identification of HEX1$_{2\text{-}9}$. Symbols: □=wild type SCC2-11B; ○=HEX1$_{2\text{-}9}$; △=transformant. The data are mean values and standard deviations for three measurements.

When transformants incorporating kanMX in the flanking region of CDC19 were isolated and their growth examined, they were found to be Hex$^+$ as expected. Next, kanMX-CDC19 DNA was subjected to PCR amplification and G418-resistant transformants among the xylose-assimilating (SCC2-11B) strains based on the amplified DNA were selected. As a result, 29 of the 100 transformants were found to be Hex$^+$ (FIG. 9$a$). Thus, $HEX1_{2-2}$ was the CDC19 gene. While $HEX1_{2-9}$ was inferred to be the same gene as $HEX1_{2-2}$ based on genetic analysis, $HEX1_{2-9}$ was definitely shown to be CDC19 by confirmation using the same experiment design (FIG. 9$b$). Also, upon determining the nucleotide sequences of the $HEX1_{2-2}$ and $HEX1_{2-9}$ genes, they were confirmed to be substitution mutations in the structural gene (corresponding to a substitution of threonine for proline at position 272 of SEQ ID NO: 5, and a substitution of proline for alanine at position 344 of SEQ ID NO: 5).

Figure 10:
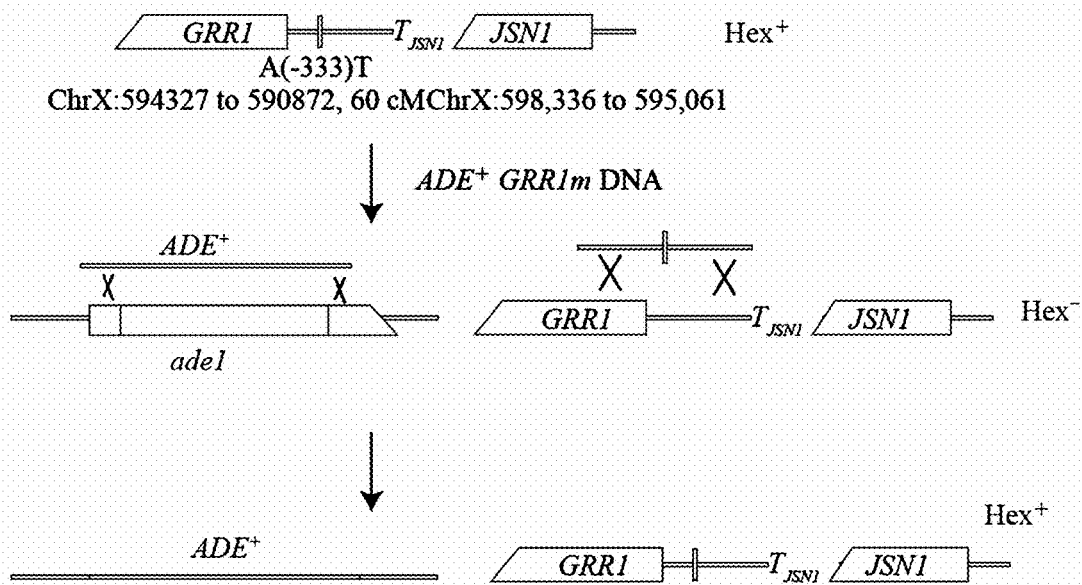
FIG. 10 shows a design for identification of HEX2$_{2\text{-}3}$ mutation by double transformation. Using strain ade1Δ1 XM as the recipient strain, Ade$^+$ transformants are obtained using Ade$^+$ DNA and DNA with a length of 2 kb consisting of 1 kb downstream and upstream of the mutation site in the upstream region of the GRR1 coding region (P$_{GRR1}$). It is determined, in xylose medium, whether or not transformants including the mutation site can be separated from among the Ade$^+$ transformants. Since the final gene structure is the P$_{GRR1}$-GRR1 XM gene structure, if the strain exhibits Hex$^+$ then HEX2$_{2\text{-}3}$ can be demonstrated to be P$_{GRR1}$-GRR1.

The HEX2 gene was thought to be a mutation in the upstream region of the GRR1 coding region, based on next-generation sequencer analysis. This was therefore confirmed using the experiment design shown in FIG. 10.

Figure 11:
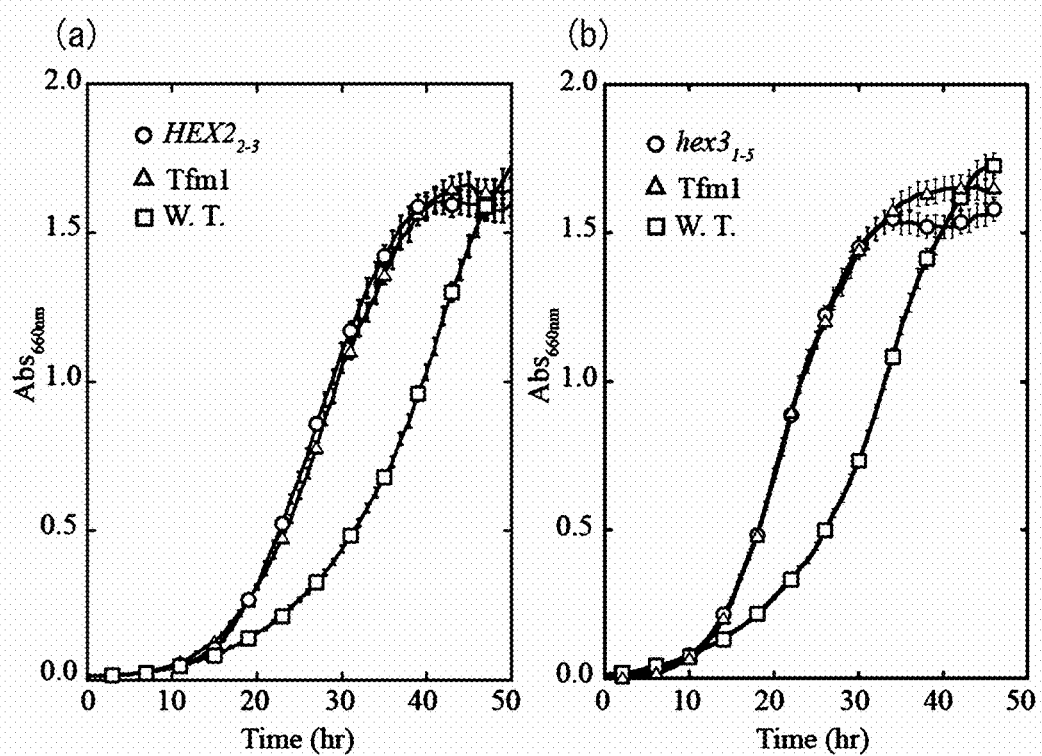
FIG. 11 shows the experimental results for identifying the HEX2$_{2\text{-}3}$ and hex3$_{1\text{-}5}$ mutant genes. The test cells were inoculated into 5 mL of xylose minimal medium (MSXU, pH 5.5, xylose concentration: 20 g/L), and shake cultured at 35° C. The cell concentration was measured using a biophotorecorder. (a) Identification of HEX2$_{2\text{-}3}$. Symbols: □=wild type SCC12; ○=HEX2$_{2\text{-}3}$ SCB15; △=transformant. (b) Identification of hex3$_{1\text{-}5}$. Symbols: □=wild type SCC12; ○=hex3$_{1\text{-}5}$; △=transformant. The data are mean values and standard deviations for three measurements.

Specifically, ADE1$^+$ DNA and mutant GRR1 DNA were added to strain ade1Δ1 XM, and Ade$^+$ transformants were obtained. Next, 100 of the transformants were selected and streaked onto 10 g/L xylose-containing MSX minimal solid medium at pH 5.5 using a platinum wire, and stationary cultured at 30° C. for 2-4 days. As a result, growth occurred with 2 of the test cells. Upon confirming growth of the two strains on MSX medium at pH 5.5, they were found to exhibit rapid Hex$^+$ growth in xylose medium (FIG. 11$a$). When the upstream region of the GRR1 coding region was subjected to nucleotide sequence analysis, substitution mutation was confirmed in the upstream region of the GRR1 coding region as decoded with a next-generation sequencer (not shown in data). It was thereby concluded that the $HEX2_{2-3}$ gene is a mutation in the region upstream from the GRR1 coding region. Also, upon determining the nucleotide sequence of the $HEX2_{2-3}$ gene, a substitution mutation (substitution of thymine for adenine at position −333 of SEQ ID NO: 6) was confirmed in the region upstream from the coding region.

The HEX3 gene was demonstrated to be the PHO13 gene by genetic analysis, but analysis by the experiment design shown in FIG. 8 definitely showed that HEX3 was the PHO13 gene (FIG. 11$b$).

Inhibition Concentration of Xylose on Yeast Growth

Figure 12:
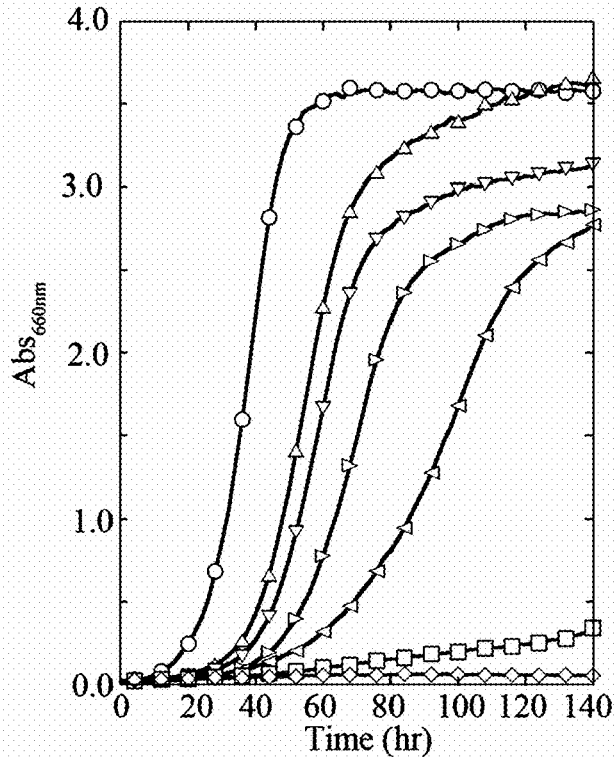
FIG. 12 shows the verification experiment results for xylose inhibition concentration with respect to growth of strain SCB14. Growth was analyzed in YPXn medium containing xylose at concentrations from 20 g/L to 200 g/L. Symbols: ○=20 g/L; △=100 g/L; ▽=120 g/L; right-pointing △=140 g/L; left-pointing △=160 g/L; □=180 g/L, ◇=200 g/L.

Strain SCB14 was inoculated into YPX media at pH 4.0, which had varying xylose concentrations of 20 g/L to 200 g/L, and shake cultured at 35° C. Upon analyzing cell growth with a biophotorecorder, strain SCB14 experienced powerful growth inhibition with increasing xylose concentration, failing to grow with a concentration of 180 g/L xylose or higher (FIG. 12). It is thought that the xylose that has been taken up directly or indirectly inhibits metabolism, or that growth is inhibited by metabolic intermediates derived from xylose.

The mutants capable of efficiently assimilating xylose even with high concentrations of xylose were isolated and an experiment to analyze the factors involved was designed, establishing YPX18 medium at pH 4.0 as the selection medium.

Figure 13:
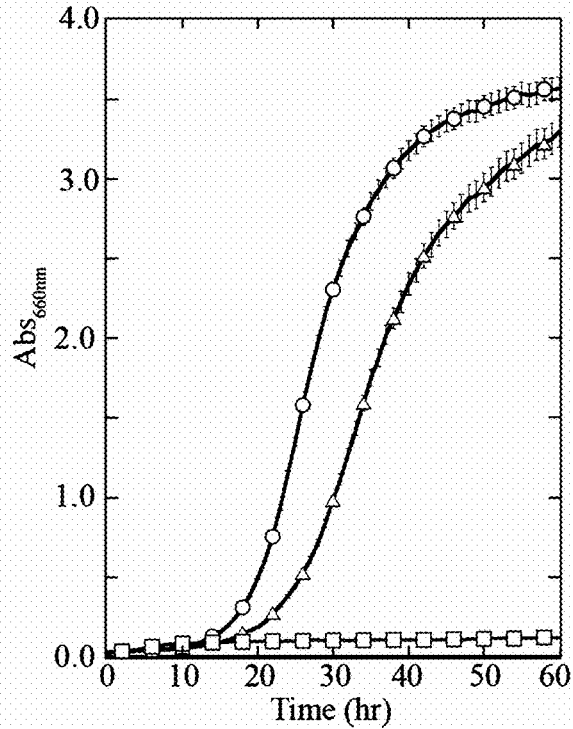
FIG. 13 shows growth of Sxm$^+$ mutants in high-concentration (180 g/L xylose concentration) xylose medium. Two test cell types were inoculated into 5 mL of uracil-containing YPX18 medium at pH 4.0 to an initial cell concentration of Abs$_{660nm}$=0.014, and growth was analyzed with a biophotorecorder. Symbols: ○=SxmA⁺ mutant; Δ=SxmB⁺ mutant; □=HEX1$_{2-2}$ parent strain SCB14.

Isolation of Mutants Assimilating High-Concentration Xylose with High Efficiency Variants assimilating high-concentration xylose were isolated from strain SCB14. Specifically, strain SCB14 was inoculated into YPX18 medium at pH 4.0 and shake cultured at 35° C. When the cell concentration sharply increased during the anaphase of culturing, the L-shaped test tube culture solution was appropriately diluted and smeared onto YPX18 plate medium, and stationary cultured at 30° C. for 2-4 days. Two large rapidly growing colonies were independently isolated (SCB32 and SCB33). After isolation of the single cells, growth of the 2 colonies was examined on YPX18 medium, and compared with the parent strain SCB14 (FIG. 13). The two cells exhibited growth on YPX18 medium, whereas the parent strain did not grow. The mutants efficiently assimilating xylose in high-concentration xylose medium (xylose concentration: 180 g/L) were named "Super Xylose assimilation Metabolism" (SXM) variants, and the phenotype was designated as Sxm$^+$.

Genetic Analysis of Sxm$^+$ Phenotype-Conferring Mutations

Figure 14:
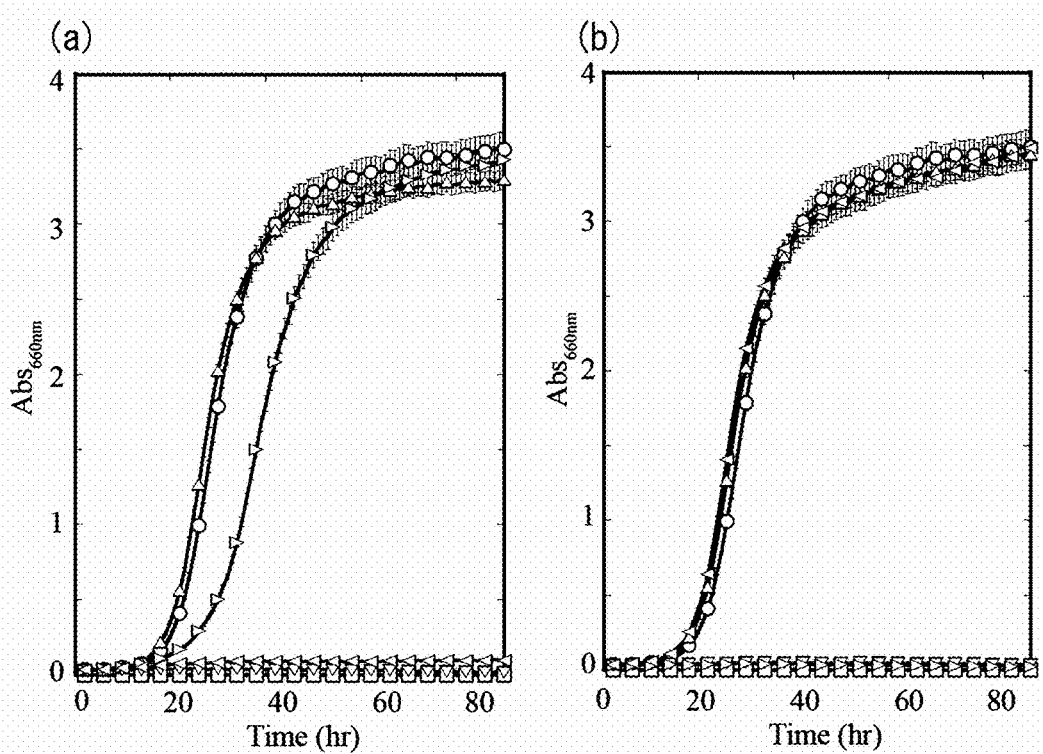
FIG. 14 shows experimental results for analysis of 4 spores obtained by cross-breeding strain SxmA⁺ with the parent strain. There were used strain SCB39 (MATa SxmA⁺ HEX1$_{2-2}$), the parent strain SCB105-3A (MATα HEX1$_{2-2}$) and 4 SCB42 diploid spore clones obtained by cross-breeding. Six test cell types were inoculated into 5 mL of uracil-added YPX18 medium (180 g/L xylose concentration) at pH 4.0 to an initial cell concentration of Abs$_{660nm}$=0.014, and growth was analyzed with a biophotorecorder. (a) Analysis of SCB42 ascospore #2. Symbols: ○=SxmA⁺ mutant (SXM1 SXMC1); □=HEX1$_{2-2}$; Δ=SCB42-2A; ∇=SCB42-2B; right-pointing Δ=SCB42-2C; left-pointing Δ=SCB42-2D. (b) Analysis of SCB42 ascospore #4. Symbols: ○=SxmA⁺ mutant (SXM1 SXMC1); □=HEX1$_{2-2}$; Δ=SCB42-4A; ∇=SCB42-4B; right-pointing Δ=SCB42-4C; left-pointing Δ=SCB42-4D.

The number of Sxm$^+$ mutations was analyzed. First, the SCB32 variants (MATa pho87Δ ura3:loxP-$P_{TEF}$-kanMX-$T_{TEF}$-loxP-$P_{TDH3}$-XYL1-$T_{TDH3}$-$P_{TDH3}$-XYL2-$T_{TDH3}$-$P_{TDH3}$-XKS1-$T_{TDH3}$ $HEX1_{2-2}$ SxmA$^+$) were analyzed. In order to remove the uracil requirement of strain SCB32, transformants of SCB32 by URA$^+$ DNA were isolated as Ura$^+$ G418 sensitive strains. The gene structure was MATa pho874 URA3:$P_{TDH3}$-XYL1-$T_{TDH3}$-$P_{TDH3}$-XYL2-$T_{TDH3}$-$P_{TDH3}$-XKS1-$T_{TDH3}$ $HEX1_{2-2}$ SxmA$^+$, and it was named strain SCB39. A diploid was created by cross-breeding of SxmA$^+$ Hex$^+$ SCB39 and Hex$^+$ SCB105-3A (MATα ura3Δ: XM$_8$ $HEX1_{2-2}$), and spores were formed. Growth of the 4 spore clones on YPX18 liquid medium (xylose concentration: 180 g/L) at pH 4.0 at a temperature of 35° C. was examined. As a result, all of the 24 examined asci were isolated as 2 growing spore clones Sxm$^+$ or 2 non-growing spore clones Sxm$^-$ (FIG. 14). Upon examination in greater detail, they were divided into a group including strains exhibiting slower growth than the SxmA$^+$ mutant (FIG. 14$a$) and a group exhibiting the same fast growth as the SxmA$^+$ mutant (FIG. 14$b$). This was assumed to be because one mutation is necessary for growth on YPX18 medium, while the other mutation promotes cell growth on YPX18 medium. Stated differently, they may be inferred as having at least 2 mutations, and were named SXM1 and SXMC1, respectively. It was hypothesized that, for example, the 4 spore genotypes of SCB39 shown in FIG. 14$a$ were SXM1 single mutations (SCB42-2C) or SXM1 SXMC1 double mutations (SCB42-2A), and the remaining SCB42-2B and SCB42-2D were the SXMC1 single mutation and wild type. In order to confirm this, a diploid was created by cross-breeding the parent strain SxmA$^+$ SCB39 (SXM1 SXMC1) with strain SXM1 or SXMC1, and spores were formed. The examined 24 asci were isolated as SXM1 SXMC1 (fast growing): SXM1 (slow growing) or SXM1 SXMC1 (fast growing): SXMC1 (non-growing)=2:2. The SxmA$^+$ genotype was thereby established as SXM1 SXMC1.

Figure 15:
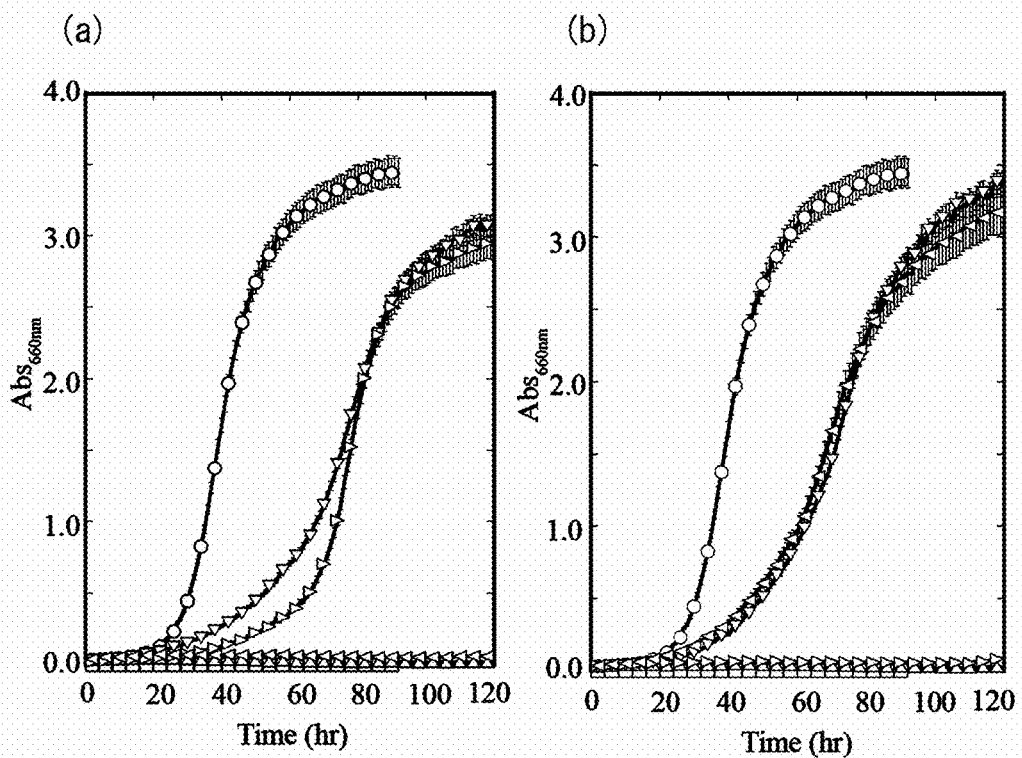
FIG. 15 shows experimental results for analysis of 4 spores obtained by cross-breeding strain SxmB⁺ with the parent strain. There were used strain SCB40 (MATa SxmB⁺ HEX1$_{2-2}$), the parent strain SCB105-7A (MATα HEX1$_{2-2}$) and 4 SCB43 diploid spore clones obtained by cross-breeding them. Six test cell types were inoculated into 5 mL of uracil-added YPX18 medium (180 g/L xylose concentration) at pH 4.0 to an initial cell concentration of Abs$_{660nm}$=0.014, and growth was analyzed with a biophotorecorder. (a) Analysis of SCB43-1. Symbols: ○=SxmB⁺ mutant; □=HEX1$_{2-2}$; Δ=SCB42-1A; ∇=SCB42-1B; right-pointing Δ=SCB42-1C; left-pointing Δ=SCB42-1D. (b) Analysis of SCB42-3. Symbols: ○=SxmB⁺ mutant; □=HEX1$_{2-2}$; Δ=SCB42-3A; ∇=SCB42-3B; right-pointing Δ=SCB42-3C; left-pointing Δ=SCB42-3D.

Strain SCB33 was analyzed next. Transformants of strain SCB33 by URA$^+$ DNA were isolated as Ura$^+$ G418 sensitive strains. A diploid was created by cross-breeding the SxmB$^+$ Hex$^+$ strain SCB40 (MATa pho87Δ URA3:P$_{TDH3}$-XYL1-T$_{TDH3}$-P$_{TDH3}$-XYL2-T$_{TDH3}$-P$_{TDH3}$-XKS1-T$_{TDH3}$ HEX1$_{2-2}$SxmB$^+$) and the Hex$^+$ strain SCB105-7A (MATα ura3Δ:XM$_8$ HEX1$_{2-2}$), and spores were formed. Growth of the 4 spore clones on YPX18 liquid medium (xylose concentration: 180 g/L) at pH 4.0 at a temperature of 35° C. was examined. As a result, of the 8 examined asci there were isolated 2 growing spore clones and 2 non-growing spore clones. That is, isolation was Sxm$^+$:wild type (Sxm$^-$)=2:2 (FIG. 15).

Upon examination in greater detail, no strains were obtained with fast growth comparable to the SxmB$^+$ mutant, and there was a new appearance of 2 groups, a group with slow growth and a group with even slower growth (FIGS. 15a and b). This was assumed to be because one mutation is necessary for growth on YPX18 medium, while the other mutation does not lead to cell growth on YPX18 medium but promotes growth. The mutant gene conferring growth ability on YPX18 medium was named SXM2. In order to confirm this working hypothesis, a diploid was created by cross-breeding the SxmB$^+$ mutant and SCB43 asci #1 and SCB43 asci #3 α strains. However, spore formation was very poor, and surviving cross-breeds could not be obtained of all the 4 spores.

Figure 16:
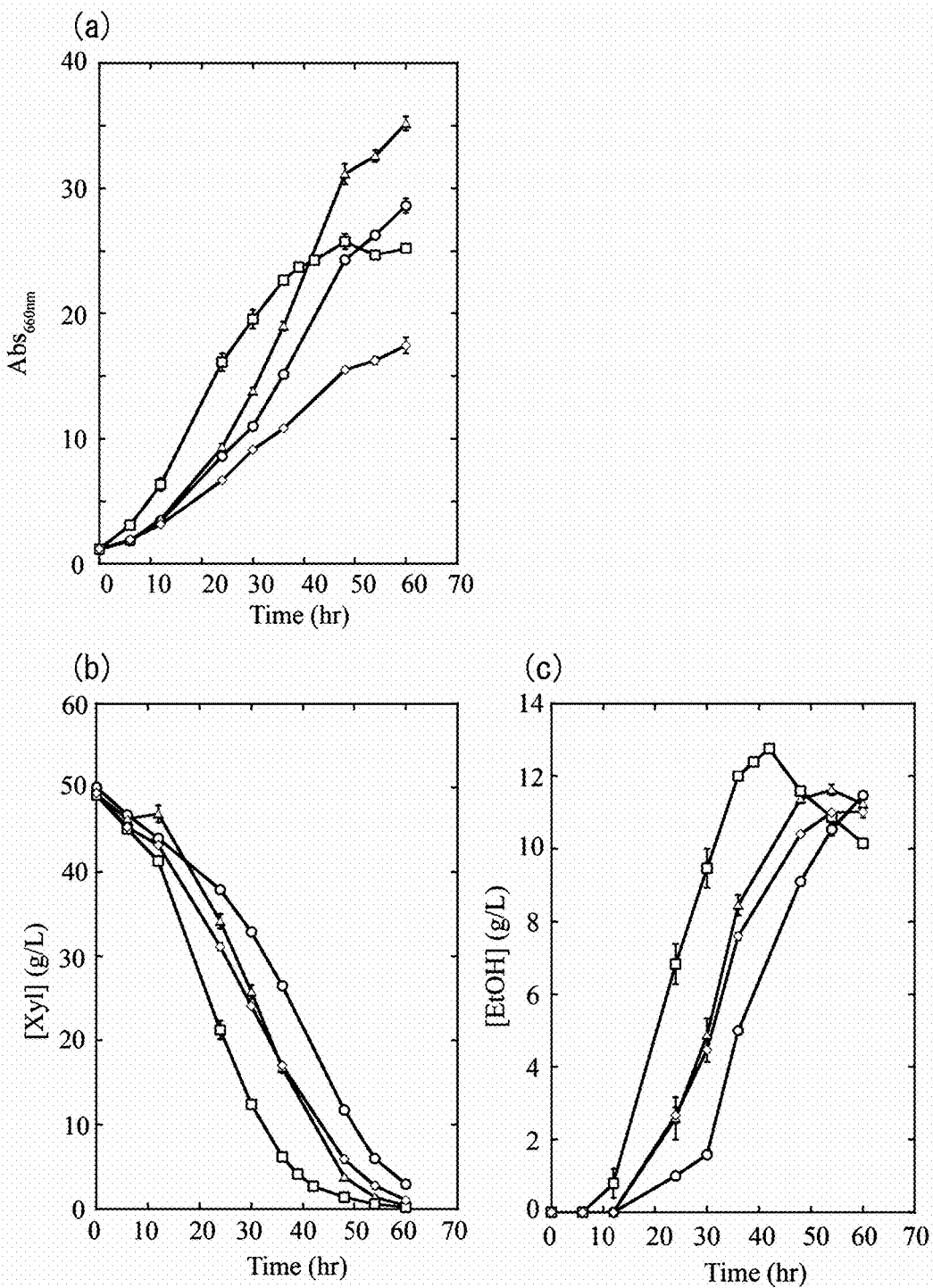
FIG. 16 shows a batch fermentation test using low initial cell concentration: effect of HEX1$_{2-2}$ and Sxm⁺ on fermentation test. A fermentation test was conducted with 4 strains: 2 Sxm⁺ HEX1$_{2-2}$ XM mutants (SCB32 and SCB33), HEX1$_{2-2}$ XM (SCB14) and XM (SCB7). (a) Growth, (b) xylose concentration, (c) ethanol concentration. Symbols: □=SCB32; ◇=SCB33; Δ=SCB14; ○=SCB7.

Batch Fermentation Test for Sxm$^+$ Variants (1) Batch Fermentation Test from Low Initial Cell Concentration Batch fermentation was conducted using the two Sxm$^+$ HEX1$_{2-2}$ XM strains SCB32 and SCB33, the HEX1$_{2-2}$ XM strain SCB14 and the XM strain SCB7, and ethanol productivity from high-concentration xylose was analyzed. They were inoculated into YPX medium containing 50 g/L xylose, pH 4.5 at 32.5° C., with an initial cell concentration Abs$_{660}$=1.0, and shake cultured (60 rpm). Strain SCB32 rapidly grew as time progressed from the start of culturing. Strain SCB14 had the next fastest increase in growth, the final cell concentration being the highest at Abs$_{660nm}$=35. This was followed by strain SCB7, while growth of strain SCB33 was the poorest, with a final cell concentration of just below 20 (FIG. 16a).

The xylose consumption of strain SCB32 was slow at the start of culturing, but rapid consumption was exhibited from 12 hours to 18 hours, being the fasted among the 4 strains. Its maximum consumption rate of xylose was 1.6 g/L/hr (FIG. 16b). The xylose consumption rate of strain SCB14 was rapid during the period from 24 hours to 48 hours with active cell growth, but the most rapid rate per cell was SCB32 or SCB33 (FIG. 16b). Ethanol production by strain SCB32 increased with progressive xylose consumption, with SCB32 exhibiting the most rapid fermentation among the 4 strains (FIG. 16c). However, SCB33 was also thought to be high in terms of yield per cell.

It should be particularly noted that numerous natural mutants growing in uracil-added high-concentration xylose minimal medium could be isolated from strain SCB14, but their xylose consumption was all poor (data not shown). It was assumed that cell growth occurred by metabolism from components in yeast nitrogen base or from uracil. Consequently, in order to isolate variants with enhanced xylose consumption it was necessary to provide a nutrient-rich medium.

Figure 17:
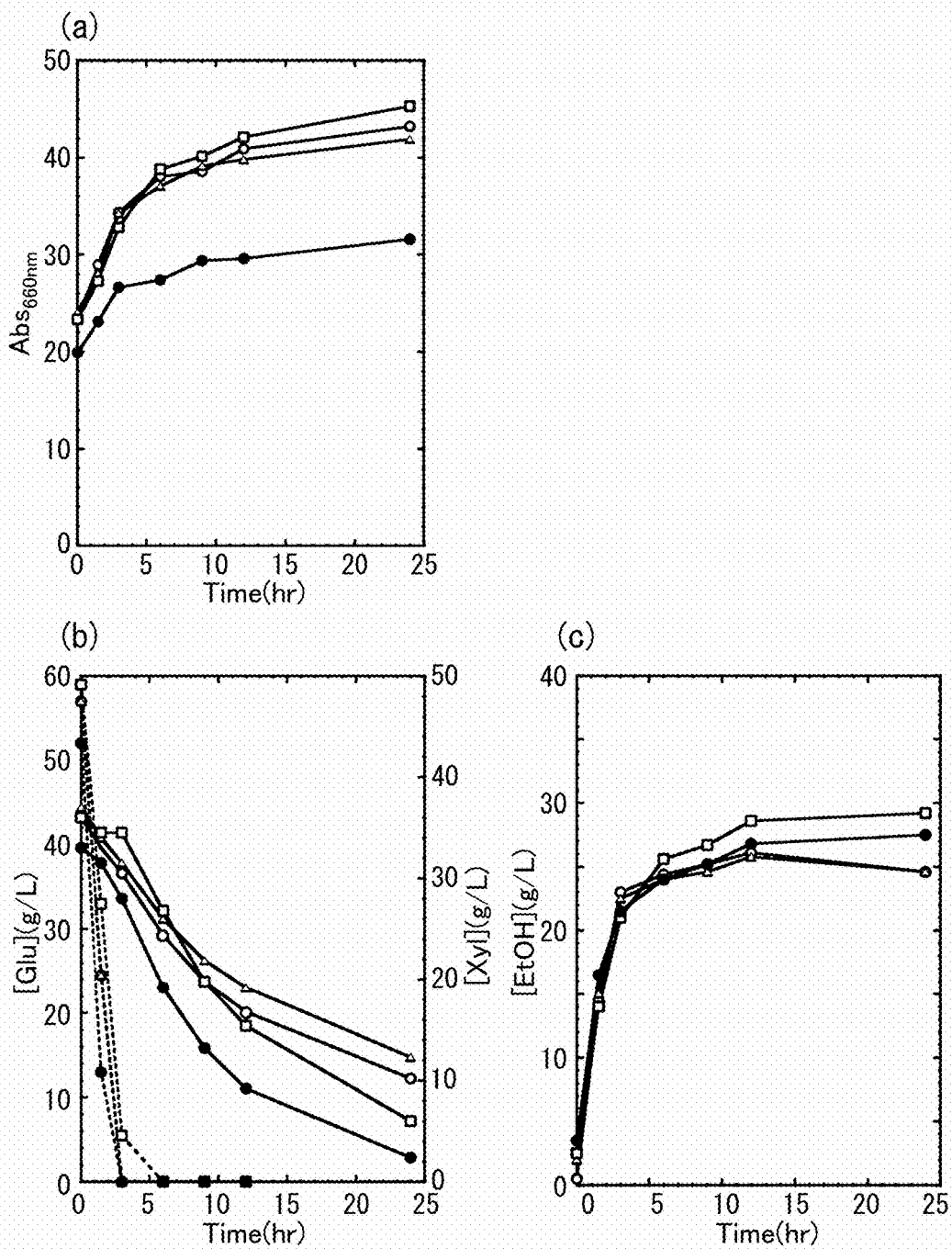
FIG. 17 shows graphs obtained by a batch fermentation test from high initial cell concentration. A fermentation test was conducted with 4 strains: 2 Sxm⁺ HEX1$_{2-2}$ XM mutants (SCB39 and SCB40), HEX1$_{2-2}$ XM (SCB38) and XM (SCC2-11B). (a) Growth, (b) glucose and xylose concentrations, (c) ethanol concentration. Symbols: □=SCB39; ●=SCB40; Δ=SCB38; ○=SCC2-11B.

(2) Glucose/Xylose Copresent Fermentation Test from High Initial Cell Concentration A glucose/xylose copresent fermentation test was conducted with the two Sxm$^+$ HEX1$_{2-2}$ XM strains SCB39 and SCB40, the HEX1$_{2-2}$ XM strain SCB38 and the XM strain SCC2-11B, using cells with a high initial cell concentration. Specifically, they were inoculated into YPD6X4 medium containing 60 g/L glucose and 40 g/L xylose at pH 4.5, 32.5° C., with an initial cell concentration Abs$_{660nm}$=20, and shake cultured (60 rpm). All of the strains other than SCB40 exhibited very similar growth, the cell concentration reaching over Abs$_{660nm}$=40 at 24 hours of culturing (FIG. 17a).

On the other hand, growth was poor with SCB40 alone, the cell concentration at 24 hours being about Abs$_{660nm}$=30. All of the strains consumed 60 g/L concentration glucose within 3 hours. The two variants SCB39 and SCB40 consumed xylose more rapidly than the other two strains. The maximum consumption rate of xylose was 2.6 g/L/hr with SCB39 and 2.9 g/L/hr with SCB40 (FIG. 17b). Xylose consumption was particularly high with SCB40, the residual xylose concentration falling to 2.4 g/L within 24 hours despite a low increase in cells. The two variants SCB39 and SCB40 produced ethanol at 29.2 g/L and 27.5 g/L, respectively, by 24 hours after the start of fermentation, and the ethanol theoretical yields were 60% and 65%, respectively, despite different initial sugar concentrations.

Identification of SXM1 and SXM2 Genes

The SXM1 and SXM2 genes were thought to be an MTH1 mutation and GRR1 mutation, respectively, based on next-generation sequencer analysis. It was first analyzed whether or not SXM1 is MTH1 (FIG. 18).

Figure 19:
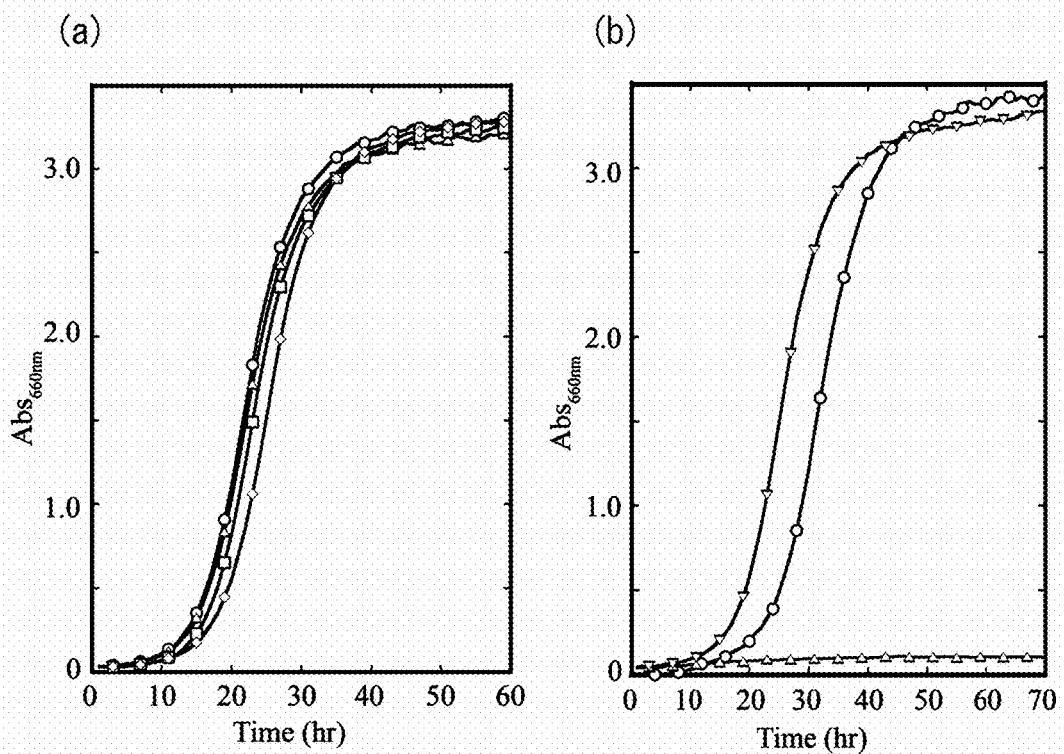
FIG. 19 shows experimental results for identification of an SXM1 mutation. (a) Growth of kanMX MTH1. (b) Growth of HEX1$_{2-2}$ transformants with kanMX MTH1 DNA. Symbols: (a) Δ=SCB39; ○, □, ◇=kanMX MTH1; (b) Δ=SCB38; ∇=SCB39; ○=kanMX MTH1 HEX1$_{2-2}$ transformants.

A strain was constructed by recombining kanMX in the region downstream from the MTH1 gene of the SxmA$^+$ strain SCB32 (FIG. 18b). Growth of the strain on YPX18 medium (xylose concentration: 180 g/L) at pH 4.0, 35° C. temperature was examined, and growth similar to the parent strain SCB32 was observed (FIG. 19a). Thus, it was confirmed that there was no effect on the SxmA$^+$ phenotype even with insertion of the kanMX gene into the region downstream from the mutant SXM1 (MTH1). Next, PCR amplification was conducted from the mutation site of the chromosomal DNA of the constructed strain up to the region containing the kanMX gene, and G418-resistant transformants of HEX1$_{2-2}$ (SCB38) due to the amplified DNA were obtained. When growth of the transformants on YPX18 medium, pH 4.0, 35° C. temperature was examined, the exhibited growth was similar to the SXM1 variant (FIG. 19b). That is, the SXM1 mutation was shown to be the MTH1 gene. Also, upon determining the nucleotide sequence of the mutant MTH1, it was confirmed to be a substitution mutation in the structural gene (corresponding to a substitution of aspartic acid for alanine at position 81 of SEQ ID NO: 7).

Figure 20:
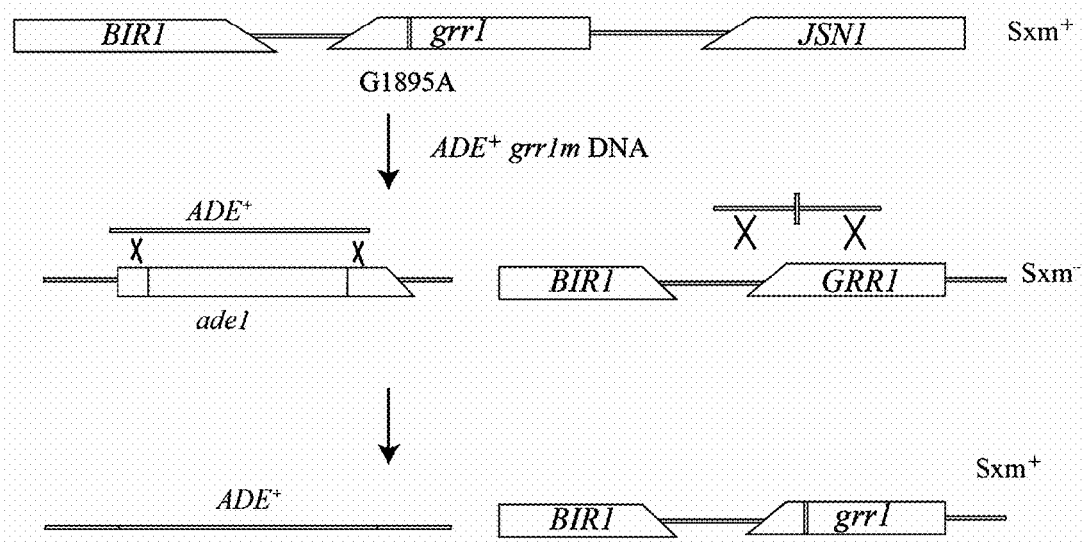
FIG. 20 shows a method of identifying an SXM2 mutation by double transformation. Using strain ade1Δ1 HEX1$_{2-2}$ XM as the recipient strain, Ade⁺ transformants were obtained with ADE⁺ DNA and 2 kb DNA consisting of 1 kb downstream and upstream of the mutation site of the GRR1 gene. If transformants including the mutation site can be isolated from among the Ade⁺ transformants, then SXM2 is understood to be GRR1. Since the gene structure is a grr1 HEX1$_{2-2}$ XM gene structure, this is advantageous in that the conclusion is a clear result.
Figure 21:
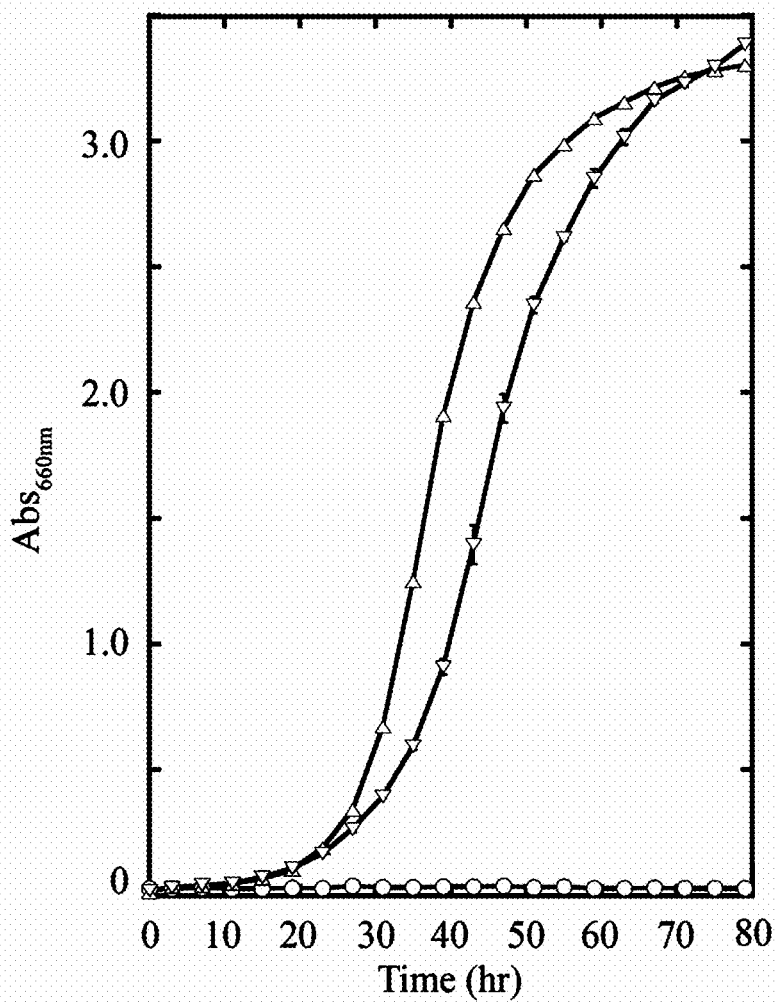
FIG. 21 shows experimental results for identification of SXM2. Symbols: ○=SCB38 (HEX1$_{2-2}$ XM); Δ=SCB40 (SxmB⁺ HEX1$_{2-2}$ XM); ∇=Ade⁺ grr1 double transformant SCC25 (grr1 HEX1$_{2-2}$ XM).

It was then analyzed whether or not SXM2 is the GRR1 gene (FIG. 20). Specifically, ADE1$^+$ DNA and mutant GRR1 DNA were added to strain ade1Δ1 HEX1$_{2-2}$, and Ade$^+$ transformants were obtained. Next, 100 of the transformants were selected and streaked onto 180 g/L xylose-containing SX18 minimal solid medium at pH 5.5 using a platinum wire, and stationary cultured at 30° C. for 2-4 days. Two of the colonies produced after culturing were selected and their growth confirmed on YPX18 medium, pH 5.5, whereby growth was observed (FIG. 21). Also, upon determining the nucleotide sequence of the mutant GRR1 gene, the expected substitution mutation was found in the structural gene (corresponding to a substitution of tyrosine for cysteine at position 632 of SEQ ID NO: 8). It was thus concluded that the SXM2 gene is the GRR1 gene.

Genetic Analysis of $MTH1_{32}$ and $grr1_{33}$ Mutations

Figure 22:
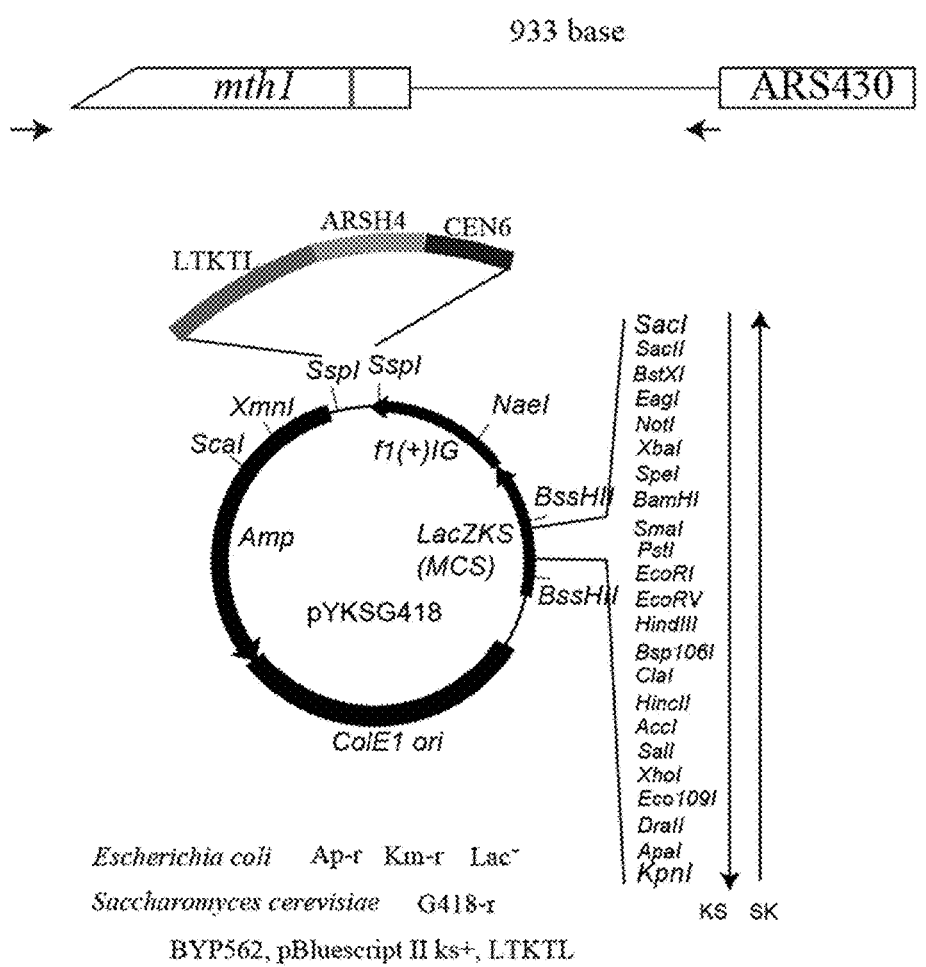
FIG. 22 is a diagram for cloning of the MTH1$_{32}$ mutant gene.

It was examined whether or not the $MTH1_{32}$ mutation is dominant with respect to the wild-type allele. Using SCB32 chromosomal DNA as template, PCR amplification was carried out on a section 1 kb upstream to 0.3 kb downstream of the $MTH1_{32}$ mutant gene, with a pair of primers F-MTH1-UP1K (NotI) (SEQ ID NO: 3) and R-MTH1-DWN300 (NotI) (SEQ ID NO: 4), and cutting was performed with restriction enzyme NotI. A recombinant plasmid was constructed by inserting the fragment into the NotI site of a low-copy plasmid, and it was recovered as an Ap-r Lac$^-$ strain of E. coli DH10B (FIG. 22). Also, PCR analysis and nucleotide sequence analysis were conducted, confirming that the recombinant plasmid definitely had the gene structure according to the experiment design. SCB38 ($HEX1_{2-2}$) was transformed with the plasmid pMTH1 DNA, and strains retaining the plasmid were isolated as G418-resistant transformants.

Figure 23:
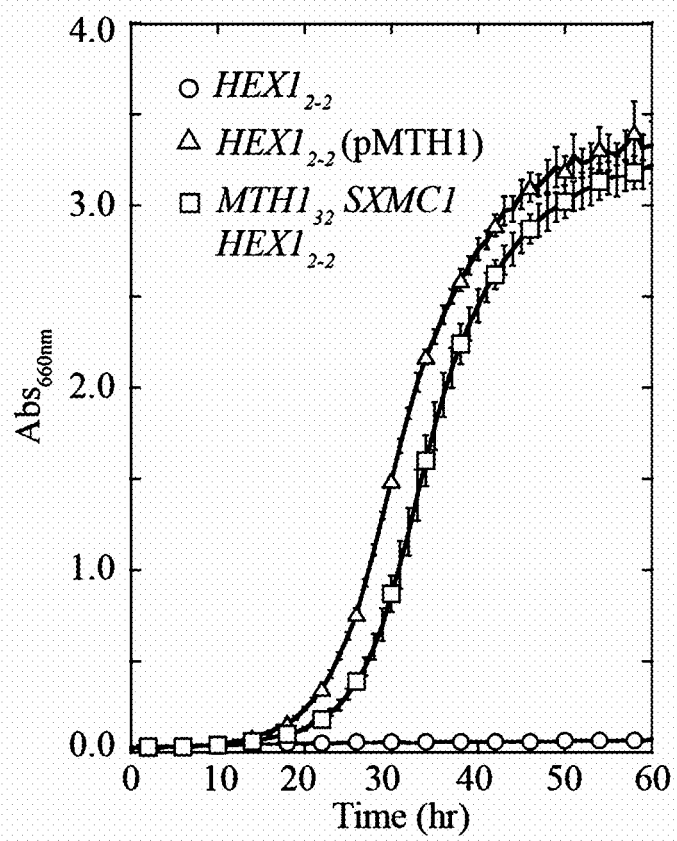
FIG. 23 shows experimental results demonstrating that the MTH1$_{32}$ mutation is dominant with respect to the wild-type allele. The SxmA⁺ variant (MATa SxmA⁺ HEX1$_{2-2}$), parent strain SCB38 (MATa HEX1$_{2-2}$) and SCB38 (pMTH1) were used. Three test cell types were inoculated into 5 mL of YPX18 medium (180 g/L xylose concentration) at pH 4.0 to an initial cell concentration of Abs$_{660nm}$=0.014, and growth was monitored with a biophotorecorder. Symbols: ○=HEX1$_{2-2}$ SCB38; □=SxmA⁺ variant SCB39; Δ=HEX1$_{2-2}$ transformant with pMTH1.

When growth of the transformants was examined on high-concentration xylose medium YPX18 (xylose concentration: 180 g/L), pH 4.0, 35° C. temperature, strain SCB38 (pMTH1) exhibited notable growth differing from the parent strain SCB38 (FIG. 23). It was concluded from this that the $MTH1_{32}$ mutation is dominant with respect to the wild-type allele. Also, growth of strain SCB (pMTH1) was faster growth, though only slightly, compared to strain SCB39 ($MTH1_{32}$ SXMC1). This suggested that because mutant MTH1 was expressed on the plasmid, the amount of protein increased, thereby having an effect on growth.

Figure 24:
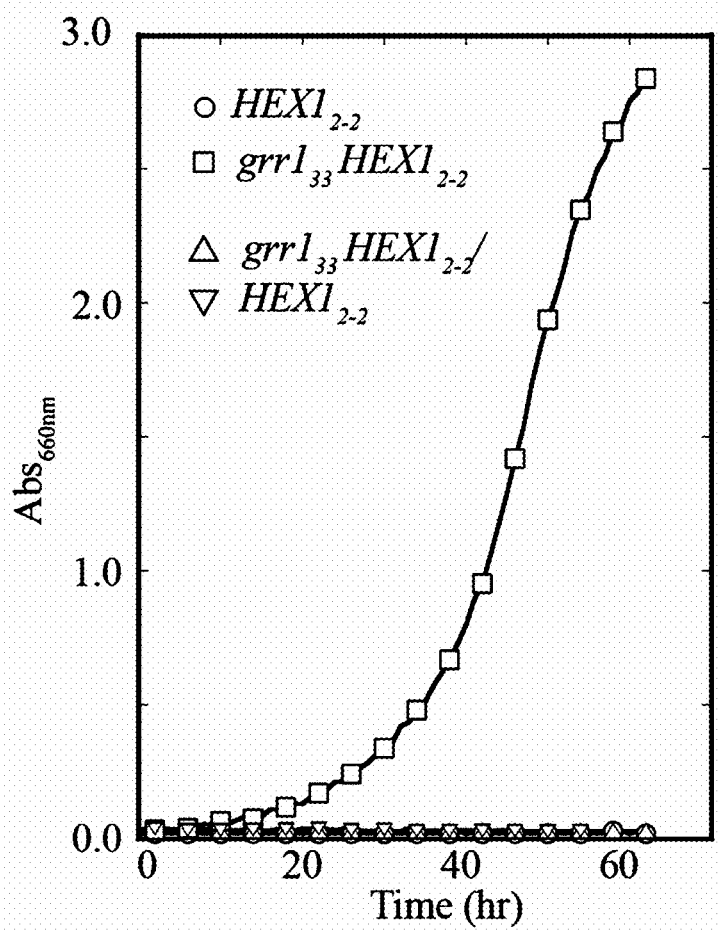
FIG. 24 shows experimental results demonstrating that the grr1$_{33}$ mutation is recessive with respect to the wild-type allele. The grr1$_{33}$ variant (MATa grr1$_{33}$ HEX1$_{2-2}$), SCB42-1B (MATa HEX1$_{2-2}$), and 2 diploids obtained by cross-breeding them, were inoculated into 5 mL of YPX18 medium (xylose concentration: 180 g/L) at pH 4.0, to an initial cell concentration Abs$_{660nm}$=0.014, and growth was analyzed with a biophotorecorder. Symbols: ○=HEX1$_{2-2}$ SCB42-1B; □=grr1$_{33}$ variant SCC25; Δ, ∇=2 grr1$_{33}$/+ diploids.

Next, in order to examine whether or not the $grr1_{33}$ mutation is recessive with respect to the wild-type allele, a growth test was conducted on YPX18 medium (xylose concentration: 180 g/L) at pH 4.0, 35° C. temperature. As a result, the $grr1_{33}$ $HEX1_{2-2}/HEX1_{2-2}$ diploid did not grow, similar to strain $HEX1_{2-2}$, and therefore the $grr1_{33}$ mutation was shown to be recessive with respect to the wild-type allele (FIG. 24).

Characterization of $MTH1_{32}$ Mutation

Figure 25:
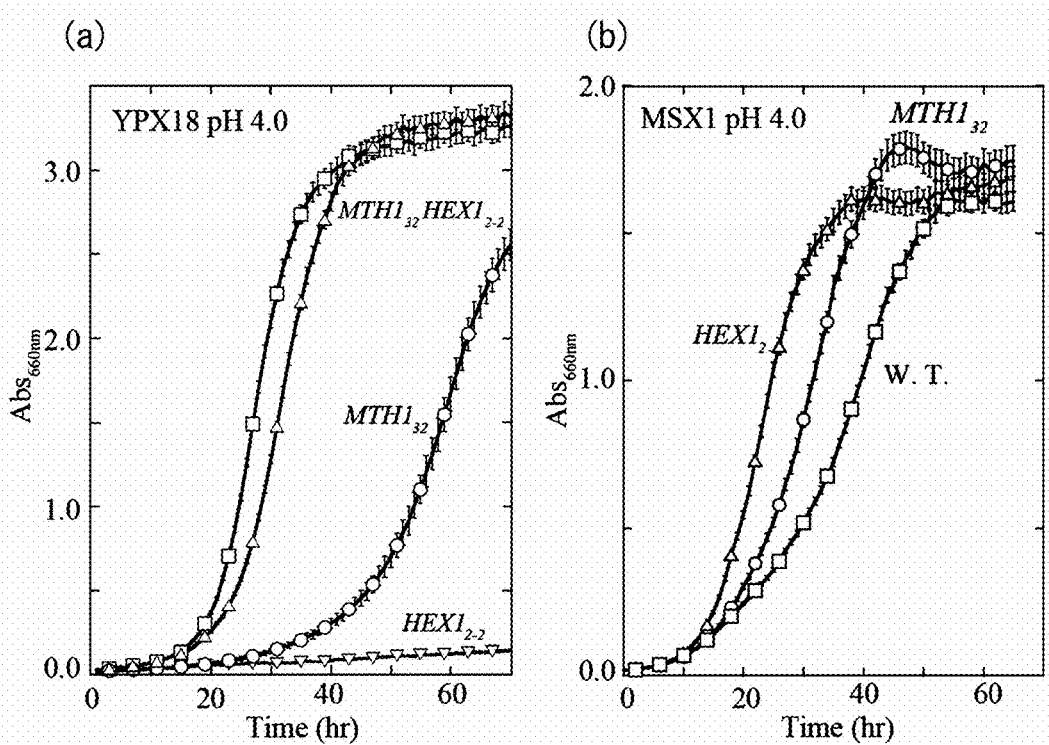
FIG. 25 shows experimental results for characterizing the MTH1$_{32}$ mutation. (a) Growth test for MTH1$_{32}$ single variant, and synergistic effect with HEX1$_{2-2}$. Symbols: ∇=HEX1$_{2-2}$ SCB38; ○=MTH1$_{32}$ single variant; Δ=MTH1$_{32}$ HEX1$_{2-2}$ double variant; □=SxmA⁺ mutant SCB39. (b) Hex⁺ property of MTH1$_{32}$ mutation. Symbols: □=wild type, ○=MTH1$_{32}$ single variant; Δ=HEX1$_{2-2}$ single variant.

It was examined whether or not the $MTH1_{32}$ single variant grows on YPX18 medium (xylose concentration: 180 g/L), at pH 4.0, 35° C. temperature. As a result, growth was clearly observed, unlike with strain $HEX1_{2-2}$ (FIG. 25a). However, the rate of growth was slower than with the $HEX1_{2-2}$ $MTH1_{32}$ double variant. These results suggest that the $MTH1_{32}$ single variant grows in high-concentration xylose medium, and that the $HEX1_{2-2}$ single variant does not grow but that a synergistic effect appears in the double variant. While the SXMC1 single variant does not grow, growth of strain SCB39 ($MTH1_{32}$ SXMC1 $HEX1_{2-2}$ XM) was clearly more rapid than strain $MTH1_{32}$ $HEX1_{2-2}$ XM, and therefore it is thought that even the SXMC1 single mutation exhibits the same Hex$^+$ character as $HEX1_{2-2}$, a synergistic effect with the $MTH1_{32}$ mutation being exhibited.

Since $MTH1_{32}$ and $HEX1_{2-2}$ exhibited a synergistic effect under high-concentration xylose medium conditions, there is a possibility that xylose metabolism is accelerated. It was therefore analyzed whether or not the $MTH1_{32}$ variant exhibits the Hex$^+$ character. A growth test was carried out on 10 g/L xylose-containing MSX medium at pH 4.0, 35° C. temperature. As a result, more rapid growth was clearly exhibited compared to the wild-type strain, although not as rapid as the $HEX1_{2-2}$ variant (FIG. 25b). Consequently, the $MTH1_{32}$ variant was shown to exhibit the Hex$^+$ character, as well as being Sxm$^+$.

The novel strains of the invention, SCB14, SCB15, SCB16, SCB39 and SCB40, were deposited in Japan on Jul. 31, 2013, at the NITE Patent Microorganisms Depositary of the National Institute of Technology and Evaluation. Request was later made for their transfer to an international depository according to the Budapest Treaty, on Aug. 1, 2014, and they were deposited internationally as deposit number NITE BP-01672, deposit number NITE BP-01673, deposit number NITE BP-01674, deposit number NITE BP-01675 and deposit number NITE BP-01676, respectively.

What is claimed is:

1. A recombinant or non-recombinant xylose-assimilating yeast having a gene coding for Mth1p and/or Grr1p, wherein:

the Mth1p is either (a1) a protein consisting of the amino acid sequence SEQ ID NO:7, wherein the alanine at position 81 is substituted by aspartic acid;

(a2) a protein comprising an amino acid sequence having the same function as the protein in (a1), wherein one or up to twenty amino acids of the amino acid sequence of the protein in (a1) are deleted, substituted or added at a position other than the amino acid at position 81, or (a3) a protein consisting of an amino acid sequence having the same function as the protein in (a1) and having at least 90% identity to the amino acid sequence of the protein in (a1), wherein the amino acid corresponding to the alanine at position 81 of SEQ ID NO: 7 is substituted by aspartic acid, and the Grr1p is either (b1) a protein consisting of the amino acid sequence SEQ ID NO: 8, wherein the cysteine at position 632 is substituted by tyrosine;

(b2) a protein consisting of an amino acid sequence having the same function as the protein in (b1), wherein one or more amino acids of the amino acid sequence of the protein of in (b1) are deleted, substituted or added at a position other than the amino acid at position 632, or (b3) a protein consisting of an amino acid sequence having the same function as the protein in (b1) and having at least 90% identity to the amino acid sequence of the protein in (b1), wherein the amino acid corresponding to the cysteine at position 632 of SEQ ID NO: 8 is substituted by tyrosine.

2. The recombinant or non-recombinant xylose-assimilating yeast according to claim 1, further having a gene coding for Cdc19p and/or an upstream region of the GRR1 coding region, wherein:

the Cdc19p is either (c1) a protein consisting of the amino acid sequence SEQ ID NO: 5, wherein the proline at position 272 and/or the alanine at position 344 are respectively substituted by threonine and/or proline;

(c2) a protein comprising an amino acid sequence having the same function as the protein in (c1), wherein one or up to twenty amino acids of the amino acid sequence of the protein in (c1) are deleted, substituted or added at a position other than the amino acid at position 272 and/or 344, or (c3) a protein consisting of an amino acid sequence having the same function as the protein in (c1) and having at least 90% identity to the amino acid sequence of the protein in (c1), wherein the amino acids corresponding to the proline at position 272 and/or the alanine at position 344 of SEQ ID NO: 5 are respectively substituted by threonine and/or proline, and the upstream region of the GRR1 coding region is either (d1) an upstream region having the nucleotide sequence SEQ ID NO: 6, wherein the adenine at position −333 is substituted by thymine;

(d2) an upstream region comprising a nucleotide sequence having the same function as the upstream region in (d1), wherein one or more nucleotides of the nucleotide sequence of the upstream region in (d1) are deleted, substituted or added at a position other than the nucleotide at position −333;

(d3) an upstream region comprising a nucleotide sequence having the same function as the upstream region in (d1) and having at least 90% identity to the nucleotide sequence of the upstream region in (d1), wherein the base corresponding to the adenine at position −333 of SEQ ID NO: 6 is substituted by thymine; or (d4) an upstream region comprising a nucleotide sequence having the same function as the upstream region in (d1), that hybridizes with the nucleotide sequence complementary to the nucleotide sequence of the upstream region in (d1) under conditions for rinsing in a washing solution comprising 0.1×SSC and 0.5% DSS at 68 degrees ° C., wherein the base corresponding to the adenine at position −333 of SEQ ID NO: 6 is substituted by thymine.

3. The yeast according to claim 1, wherein the gene coding for xylose isomerase, xylose reductase, xylitol dehydrogenase and/or xylulokinase is overexpressed.

4. The yeast according to claim 1, wherein the yeast is selected from the group consisting of *Saccharomyces, Kluveromyces, Candida, Pichia, Schizosaccharomyces* and *Hansenula*.

5. The yeast according to claim 4, wherein the yeast is *Saccharomyces*.

6. The yeast according to claim 1, which is capable of growth in the presence of xylose at a high concentration of 180 g/L or greater.

7. A recombinant or non-recombinant xylose-assimilating yeast having a gene coding for Cdc19p and/or an upstream region of the GRR1 coding region, wherein:

the Cdc19p is either (c1) a protein consisting of the amino acid sequence SEQ ID NO: 5, wherein the proline at position 272 and/or the alanine at position 344 are respectively substituted by threonine and/or proline;

(c2) a protein comprising an amino acid sequence having the same function as the protein in (c1), wherein one or up to twenty amino acids of the amino acid sequence of the protein in (c1) are deleted, substituted or added at a position other than the amino acid at position 272 and/or 344, or (c3) a protein consisting of an amino acid sequence having the same function as the protein in (c1) and having at least 90% identity to the amino acid sequence of the protein in (c1), wherein the amino acids corresponding to the proline at position 272 and/or the alanine at position 344 of SEQ ID NO: 5 are respectively substituted by threonine and/or proline, and the upstream region of the GRR1 coding region is either (d1) an upstream region having the nucleotide sequence SEQ ID NO: 6, wherein adenine at position -333 is substituted by thymine;

(d2) an upstream region comprising a nucleotide sequence having the same function as the upstream region in (d1), wherein one or more nucleotides of the nucleotide sequence of the upstream region in (d1) are deleted, substituted or added at a position other than the nucleotide at position −333;

(d3) an upstream region comprising a nucleotide sequence having the same function as the upstream region in (d1) and having at least 90% identity to the nucleotide sequence of the upstream region in (d1), wherein the base corresponding to adenine at position −333 of SEQ ID NO: 6 is substituted by thymine; or (d4) an upstream region comprising a nucleotide sequence having the same function as the upstream region in (d1), that hybridizes with the nucleotide sequence complementary to the nucleotide sequence of the upstream region in (d1) under conditions for rinsing in a washing solution comprising 0.1×SSC and 0.5% DSS at 68 degrees ° C., wherein the base corresponding to adenine at position -333 of SEQ ID NO: 6 is substituted by thymine.

8. The yeast according to claim 1, with deposit number NITE BP-01675 (SCB39), deposited at the NITE Patent Microorganisms Depositary.

9. The yeast according to claim 1, with deposit number NITE BP-01676 (SCB40), deposited at the NITE Patent Microorganisms Depositary.

10. The yeast according to claim 1, with deposit number NITE BP-01672 (SCB14), deposited at the NITE Patent Microorganisms Depositary.

11. The yeast according to claim 1, with deposit number NITE BP-12 (SCB16), deposited at the NITE Patent Microorganisms Depositary.

12. The yeast according to claim 1, with deposit number NITE BP-01673 (SCB15), deposited at the NITE Patent Microorganisms Depositary.

13. A method for producing a useful substance using the yeast according to claim 1 in the presence of xylose, wherein the useful substance is one or more substances selected from the group consisting of ethanol, lactic acid, acetic acid, propanol, isobutanol, butanol, succinic acid and glycerol.

14. The method according to claim 13, wherein the useful substance is ethanol.

* * * * *

SEQUENCE LISTING

```
<160> NUMBER OF SEQ ID NOS: 8

<210> SEQ ID NO 1
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tttccgcggt tagttttgct ggccgcatct tctcaaatat gcttcccagt caatcaatga      60
atcgaaaatg tcatta                                                     76

<210> SEQ ID NO 2
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttgggccca tgtcgaaagc tacatataag gaacgtgctg ctactcatcc cgccagctga      60
```

```
agctt                                                              65

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tttgcggccg caggaagatt aaaatgaact cttcaac                            37

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tttgcggccg ctacgttgga tgtctgcgat                                    30

<210> SEQ ID NO 5
<211> LENGTH: 500
<212> TYPE: PRT
<213> ORGANISM: Saccharomyces cerevisiae

<400> SEQUENCE: 5
```

Met Ser Arg Leu Glu Arg Leu Thr Ser Leu Asn Val Val Ala Gly Ser
1               5                   10                  15

Asp Leu Arg Arg Thr Ser Ile Ile Gly Thr Ile Gly Pro Lys Thr Asn
            20                  25                  30

Asn Pro Glu Thr Leu Val Ala Leu Arg Lys Ala Gly Leu Asn Ile Val
        35                  40                  45

Arg Met Asn Phe Ser His Gly Ser Tyr Glu Tyr His Lys Ser Val Ile
    50                  55                  60

Asp Asn Ala Arg Lys Ser Glu Glu Leu Tyr Pro Gly Arg Pro Leu Ala
65                  70                  75                  80

Ile Ala Leu Asp Thr Lys Gly Pro Glu Ile Arg Thr Gly Thr Thr Thr
                85                  90                  95

Asn Asp Val Asp Tyr Pro Ile Pro Pro Asn His Glu Met Ile Phe Thr
            100                 105                 110

Thr Asp Asp Lys Tyr Ala Lys Ala Cys Asp Asp Lys Ile Met Tyr Val
        115                 120                 125

Asp Tyr Lys Asn Ile Thr Lys Val Ile Ser Ala Gly Arg Ile Ile Tyr
    130                 135                 140

Val Asp Asp Gly Val Leu Ser Phe Gln Val Leu Glu Val Val Asp Asp
145                 150                 155                 160

Lys Thr Leu Lys Val Lys Ala Leu Asn Ala Gly Lys Ile Cys Ser His
                165                 170                 175

Lys Gly Val Asn Leu Pro Gly Thr Asp Val Asp Leu Pro Ala Leu Ser
            180                 185                 190

Glu Lys Asp Lys Glu Asp Leu Arg Phe Gly Val Lys Asn Gly Val His
        195                 200                 205

Met Val Phe Ala Ser Phe Ile Arg Thr Ala Asn Asp Val Leu Thr Ile
    210                 215                 220

```
Arg Glu Val Leu Gly Glu Gln Gly Lys Asp Val Lys Ile Ile Val Lys
225                 230                 235                 240

Ile Glu Asn Gln Gln Gly Val Asn Asn Phe Asp Glu Ile Leu Lys Val
            245                 250                 255

Thr Asp Gly Val Met Val Ala Arg Gly Asp Leu Gly Ile Glu Ile Pro
        260                 265                 270

Ala Pro Glu Val Leu Ala Val Gln Lys Lys Leu Ile Ala Lys Ser Asn
    275                 280                 285

Leu Ala Gly Lys Pro Val Ile Cys Ala Thr Gln Met Leu Glu Ser Met
290                 295                 300

Thr Tyr Asn Pro Arg Pro Thr Arg Ala Glu Val Ser Asp Val Gly Asn
305                 310                 315                 320

Ala Ile Leu Asp Gly Ala Asp Cys Val Met Leu Ser Gly Glu Thr Ala
            325                 330                 335

Lys Gly Asn Tyr Pro Ile Asn Ala Val Thr Thr Met Ala Glu Thr Ala
        340                 345                 350

Val Ile Ala Glu Gln Ala Ile Ala Tyr Leu Pro Asn Tyr Asp Asp Met
    355                 360                 365

Arg Asn Cys Thr Pro Lys Pro Thr Ser Thr Thr Glu Thr Val Ala Ala
370                 375                 380

Ser Ala Val Ala Ala Val Phe Glu Gln Lys Ala Lys Ala Ile Ile Val
385                 390                 395                 400

Leu Ser Thr Ser Gly Thr Thr Pro Arg Leu Val Ser Lys Tyr Arg Pro
            405                 410                 415

Asn Cys Pro Ile Ile Leu Val Thr Arg Cys Pro Arg Ala Ala Arg Phe
        420                 425                 430

Ser His Leu Tyr Arg Gly Val Phe Pro Phe Val Phe Glu Lys Glu Pro
    435                 440                 445

Val Ser Asp Trp Thr Asp Asp Val Glu Ala Arg Ile Asn Phe Gly Ile
450                 455                 460

Glu Lys Ala Lys Glu Phe Gly Ile Leu Lys Lys Gly Asp Thr Tyr Val
465                 470                 475                 480

Ser Ile Gln Gly Phe Lys Ala Gly Ala Gly His Ser Asn Thr Leu Gln
            485                 490                 495

Val Ser Thr Val
        500

<210> SEQ ID NO 6
<211> LENGTH: 733
<212> TYPE: DNA
<213> ORGANISM: Saccharomyces cerevisiae

<400> SEQUENCE: 6
cgtccccatg ttttcttttg ttttcgtcat cattgggaga ccacgccgtt ttcttctcat        60
acctgcatcc attcaaaact atctcattta cccccaacgg ttttatggtt caaatcctaa       120
tagaatatga gcgagctaat gaagaatttg ggcattttca ttactgggaa gacgtgtctt       180
tttcaagcca tcatatcgcc aaatttttttt tctacaccta atcatgatta aataaatcca       240
taaagtttta tacagttttt aaaaatatca tcatttatta cccagatgtg ttaatgaaca       300
tttatagtca tcattactag gctttcatta ctactgaggt tacccgccta tggaccttcc       360
ttggtaaagg aacttgtttt aaaatttgcc ttttaacaaa attagtgata tgattatcaa       420
aaaaggcgtg gcaaaataca taacaccaaa tttaactgtg cctgtgtgtt actttctttt       480
gtccatactt caccagtttt tcgatttac acaataattc gttttcattt aatcgttctc       540
```

```
ttagaagccc ggtttttgaa tatcaaaatc gtacttgtgt ccaactagca gggaagccca    600
aaaattaagg cattgcattt aagcttacac ctgcgtgaaa tcttgaaatt tctcattgat    660
ttcggcacaa taattatcat tggtagtgag gctaaacagt tttgcggttt cctttatact    720
aagaaggtct ata                                                       733
```

<210> SEQ ID NO 7
<211> LENGTH: 433
<212> TYPE: PRT
<213> ORGANISM: Saccharomyces cerevisiae

<400> SEQUENCE: 7

```
Met Phe Val Ser Pro Pro Ala Thr Ser Lys Asn Gln Val Leu Gln
1               5                   10                  15

Arg Arg Pro Leu Glu Ser Thr Asn Ser Asn His Gly Phe Ala Ser Ser
            20                  25                  30

Leu Gln Ala Ile Pro Glu Asn Thr Met Ser Gly Ser Asp Asn Ala Ser
        35                  40                  45

Phe Gln Ser Leu Pro Leu Ser Met Ser Ser Ser Gln Ser Thr Thr Ser
    50                  55                  60

Ser Arg Arg Glu Asn Phe Val Asn Ala Pro Pro Glu Tyr Thr Asp Arg
65                  70                  75                  80

Ala Arg Asp Glu Ile Lys Lys Arg Leu Leu Ala Ser Ser Pro Ser Arg
                85                  90                  95

Arg Ser His His Ser Ser Ser Met His Ser Ala Ser Arg Arg Ser Ser
            100                 105                 110

Val Ala Glu Ser Gly Ser Leu Leu Ser Asp Asn Ala Ser Ser Tyr Gln
        115                 120                 125

Ser Ser Ile Phe Ser Ala Pro Ser Thr Val His Thr Gln Leu Thr Asn
    130                 135                 140

Asp Ser Ser Phe Ser Glu Phe Pro Asn His Lys Leu Ile Thr Arg Val
145                 150                 155                 160

Ser Leu Asp Glu Ala Leu Pro Lys Thr Phe Tyr Asp Met Tyr Ser Pro
                165                 170                 175

Asp Ile Leu Leu Ala Asp Pro Ser Asn Ile Leu Cys Asn Gly Arg Pro
            180                 185                 190

Lys Phe Thr Lys Arg Glu Leu Leu Asp Trp Asp Leu Asn Asp Ile Arg
        195                 200                 205

Ser Leu Leu Ile Val Glu Lys Leu Arg Pro Glu Trp Gly Asn Gln Leu
    210                 215                 220

Pro Glu Val Ile Thr Val Gly Asp Asn Met Pro Gln Phe Arg Leu Gln
225                 230                 235                 240

Leu Leu Pro Leu Tyr Ser Ser Asp Glu Thr Ile Ile Ala Thr Leu Val
                245                 250                 255

His Ser Asp Leu Tyr Met Glu Ala Asn Leu Asp Tyr Glu Phe Lys Leu
            260                 265                 270

Thr Ser Ala Lys Tyr Thr Val Ala Thr Ala Arg Lys Arg His Glu His
        275                 280                 285

Ile Thr Gly Arg Asn Glu Ala Val Met Asn Leu Ser Lys Pro Glu Trp
    290                 295                 300

Arg Asn Ile Ile Glu Asn Tyr Leu Leu Asn Ile Ala Val Glu Ala Gln
305                 310                 315                 320

Cys Arg Phe Asp Phe Lys Gln Arg Cys Ser Glu Tyr Lys Lys Trp Lys
                325                 330                 335
```

```
Leu Gln Gln Ser Asn Leu Lys Arg Pro Asp Met Pro Pro Ser Ile
                340                 345                 350

Ile Pro Arg Lys Asn Ser Thr Glu Thr Lys Ser Leu Leu Lys Ala
            355                 360                 365

Leu Leu Lys Asn Ile Gln Leu Lys Asn Pro Asn Asn Leu Asp Glu
        370                 375                 380

Leu Met Met Arg Ser Ser Ala Ala Thr Asn Gln Gln Gly Lys Asn Lys
385                 390                 395                 400

Val Ser Leu Ser Lys Glu Glu Lys Ala Thr Ile Trp Ser Gln Cys Gln
                405                 410                 415

Ala Gln Val Tyr Gln Arg Leu Gly Leu Asp Trp Gln Pro Asp Ser Val
                420                 425                 430

Ser

<210> SEQ ID NO 8
<211> LENGTH: 1148
<212> TYPE: PRT
<213> ORGANISM: Saccharomyces cerevisiae

<400> SEQUENCE: 8

Met Asp Gln Asp Asn Asn Asn His Asn Asp Ser Asn Arg Leu His Pro
1               5                   10                  15

Pro Asp Ile His Pro Asn Leu Gly Pro Gln Leu Trp Leu Asn Ser Ser
            20                  25                  30

Gly Asp Phe Asp Asp Asn Asn Asn Asn Asn Asn Asn Asn Ser Thr
        35                  40                  45

Arg Pro Gln Met Pro Ser Arg Thr Arg Glu Thr Ala Thr Ser Glu Arg
    50                  55                  60

Asn Ala Ser Glu Val Arg Asp Ala Thr Leu Asn Asn Ile Phe Arg Phe
65                  70                  75                  80

Asp Ser Ile Gln Arg Glu Thr Leu Leu Pro Thr Asn Asn Gly Gln Pro
                85                  90                  95

Leu Asn Gln Asn Phe Ser Leu Thr Phe Gln Pro Gln Gln Thr Asn
            100                 105                 110

Ala Leu Asn Gly Ile Asp Ile Asn Thr Val Asn Thr Asn Leu Met Asn
        115                 120                 125

Gly Val Asn Val Gln Ile Asp Gln Leu Asn Arg Leu Leu Pro Asn Leu
    130                 135                 140

Pro Glu Glu Glu Arg Lys Gln Ile His Glu Phe Lys Leu Ile Val Gly
145                 150                 155                 160

Lys Lys Ile Gln Glu Phe Leu Val Val Ile Glu Lys Arg Arg Lys Lys
                165                 170                 175

Ile Leu Asn Glu Ile Glu Leu Asp Asn Leu Lys Leu Lys Glu Leu Arg
            180                 185                 190

Ile Asp Asn Ser Pro Gln Ala Ile Ser Tyr Leu His Lys Leu Gln Arg
        195                 200                 205

Met Arg Leu Arg Ala Leu Glu Thr Glu Asn Met Glu Ile Arg Asn Leu
    210                 215                 220

Arg Leu Lys Ile Leu Thr Ile Ile Glu Glu Tyr Lys Lys Ser Leu Tyr
225                 230                 235                 240

Ala Tyr Cys His Ser Lys Leu Arg Gly Gln Gln Val Glu Asn Pro Thr
                245                 250                 255

Asp Asn Phe Ile Ile Trp Ile Asn Ser Ile Asp Thr Thr Glu Ser Ser
            260                 265                 270
```

```
Asp Leu Lys Glu Gly Leu Gln Asp Leu Ser Arg Tyr Ser Arg Gln Phe
    275                 280                 285
Ile Asn Asn Val Leu Ser Pro Ser Asn Gln Asn Ile Cys Thr Ser
    290                 295                 300
Val Thr Arg Arg Ser Pro Val Phe Ala Leu Asn Met Leu Pro Ser Glu
305                 310                 315                 320
Ile Leu His Leu Ile Leu Asp Lys Leu Asn Gln Lys Tyr Asp Ile Val
                    325                 330                 335
Lys Phe Leu Thr Val Ser Lys Leu Trp Ala Glu Ile Ile Val Lys Ile
                340                 345                 350
Leu Tyr Tyr Arg Pro His Ile Asn Lys Lys Ser Gln Leu Asp Leu Phe
            355                 360                 365
Leu Arg Thr Met Lys Leu Thr Ser Glu Glu Thr Val Phe Asn Tyr Arg
370                 375                 380
Leu Met Ile Lys Arg Leu Asn Phe Ser Phe Val Gly Asp Tyr Met His
385                 390                 395                 400
Asp Thr Glu Leu Asn Tyr Phe Val Gly Cys Lys Asn Leu Glu Arg Leu
                405                 410                 415
Thr Leu Val Phe Cys Lys His Ile Thr Ser Val Pro Ile Ser Ala Val
                420                 425                 430
Leu Arg Gly Cys Lys Phe Leu Gln Ser Val Asp Ile Thr Gly Ile Arg
            435                 440                 445
Asp Val Ser Asp Asp Val Phe Asp Thr Leu Ala Thr Tyr Cys Pro Arg
        450                 455                 460
Val Gln Gly Phe Tyr Val Pro Gln Ala Arg Asn Val Thr Phe Asp Ser
465                 470                 475                 480
Leu Arg Asn Phe Ile Val His Ser Pro Met Leu Lys Arg Ile Lys Ile
                485                 490                 495
Thr Ala Asn Asn Asn Met Asn Asp Glu Leu Val Glu Leu Leu Ala Asn
            500                 505                 510
Lys Cys Pro Leu Leu Val Glu Val Asp Ile Thr Leu Ser Pro Asn Val
        515                 520                 525
Thr Asp Ser Ser Leu Leu Lys Leu Leu Thr Arg Leu Val Gln Leu Arg
    530                 535                 540
Glu Phe Arg Ile Thr His Asn Thr Asn Ile Thr Asp Asn Leu Phe Gln
545                 550                 555                 560
Glu Leu Ser Lys Val Val Asp Asp Met Pro Ser Leu Arg Leu Ile Asp
                565                 570                 575
Leu Ser Gly Cys Glu Asn Ile Thr Asp Lys Thr Ile Glu Arg Ile Val
            580                 585                 590
Asn Leu Ala Pro Lys Leu Arg Asn Val Phe Leu Gly Lys Cys Ser Arg
        595                 600                 605
Ile Thr Asp Ala Ser Leu Phe Gln Leu Ser Lys Leu Gly Lys Asn Leu
    610                 615                 620
Gln Thr Val His Phe Gly His Cys Phe Asn Ile Thr Asp Asn Gly Val
625                 630                 635                 640
Arg Ala Leu Phe His Ser Cys Thr Arg Ile Gln Tyr Val Asp Phe Ala
                645                 650                 655
Cys Cys Thr Asn Leu Thr Asn Arg Thr Leu Tyr Glu Leu Ala Asp Leu
            660                 665                 670
Pro Lys Leu Lys Arg Ile Gly Leu Val Lys Cys Thr Gln Met Thr Asp
        675                 680                 685
```

```
Glu Gly Leu Leu Asn Met Val Ser Leu Arg Gly Arg Asn Asp Thr Leu
    690             695                 700
Glu Arg Val His Leu Ser Tyr Cys Ser Asn Leu Thr Ile Tyr Pro Ile
705             710                 715                 720
Tyr Glu Leu Leu Met Ser Cys Pro Arg Leu Ser His Leu Ser Leu Thr
                725                 730                 735
Ala Val Pro Ser Phe Leu Arg Pro Asp Ile Thr Met Tyr Cys Arg Pro
            740                 745                 750
Ala Pro Ser Asp Phe Ser Glu Asn Gln Arg Gln Ile Phe Cys Val Phe
        755                 760                 765
Ser Gly Lys Gly Val His Lys Leu Arg His Tyr Leu Val Asn Leu Thr
770             775                 780
Ser Pro Ala Phe Gly Pro His Ala Asp Val Asn Asp Val Leu Thr Lys
785             790                 795                 800
Tyr Ile Arg Ser Lys Asn Leu Ile Phe Asn Gly Glu Thr Leu Glu Asp
                805                 810                 815
Ala Leu Arg Arg Ile Ile Thr Asp Leu Asn Gln Asp Ser Ala Ala Ile
            820                 825                 830
Ile Ala Ala Thr Gly Leu Asn Gln Ile Asn Gly Leu Asn Asn Asp Phe
        835                 840                 845
Leu Phe Gln Asn Ile Asn Phe Glu Arg Ile Asp Glu Val Phe Ser Trp
850             855                 860
Tyr Leu Asn Thr Phe Asp Gly Ile Arg Met Ser Ser Glu Glu Val Asn
865             870                 875                 880
Ser Leu Leu Leu Gln Val Asn Lys Thr Phe Cys Glu Asp Pro Phe Ser
                885                 890                 895
Asp Val Asp Asp Asp Gln Asp Tyr Val Val Ala Pro Gly Val Asn Arg
            900                 905                 910
Glu Ile Asn Ser Glu Met Cys His Ile Val Arg Lys Phe His Glu Leu
        915                 920                 925
Asn Asp His Ile Asp Asp Phe Glu Val Asn Val Ala Ser Leu Val Arg
930             935                 940
Val Gln Phe Gln Phe Thr Gly Phe Leu Leu His Glu Met Thr Gln Thr
945             950                 955                 960
Tyr Met Gln Met Ile Glu Leu Asn Arg Gln Ile Cys Leu Val Gln Lys
                965                 970                 975
Thr Val Gln Glu Ser Gly Asn Ile Asp Tyr Gln Lys Gly Leu Leu Ile
            980                 985                 990
Trp Arg Leu Leu Phe Ile Asp Lys Phe Ile Met Val Val Gln Lys Tyr
        995                 1000                1005
Lys Leu Ser Thr Val Val Leu Arg Leu Tyr Leu Lys Asp Asn Ile
    1010            1015                1020
Thr Leu Leu Thr Arg Gln Arg Glu Leu Leu Ile Ala His Gln Arg
    1025            1030                1035
Ser Ala Trp Asn Asn Asn Asn Asp Asn Asp Ala Asn Arg Asn Ala
    1040            1045                1050
Asn Asn Ile Val Asn Ile Val Ser Asp Ala Gly Thr Asn Asp Thr
    1055            1060                1065
Ser Asn Asn Glu Thr Asn Asn Gly Asn Asp Asp Asn Glu Thr Glu
    1070            1075                1080
Asn Pro Asn Phe Trp Arg Gln Phe Gly Asn Arg Met Gln Ile Ser
    1085            1090                1095
Pro Asp Gln Met Arg Asn Leu Gln Met Gly Leu Arg Asn Gln Asn
```

-continued

```
              1100                1105                1110
Met Val  Arg Asn Asn Asn  Asn Thr Ile Asp Glu  Ser Met Pro
    1115              1120                1125

Asp Thr  Ala Ile Asp Ser  Gln Met Asp Glu Ala  Ser Gly Thr Pro
    1130              1135                1140

Asp Glu  Asp Met Leu
    1145
```